(12) United States Patent
Rosenfeld et al.

(10) Patent No.: US 7,211,402 B2
(45) Date of Patent: May 1, 2007

(54) TRANSCRIPTION FACTOR COACTIVATOR PROTEIN, P/CIP

(75) Inventors: Michael G. Rosenfeld, San Diego, CA (US); Christopher K. Glass, San Diego, CA (US); David W. Rose, San Diego, CA (US); Joseph Torchia, London (CA)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/971,982

(22) Filed: Oct. 21, 2004

(65) Prior Publication Data

US 2005/0244889 A1    Nov. 3, 2005

Related U.S. Application Data

(62) Division of application No. 09/445,353, filed as application No. PCT/US98/12263 on Jun. 12, 1998, now Pat. No. 6,812,336.

(60) Provisional application No. 60/049,452, filed on Jun. 12, 1997.

(51) Int. Cl.
  *G01N 33/53*     (2006.01)
  *C07K 14/47*     (2006.01)

(52) U.S. Cl. .................................... 435/7.1; 550/350

(58) Field of Classification Search ..................... None
    See application file for complete search history.

(56) References Cited

OTHER PUBLICATIONS

GenBank Accession No. AF000581.
GenBank Accession No. AF000582.
Arias et al., "Activation of cAMP and mitogen responsive genes relies on a common nuclear factor," *Nature* 370:226-229 (1994).
Bhattacharya et al., "Cooperation of Stat2 and p300/CBP in signalling induced by interferon-alpha," *Nature* 383:344-347 (1996).
Bisotto et al., "Identification and characterization of a novel transcriptional activation domain in the CREB-binding protein," *J. Biol. Chem.* 271:17746-17750 (1996).
Cavailles et al., "Nuclear factor RIP140 modulates transcriptional activation by the estrogen receptor," *Embo J.* 14:3741-3751 (1995).
Chakravarti et al., "Role of CBP/P300 in nuclear receptor signalling," *Nature* 383:99-103 (1996).
Chen et al., "Nuclear receptor coactivator ACTR is a novel histone acetyltransferase and forms a multimeric activation complex with P/CAf and CBP/p300," *Cell* 90:569-580 (1997).
Eckner et al., "Interaction and functional collaboration of p300/CBP and bHLH proteins in muscle and B-cell differentiation," *Genes and Devel.* 10(19): 2478-2490 (1996).
Halachmi et al., "Estrogen receptor-associated proteins: possible mediators of hormone-induced transcription," *Science* 264:1455-1458 (1994).

Hong et al., "GRIP1, a novel mouse protein that serves as a transcriptional coactivator in yeast for the hormone binding domains of steroid receptors," *Proc. Natl. Acad. Sci. USA* 93:4948-4952 (1996).
Hong et al., "GRIP1, a Transcriptional Coactivator for the AF-2 Transactivation Domain of Steroid, Thyroid, Retinoid, and Vitamin D Receptors," *Molecular and Cellular Biology* 17:2735-2744 (1997).
Horvai et al., "Nuclear integration of JAK/STAT and Ras/AP-1 signaling by CBP and p300," *Proc. Natl. Acad. Sci. USA* 94:1074-1079 (1997).
Kurokawa et al., "Polarity-specific activities of retinoic acid receptors determined by a co-repressor," *Nature* 377:451-454 (1995).
Kwok et al., "Nuclear protein CBP is a coactivator for the transcription factor CREB," *Nature* 370:223-226 (1994).
Le Douarin et al., "The N-terminal part of TIF1, a putative mediator of the ligand-dependent activation function (AF-2) of nuclear receptors, is fused to B-raf in the oncogenic protein T18," *Embo J.* 14:2020-2033 (1995).
Lee et al., "Interaction of thyroid-hormone receptor with a conserved transcriptional mediator," *Nature* 374:91-94 (1995).
Li et al., "RAC3, a steroid/nuclear receptor-associated coactivator that is related to SRC-1 and TIF2," *Proc. Natl. Acad. Sci. USA* 94:8479-8484 (1997).
Nakajima et al., "Analysis of a cAMP-responsive activator reveals a two-component mechanism for transcriptional induction via signal-dependent factors," *Genes and Devel.* 11:738-747 (1997).
Ogryzko et al., "The transcriptional coactivators p300 and CBP are histone acetyltransferases," *Cell* 87:953-960 (1996).
Onate et al., "Sequence and characterization of a coactivator for the steroid hormone receptor superfamily," *Science* 270:1354-1357 (1995).
Smith et al., "CREB binding protein acts synergistically with steroid receptor coactivator-1 to enhance steroid receptor-dependent transcription," *Proc. Natl. Acad. Sci., USA* 93:8884-8888 (1996).
Swope et al., "CREB-binding protein activates transcription through multiple domains," *J. Biol. Chem.* 271:28138-28145 (1996).
Torchia et al., "The transcriptional co-activator p/CIP binds CBP and mediates nuclear-receptor function," *Nature* 387:677-684 (1997).
Voegel et al., "TIF2, a 160 kDa transcriptional mediator for the ligand-dependent activation function AF-2 of nuclear receptors," *Embo J.* 15:3667-3675 (1996).
Zhang et al., "Two contact regions between Stat1 and CBP/p300 in interferon gamma signaling," *Proc. Natl. Acad. Sci. USA* 93:15092-15096 (1996).

*Primary Examiner*—Nancy Vogel
(74) *Attorney, Agent, or Firm*—Gordon & Rees LLP

(57) ABSTRACT

The present invention provides a substantially purified nucleic acid molecule encoding a p/CIP polypeptide, which regulates the activity of CBP/p300-dependent transcription factors. The invention also provides a substantially purified p-CIP polypeptide and active fragments thereof. In addition, the invention provides methods of identifying an effective agent that alters the association of a p/CIP polypeptide with a second protein. Further provided herein are methods of selectively inhibiting signal transduction pathways using an active fragment of a p/CIP polypeptide or a nucleic acid molecule encoding such an acive fragment.

10 Claims, 30 Drawing Sheets

```
      GGCGGCGAACGGATCAAAAGAATTTGCTGAACAGTGGACTCCGAGATCGGTAAAACGAAC
  1   ------------+---------+---------+---------+---------+---------+ 60(20)
      CCGCCGCTTGCCTAGTTTTCTTAAACGACTTGTCACCTGAGGCTCTAGCCATTTTGCTTG

TCTTCCCTGCCCTTCCTGAACAGCTGTCAGTTGCTGATCTGTGATCAGGATGAGTGGACT
 61   ------------+---------+---------+---------+---------+---------+ 120(40)
      AGAAGGGACGGGAAGGACTTGTCGACAGTCAACGACTAGACACTAGTCCTACTCACCTGA
                                                         M  S  G  L

AGGCGAAAGCTCTTTGGATCCGCTGGCCGCTGAGTCTCGGAAACGCAAACTGCCCTGTGA
121   ------------+---------+---------+---------+---------+---------+ 180
      TCCGCTTTCGAGAAACCTAGGCGACCGGCGACTCAGAGCCTTTGCGTTTGACGGGACACT
       G  E  S  S  L  D  P  L  A  A  E  S  R  K  R  K  L  P  C  D

TGCCCCAGGACAGGGGCTTGTCTACAGTGGTGAGAAGTGGCCACGGGAGCAGGAGAGCAA
181   ------------+---------+---------+---------+---------+---------+ 240
      ACGGGGTCCTGTCCCCGAACAGATGTCACCACTCTTCACCGGTGCCCTCGTCCTCTCGTT
       A  P  G  Q  G  L  V  Y  S  G  E  K  W  R  R  E  Q  E  S  K

GTACATAGAGGAGCTGGCAGAGCTCATCTCTGCAAATCTCAGCGACATCGACAACTTCAA
241   ------------+---------+---------+---------+---------+---------+ 300
      CATGTATCTCCTCGACCGTCTCGAGTAGAGACGTTTAGAGTCGCTGTAGCTGTTGAAGTT
       Y  I  E  E  L  A  E  L  I  S  A  N  L  S  D  I  D  N  F  N
```

FIG. 1A

```
            TGTCAAGCCAGATAAATGTGCCATCCTAAAGGAGACAGTGAGACAGATACGGCAAATAAA
301      ---------+---------+---------+---------+---------+---------+  360
            ACAGTTCGGTCTATTTACACGGTAGGATTTCCTCTGTCACTCTGTCTATGCCGTTTATTT
             V  K  P  D  K  C  A  I  L  K  E  T  V  R  Q  I  R  Q  I  K  -

AGAACAAGGAAAAACTATTTCCAGTGATGATGATGTTCAAAAAGCTGATGTGTCTTCTAC
361      ---------+---------+---------+---------+---------+---------+  420
            TCTTGTTCCTTTTTGATAAAGGTCACTACTACTACAAGTTTTTCGACTACACAGAAGATG
             E  Q  G  K  T  I  S  S  D  D  D  V  Q  K  A  D  V  S  S  T  -

AGGGCAGGGAGTCATTGATAAAGACTCTTTAGGACCGCTTTTACTACAGGCAGTGGATGG
421      ---------+---------+---------+---------+---------+---------+  480
            TCCCGTCCCTCAGTAACTATTTCTGAGAAATCCTGGCGAAAATGATGTCCGTCACCTACC
             G  Q  G  V  I  D  K  D  S  L  G  P  L  L  L  Q  A  L  D  G  -

TTTCCTGTTTGTGGTGAATCGAGATGGAAACATTGTATTCGTGTCAGAAAATGTCACACA
481      ---------+---------+---------+---------+---------+---------+  540
            AAAGGACAAACACCACTTAGCTCTACCTTTGTAACATAAGCACAGTCTTTTACAGTGTGT
             F  L  F  V  V  N  R  D  G  N  I  V  F  V  S  E  N  V  T  Q  -

GTATCTGCAGTACAAGCAGGAGGACCTGGTTAACACAAGTGTCTACAGCATCTTACATGA
541      ---------+---------+---------+---------+---------+---------+  600
            CATAGACGTCATGTTCGTCCTCCTGGACCAATTGTGTTCACAGATGTCGTAGAATGTACT
             Y  L  Q  Y  K  Q  E  D  L  V  N  T  S  V  Y  S  I  L  H  E  -

GCCAAGACGGAAGGATTTCTTAAACACTTACCAAAATCCACAGTTAATGGAGTTTCTTGG
601      ---------+---------+---------+---------+---------+---------+  660
            CGGTTCTGCCTTCCTAAAGAATTTGTGAATGGTTTTAGGTGTCAATTACCTCAAAGAACC
             P  R  R  K  D  F  L  N  T  Y  Q  N  P  Q  L  M  E  F  L  G  -

ACTAATGAGAACCAGAGACAAAAAAGCCCCATACATTTTAATTGTCCGTATGTTGTGAA
661      ---------+---------+---------+---------+---------+---------+  720
```

AACACACGACATTTTGGAAGACGTGAATGCCAGTCCCGAAACGCGCCAGAGATATGAAAC
721   ------------+----------+----------+----------+----------+----------+   780
      TTGTGTGCTGTAAAACCTTCTGCACTTACGGTCAGGGCTTTGCGCGGTCTCTATACTTTG
       T   H   D   I   L   E   D   V   N   A   S   P   E   T   R   Q   R   Y   E   T   -

AATGCAGTGCTTTGCCCTGTCTCAGCCTCGCGCTATGCTGGAAGAAGGAGAAGACTTGCA
781   ------------+----------+----------+----------+----------+----------+   840
      TTACGTCACGAAACGGGACAGAGTCGGAGCGCGATACGACCTTCTTCCTCTTCTGAACGT
         M   Q   C   F   A   L   S   Q   P   R   A   M   L   E   E   G   E   D   L   Q   -

GTGCTGTATGATCTGCGTGGCTCGCCGCGTGACTGCGCCATTCCCATCCAGTCCCGAGAG
841   ------------+----------+----------+----------+----------+----------+   900
      CACGACATACTAGACGCACCGAGCGGCGCACTGACGCGGTAAGGGTAGGTCAGGGCTCTC
         C   C   M   I   C   V   A   R   R   V   T   A   P   F   P   S   S   P   E   S   -

CTTTATTACCAGACATGACCTTTCCGGAAAGGTTGTCAATATAGATACAAACTCACTTAG
901   ------------+----------+----------+----------+----------+----------+   960
      GAAATAATGGTCTGTACTGGAAAGGCCTTTCCAACAGTTATATCTATGTTTGAGTGAATC
         F   I   T   R   H   D   L   S   G   K   V   V   N   I   D   T   N   S   L   R   -

ATCTTCCATGAGGCCTGGCTTTGAAGACATAATCCGAAGATGTATCCAGAGGTTCTTCAG
961   ------------+----------+----------+----------+----------+----------+   1020
      TAGAAGGTACTCCGGACCGAAACTTCTGTATTAGGCTTCTACATAGGTCTCCAAGAAGTC
          S   S   M   R   P   G   F   E   D   I   I   R   R   C   I   Q   R   F   F   S   -

TCTGAATGATGGGCACTCATGGTCCCAGAAGCGTCACTATCAAGAAGCTTATGTTCATGG
1021  ------------+----------+----------+----------+----------+----------+   1080
      AGACTTACTACCCGTCAGTACCAGGGTCTTCGCAGTGATAGTTCTTCGAATACAAGTACC
```

CCACGCAGAGACCCCCGTGTATCGTTTCTCCTTGGCTGATGGAACTATTGTGAGTGCGCA
1081   ---------+---------+---------+---------+---------+---------+  1140
       GGTGCGTCTCTGGGGGCACATAGCAAAGAGGAACCGACTACCTTGATAACACTCACGCGT
        H  A  E  T  P  V  Y  R  F  S  L  A  D  G  T  I  V  S  A  Q  -

GACAAAAAGCAAACTCTTCCGCAATCCTGTAACGAATGATCGTCACGGCTTCATCTCGAC
1141   ---------+---------+---------+---------+---------+---------+  1200
       CTGTTTTTCGTTTGAGAAGGCGTTAGGACATTGCTTACTAGCAGTGCCGAAGTAGAGCTG
        T  K  S  K  L  F  R  N  P  V  T  N  D  R  H  G  F  I  S  T  -

CCACTTTCTTCAGAGAGAACAGAATGGATACAGACCAAACCCAATCCCGCAGGACAAAGG
1201   ---------+---------+---------+---------+---------+---------+  1260
       GGTGAAAGAAGTCTCTCTTGTCTTACCTATGTCTGGTTTGGGTTAGGGCGTCCTGTTTCC
        H  F  L  Q  R  E  Q  N  G  Y  R  P  N  I  P  Q  D  K  G  -

CATCCGACCTCCTGCAGCAGGGTGTGGCGTGAGCATGTCTCCAAATCAGAATGTACAGAT
1261   ---------+---------+---------+---------+---------+---------+  1320
       GTAGGCTGGAGGACGTCGTCCCACACCGCACTCGTACAGAGGTTTAGTCTTACATGTCTA
        I  R  P  P  A  A  G  C  G  V  S  M  S  P  N  Q  N  V  Q  M  -

GATGGGCAGCCGGACCTATGGCGTGCCAGACCCCAGCAACACAGGGCAGATGGGTGGAGC
1321   ---------+---------+---------+---------+---------+---------+  1380
       CTACCCGTCGGCCTGGATACCGCACGGTCTGGGGTCGTTGTGTCCCGTCTACCCACCTCG
        M  G  S  R  T  Y  G  V  P  D  P  S  N  T  G  Q  M  G  G  A  -
```

FIG. 1D

```
             TAGGTACGGGGCTTCTAGTAGCGTAGCCTCACTGACGCCAGGACAAAGCCTACAGTCGCC
1381   ---------+---------+---------+---------+---------+---------+  1440
             ATCCASTGCCCCGAAGATCATCGATCGGAGTGACTGCGGTCCTGTTTCGGATGTCAGCGG
              R   Y   G   A   S   S   S   V   A   S   L   T   P   G   Q   S   L   Q   S   P   -

ATCTTCCTATCAGAACAGCAGCTATGGGCTCAGCATGAGCAGTCCCCCCCACGGCAGTCC
1441   ---------+---------+---------+---------+---------+---------+  1500
             TAGAAGGATAGTCTTGTCGTCGATACCCGAGTCGTACTCGTCAGGGGGGGTGCCGTCAGC
              S   S   Y   Q   N   S   S   Y   G   L   S   M   S   S   P   P   H   G   S   P   -

TGGTCTTGGCCCCAACCAGCAGAACATCATGATTTCCCCTCGGAATCGTGGCAGCCCAAA
1501   ---------+---------+---------+---------+---------+---------+  1560
             ACCAGAACCGGGGTTGGTCGTCTTGTAGTACTAAAGGGGAGCCTTAGCACCGTCGGGTTT
              G   L   G   P   N   Q   Q   N   I   M   I   S   P   R   N   R   G   S   P   K   -

GATGGCCTCCCACCAGTTCTCTCCTGCTGCAGGTGCACACTCACCCATGGGACCTTCTGG
1561   ---------+---------+---------+---------+---------+---------+  1620
             CTACCGGAGGGTGGTCAAGAGAGGACGACGTCCACGTGTGAGTGGGTACCCTGGAAGACC
              M   A   S   H   Q   F   S   P   A   A   G   A   H   S   P   M   G   P   S   G   -
             CAACACAGGGAGCCACAGCTTTTCTAGCAGCTCCCTCAGTGCCTTGCAAGCCATCAGTGA
1621   ---------+---------+---------+---------+---------+---------+  1680
             GTTGTGTCCCTCGGTGTCGAAAAGATCGTCGAGGGACTCACGGAACGTTCGGTAGTCACT
              N   T   G   S   H   S   F   S   S   S   S   L   S   A   L   Q   A   I   S   E   -
             AGGCGTGGGGACCTCTCTTTTATCTACTCTGTCCTCACCAGGCCCCAAACTGGATAATTC
1681   ---------+---------+---------+---------+---------+---------+  1740
             TCCGCACCCCTGGAGAGAAAATAGATGAGACAGGAGTGGTCCGGGGTTTGACCTATTAAG
              G   V   G   T   S   L   L   S   T   L   S   S   P   G   P   K   L   D   N   S   -

TCCCAATATGAATATAAGCCAGCCAAGTAAAGTGAGTGGTCAGGACTNTAAGAGCCCCCT
1741   ---------+---------+---------+---------+---------+---------+  1800
             AGGGTTATACTTATATTCGGTCGGTTCATTTCACTCACCAGTCCTGANATTCTCGGGGGA
              P   N   M   N   I   S   Q   P   S   K   V   S   G   Q   D   ?   K   S   P   L   -
```

FIG. 1E

```
         AGGCTTATACTGTGAACAGAATCCAGTGGAGAGTTCAGTGTGTCAGTCAAACAGCAGAGA
1801     ---------+---------+---------+---------+---------+---------+ 1860
         TCCGAATATGACACTTGTCTTAGGTCACCTCTCAAGTCACACAGTCAGTTTGTCGTCTCT
           G  L  Y  C  E  Q  N  P  V  E  S  S  V  C  Q  S  N  S  R  D  -

TCCCCAAGTGAAAAAAGAAAGCAAGGAGAGCAGTGGGGAGGTGTCAGAGACGCCCAGGGG
1861     ---------+---------+---------+---------+---------+---------+ 1920
         AGGGGTTCACTTTTTTCTTTCGTTCCTCTCGTCACCCCTCCACAGTCTCTGCGGGTCCCC
           P  Q  V  K  K  E  S  K  E  S  S  G  E  V  S  E  T  P  R  G  -

ACCTCTGGAAAGCAAAGGCCACAAGAAACTGCTGCAGTTACTCACGTGCTCCTCCGACGA
1921     ---------+---------+---------+---------+---------+---------+ 1980
         TGGAGACCTTTCGTTTCCGGTGTTCTTTGACGACGTCAATGAGTGCACGAGGAGGCTGCT
           P  L  E  S  K  G  H  K  K  L  L  Q  L  L  T  C  S  S  D  D  -

CCGAGGCCATTCCTCCTTGACCAACTCTCCCCTGGATCCAAACTGCAAAGACTCTTCCGT
1981     ---------+---------+---------+---------+---------+---------+ 2040
         GGCTCCGGTAAGGAGGAACTGGTTGAGAGGGGACCTAGGTTTGACGTTTCTGAGAAGGCA
           R  G  H  S  S  L  T  N  S  P  L  D  P  N  C  K  D  S  S  V  -

TAGTGTCACCAGCCCCTCTGGAGTGTCCTCCTCAACATCAGGGACAGTGTGTTCCACCTC
2041     ---------+---------+---------+---------+---------+---------+ 2100
         ATCACAGTGGTCGGGGAGACCTCACAGGAGGAGTTGTAGTCCCTGTCACAGAAGGTGGAG
             S  V  T  S  P  S  G  V  S  S  S  T  S  G  T  V  S  S  T  S  -

CAATGTGCATGGGTCTCTGTTGCAAGAGAAACACCGGATTTTGCACAAGTTGCTGCAGAA
2101     ---------+---------+---------+---------+---------+---------+ 2160
         GTTACACGTACCCAGAGACAACGTTCTCTTTGTGGCCTAAAACGTGTTCAACGACGTCTT
           N  V  H  G  S  L  L  Q  E  K  H  R  I  L  H  K  L  L  Q  N  -
```

FIG. 1F

```
         TGGCAACTCCCCAGCGGAGGTCGCCAAGATCACTGCAGAGGCCACTGGGAAGGACACGAG
2161  ---------+---------+---------+---------+---------+---------+ 2220
         ACCGTTGAGGGGTCGCCTCCAGCGGTTCTAGTGACGTCTCCGGTGACCCTTCCTGTGCTC
          G  N  S  P  A  E  V  A  K  I  T  A  E  A  T  G  K  D  T  S  -
         CAGCACTGCTTCCTGTGGAGAGGGGACAACCAGGCAGGAGCAGCTGAGTCCTAAGAAGAA
2221  ---------+---------+---------+---------+---------+---------+ 2280
         GTCGTGACGAAGGACACCTCTCCCCTGTTGGTCCGTCCTCGTCGACTCAGGATTCTTCTT
          S  T  A  S  C  G  E  G  T  T  R  Q  E  Q  L  S  P  K  K  K  -

GGAGAATAATGCTCTGCTTAGATACCTGCTGGACAGGGATGACCCCAGTGATGTGCTTGC
2281  ---------+---------+---------+---------+---------+---------+ 2340
         CCTCTTATTACGAGACGAATCTATGGACGACCTGTCCCTACTGGGGTCACTACACGAACG
          E  N  N  A  L  L  R  Y  L  L  D  R  D  D  P  S  D  V  L  A  -
         CAAAGAGCTGCAGCCCCAGGCCGACAGTGGGGACAGTAAACTGAGTCAGTGCAGCTGCTC
2341  ---------+---------+---------+---------+---------+---------+ 2400
         GTTTCTCGACGTCGGGGTCCGGCTGTCACCCCTGTCATTTGACTCAGTCACGTCGACGAG
          K  E  L  Q  P  Q  A  D  S  G  D  S  K  L  S  Q  C  S  C  S  -

CACCAATCCCAGCTCTGGCCAAGAGAAAGACCCCAAAATTAAGACCGAGACGAACGACGA
2401  ---------+---------+---------+---------+---------+---------+ 2460
         GTGGTTAGGGTCGAGACCGGTTCTCTTTCTGGGGTTTTAATTCTGGCTCTGCTTGCTGCT
          T  N  P  S  S  G  Q  E  K  D  P  K  I  K  T  E  T  N  D  E  -

GGTATCGGGAGACCTGGATAATCTAGATGCCATTCTTGGAGATTTGACCAGTTCTGACTT
2461  ---------+---------+---------+---------+---------+---------+ 2520
         CCATAGCCCTCTGGACCTATTAGATCTACGGTAAGAACCTCTAAACTGGTCAAGACTGAA
          V  S  G  D  L  D  N  L  D  A  I  L  G  D  L  T  S  S  D  F  -

CTACAACAATCCTACAAATGGCGGTCACCCAGGGGCCAAACAGCAGATGTTTGCAGGACC
2521  ---------+---------+---------+---------+---------+---------+ 2580
```

GAGTTCTCTGGGTTTGCGAAGTCCACAGCCTGTGCAGTCTGTTCGTCCTCCATATAACCG
2581    ---------+---------+---------+---------+---------+---------+  2640
        CTCAAGAGACCCAAACGCTTCAGGTGTCGGACACGTCAGACAAGCAGGAGGTATATTGGC
          S  S  L  G  L  R  S  P  Q  P  V  Q  S  V  R  P  P  Y  N  R

AGCGGTGTCTCTGGATAGCCCTGTGTCTGTTGGCTCAGGTCCGCCAGTGAAGAATGTCAG
2641    ---------+---------+---------+---------+---------+---------+  2700
        TCGCCACAGAGACCTATCGGGACACAGACAACCGAGTCCAGGCGGTCACTTCTTACAGTC
          A  V  S  L  D  S  P  V  S  V  G  S  G  P  P  V  K  N  V  S -

TGCTTTCCCTGGGTTACCAAAACAGCCCATACTGGCTGGGAATCCAAGAATGATGGATAG
2701    ---------+---------+---------+---------+---------+---------+  2760
        ACGAAAGGGACCCAATGGTTTTGTCGGGTATGACCGACCCTTAGGTTCTTACTACCTATC
          A  F  P  G  L  P  K  Q  P  I  L  A  G  N  P  R  M  M  D  S -

TCAGGAGAATTACGGTGCCAACATGGGCCCAAACAGAAATGTTCCTGTGAATCCGACTTC
2761    ---------+---------+---------+---------+---------+---------+  2820
        AGTCCTCTTAATGCCACGGTTGTACCCGGGTTTGTCTTTACAAGGACACTTAGGCTGAAG
          Q  E  N  Y  G  A  N  M  G  P  N  R  N  V  P  V  N  P  T  S -

CTCCCCCGGAGACTGGGGCTTAGCTAACTCAAGGGCCAGCAGAATGGAGCCTCTGGCATC
2821    ---------+---------+---------+---------+---------+---------+  2880
        GAGGGGGCCTCTGACCCCGAATCGATTGAGTTCCCGGTCGTCTTACCTCGGAGACCGTAG
          S  P  G  D  W  G  L  A  N  S  R  A  S  R  M  E  P  L  A  S -
```

FIG. 1H

```
             AAGTCCCCTGGGAAGAACTGGAGCCGATTACAGTGCCACTTTACCCAGACCTGCCATGGG
     2881    ------------------------------------------------------------  2940
             TTCAGGGGACCCTTCTTGACCTCGGCTAATGTCACGGTGAAATGGGTCTGGACGGTACCC
              S  P  L  G  R  T  G  A  D  Y  S  A  T  L  P  R  P  A  M  G  -
             GGGCTCTGTGCCTACCTTGCCACTTCGTTCTAATCGACTGCCAGGTGCAAGACCATCGTT
     2941    ------------------------------------------------------------  3000
             CCCGAGACACGGATGGAACGGTGAAGCAAGATTAGCTGACGGTCCACGTTCTGGTAGCAA
              G  S  V  P  T  L  P  L  R  S  N  R  L  P  G  A  R  P  S  L  -

GCAGCAACAGCAGCAGCAACAGCAGCAACAGCAACAACAACAGCAGCAACAGCAGCAGCA
     3001    ------------------------------------------------------------  3060
             CGTCGTTGTCGTCGTCGTTGTCGTCGTTGTCGTTGTTGTTGTCGTCGTTGTCGTCGTCGT
              Q  Q  Q  Q  Q  Q  Q  Q  Q  Q  Q  Q  Q  Q  Q  Q  Q  Q  Q  Q  -

ACAGCAGCAGATGCTTCAAATGAGAACTGGTGAGATTCCCATGGGAATGGGAGTCAATCC
     3061    ------------------------------------------------------------  3120
             TGTCGTCGTCTACGAAGTTTACTCTTGACCACTCTAAGGGTACCCTTACCCTCAGTTAGG
              Q  Q  Q  M  L  Q  M  R  T  G  E  I  P  M  G  M  G  V  N  P  -

NTATAGCCCAGCAGTGCAGTCTAACCAACCAGGTTCCTGGCCAGAGGGCATGCTCTCTAT
     3121    ------------------------------------------------------------  3180
             NATATCGGGTCGTCACGTCAGATTGGTTGGTCCAAGGACCGGTCTCCCGTACGAGAGATA
              Y  S  P  A  V  Q  S  N  Q  P  G  S  W  P  E  G  M  L  S  M  -

GGAACAAGGTCCTCACGGGTCTCAAAATAGGCCTCTTCTTAGAAACTCTCTGGATGATCT
     3181    ------------------------------------------------------------  3240
             CCTTGTTCCAGGAGTGCCCAGAGTTTTATCCGGAGAAGAATCTTTGAGAGACCTACTAGA
              E  Q  G  P  H  G  S  Q  N  R  P  L  L  R  N  S  L  D  D  L

GCTTGGGCCACCTTCTAACGCAGAGGGCCAGAGTGACGAGAGAGCTCTGCTGGACCAGCT
     3241    ------------------------------------------------------------  3300
             CGAACCCGGTGGAAGATTGCGTCTCCCGGTCTCACTGCTCTCTCGAGACGACCTGGTCGA
              L  G  P  P  S  N  A  E  G  Q  S  D  E  R  A  L  L  D  Q  L
```

FIG. 1I

```
          GCACACATTCCTGAGCAACACAGATGCCACAGGTCTGGAGGAGATCGACAGGGCCTTGGG
3301      ------------+---------+---------+---------+---------+---------+  3360
          CGTGTGTAAGGACTCGTTGTGTCTACGGTGTCCAGACCTCCTCTAGCTGTCCCGGAACCC
           H  T  F  L  S  N  T  D  A  T  G  L  E  E  I  D  R  A  L  G

AATTCCTGAGCTCGTGAATCAGGGACAAGCTTTGGAGTCCAAACAGGATGTTTTCCAAGG
3361      ------------+---------+---------+---------+---------+---------+  3420
          TTAAGGACTCGAGCACTTAGTCCCTGTTCGAAACCTCAGGTTTGTCCTACAAAAGGTTCC
           I  P  E  L  V  N  Q  G  Q  A  L  E  S  K  Q  D  V  F  Q  G  -

CCAAGAAGCAGCAGTAATGATGGATCAGAAGGCTGCACTATATGGACAGACATACCCAGC
3421      ------------+---------+---------+---------+---------+---------+  3480
          GGTTCTTCGTCGTCATTACTACCTAGTCTTCCGACGTGATATACCTGTCTGTATGGGTCG
           Q  E  A  A  V  M  M  D  Q  K  A  A  L  Y  G  Q  T  Y  P  A  -

TCAGGGTCCTCCCCTTCAAGGAGGCTTTAACCTTCAGGGACAGTCACCATCGTTTAACTC
3481      ------------+---------+---------+---------+---------+---------+  3540
          AGTCCCAGGAGGGGAAGTTCCTCCGAAATTGGAAGTCCCTGTCAGTGGTAGCAAATTGAG
           Q  G  P  P  L  Q  G  G  F  N  L  Q  G  Q  S  P  S  F  N  S  -

TATGATGGGTCAGATTAGCCAGCAAGGCAGCTTTCCTCTGCAAGGCATGCATCCTAGAGC
3541      ------------+---------+---------+---------+---------+---------+  3600
          ATACTACCCAGTCTAATCGGTCGTTCCGTCGAAAGGAGACGTTCCGTACGTAGGATCTCG
           M  M  G  Q  I  S  Q  Q  G  S  F  P  L  Q  G  M  H  P  R  A  -

CGGCCTCGTGAGACCAAGGACCAACACCCCGAAGCAGCTGAGAATGCAGCTTCAGCAGAG
3601      ------------+---------+---------+---------+---------+---------+  3660
          GCCGGAGCACTCTGGTTCCTGGTTGTGGGGCTTCGTCGACTCTTACGTCGAAGTCGTCTC
           G  L  V  R  P  R  T  N  T  P  K  Q  L  R  M  Q  L  Q  Q  R  -
```

FIG. 1J

```
              GCTACAGGGCCAGCAGTTTTTAAATCAGAGCCGGCAGGCACTTGAAATGAAAATGGAGAA
  3661        ------------+----------+----------+----------+----------+----------+  3720
              CGATGTCCCGGTCGTCAAAAATTTAGTCTCGGCCGTCCGTGAACTTTACTTTTACCTCTT
                L  Q  G  Q  Q  F  L  N  Q  S  R  Q  A  L  E  M  K  M  E  N

CCCTGCTGGCACTGCTGTGATGAGGCCCATGATGCCCCAGGCTTTCTTTAATGCCCAAAT
  3721        ------------+----------+----------+----------+----------+----------+  3780
              GGGACGACCGTGACGACACTACTCCGGGTACTACGGGGTCCGAAAGAAATTACGGGTTTA
                P  A  G  T  A  V  M  R  P  M  M  P  Q  A  F  F  N  A  Q  M  -

GGCTGCCCAGCAGAAACGAGAGCTGATGAGCCATCACCTGCAGCAGCAGAGGATGGCGAT
  3781        ------------+----------+----------+----------+----------+----------+  3840
              CCGACGGGTCGTCTTTGCTCTCGACTACTCGGTAGTGGACGTCGTCGTCTCCTACCGCTA
                A  A  Q  Q  K  R  E  L  M  S  H  H  L  Q  Q  Q  R  M  A  M  -

GATGATGTCACAACCACAGCCTCAGGCCTTCAGCCCACCTCCCAACGTCACCGCCTCCCC
  3841        ------------+----------+----------+----------+----------+----------+  3900
              CTACTACAGTGTTGGTGTCGGAGTCCGGAAGTCGGGTGGAGGGTTGCAGTGGCGGAGGGG
                M  M  S  Y  P  Y  P  Q  A  F  S  P  P  P  N  V  T  A  S  P  -

CAGCATGGACGGGGTTTTGGCAGGTTCAGCAATGCCGCAAGCCCCTCCACAACAGTTTCC
  3901        ------------+----------+----------+----------+----------+----------+
              GTCGTACCTGCCCCAAAACCGTCCAAGTCGTTACGGCGTTCGGGGAGGTGTTGTCAAAGG
                S  M  D  G  V  L  A  G  S  A  M  P  Q  A  P  P  Q  Q  F  P  -

ATATCCAGCAAATTACGGAACGGGACAACCACCAGTAGCCAGCCTTTGGTCGAGGCTCGA
  3961        ------------+----------+----------+----------+----------+----------+  4020
              TATAGGTCGTTTAATGCCTTGCCCTGTTGGTGGTCATCGGTCGGAAACCAGCTCCGAGCT
                Y  P  A  N  Y  G  T  G  Q  P  P  V  A  S  L  W  S  R  L  E  -

GTCCTCCCAGTGCAATGATGTCATCAAGAATGGGGCCTTCCCAGAATGCCATGGTGCAGC
  4021        ------------+----------+----------+----------+----------+----------+  4080
              CAGGAGGGTCACGTTACTACAGTAGTTCTTACCCCGGAAGGGTCTTACGGTACCACGTCG
                S  S  Q  C  N  D  V  I  K  N  G  A  F  P  E  C  H  G  A  A  -
```

FIG. 1K

```
            ATCCTCAGCCCACACCCATGTATCAGCCTTCAGATATGAAGGGGTGGCCGTCAGGGAACC
4081  ---------+---------+---------+---------+---------+---------+ 4140
            TAGGAGTCGGGTGTGGGTACATAGTCGGAAGTCTATACTTCCCCACCGGCAGTCCCTTGG
             S  S  A  H  T  H  V  S  A  F  R  Y  E  G  V  A  V  R  E  P

TGGCCAGGAATGGCTCCTTCCCCCAGCAGCAGTTTGCTCCCCAGGGGAACCCTGCAGCCT
4141  ---------+---------+---------+---------+---------+---------+ 4200
            ACCGGTCCTTACCGAGGAAGGGGGTCGTCGTCAAACGAGGGGTCCCCTTGGGACGTCGGA
             G  Q  E  W  L  L  P  P  A  A  V  C  S  P  G  E  P  C  S  L

ACAACATGGTGCATATGAACAGCAGCGGTGGGCACTTGGGACAGATGGCCATGACCCCCA
4201  ---------+---------+---------+---------+---------+---------+ 4260
            TGTTGTACCACGTATACTTGTCGTCGCCACCCGTGAACCCTGTCTACCGGTACTGGGGGT
             Q  H  G  A  Y  E  Q  Q  R  W  A  L  G  T  D  G  H  D  P  H  -

TGCCCATGTCTGGCATGCCCATGGGCCCCGATCAGAAATACTGCTGACATCTCCCTAGTG
4261  ---------+---------+---------+---------+---------+---------+ 4320
            ACGGGTACAGACCGTACGGGTACCCGGGGCTAGTCTTTATGACGACTGTAGAGGGATCAC
             A  H  V  W  H  A  H  G  P  R  S  E  I  L  L  T  S  P  *

GGACTGACTGTACAGATGACACTGCACAGGATCATCAGGACGTGGCGGCGAGTCATTGTC
4321  ---------+---------+---------+---------+---------+---------+ 4380
            CCTGACTGACATGTCTACTGTGACGTGTCCTAGTAGTCCTGCACCGCCGCTCAGTAACAG

TAAGCATCCAGCTTGGAAGCAAGGCCAGCGTGACCAGCAGCGGGGTCTGTGCTGTCATTT
4381  ---------+---------+---------+---------+---------+---------+ 4440
            ATTCGTAGGTCGAACCTTCGTTCCGGTCGCACTGGTCGTCGCCCCAGACACGACAGTAAA

GAGCAGAGCTGGGTCTCGCTGAAGCGCACTGTCTACCTGATGCCCTGCCTCTGTGTGGCA
4441  ---------+---------+---------+---------+---------+---------+ 4500
```

FIG. 1L

```
            AGGTGTTCTGCCTCATGAGGATGTGATTCTGGAGATGGGGTGTTCGTAAGCACCGCTCTC
4501        ------------+---------+---------+---------+---------+---------+ 4560
            TCCACAAGACGGAGTACTCCTACACTAAGACCTCTACCCCACAAGCATTCGTGGCGAGAG

TTACGTCACTCCCTTCTGCCTCGCCAGCCAAAGTCTTCACGTAGATCTAGATGGCTAGGG
4561        ---------+---------+---------+---------+---------+---------+ 4620
            AATGCAGTGAGGGAAGACGGAGCGGTCGGTTTCAGAAGTGCATCTAGATCTACCGATCCC

TTTCTGTCTTGCAGCACTGGACGAGGGGGCACACTCTGCCTTCTCGCGTGTCGTCAGCAA
4621        ---------+---------+---------+---------+---------+---------+ 4680
            AAAGACAGAACGTCGTGACCTGCTCCCCCGTGTCAGACGGAAGAGCGCACAGCAGTCGTT

GTTAGTTCGTGTCGCTCTCCTGTCCAGTGCAATCAGTGTTTCTGCGCTCTTGTCCTTTAC
4681        ---------+---------+---------+---------+---------+---------+ 4740
            CAATCAAGCACAGCGAGAGGACAGGTCACGTTAGTCACAAAGACGCGAGAACAGGAAATG

AGGTGTAATCCCCAAGTCTGTCGTCCTAGTCTCTCCTGGTGAAGTCCCCGTACCTGTAAT
4741        ---------+---------+---------+---------+---------+---------+ 4800
            TCCACATTAGGGGTTCAGACAGCAGGATCAGAGAGGACCACTTCAGGGGCATGGACATTA

CTCAACAATTCTCATTGAAGTTTAAATGGCTTTTGAAAAAAGGGAAAAATGAAAATGGCA
4801        ---------+---------+---------+---------+---------+---------+
```

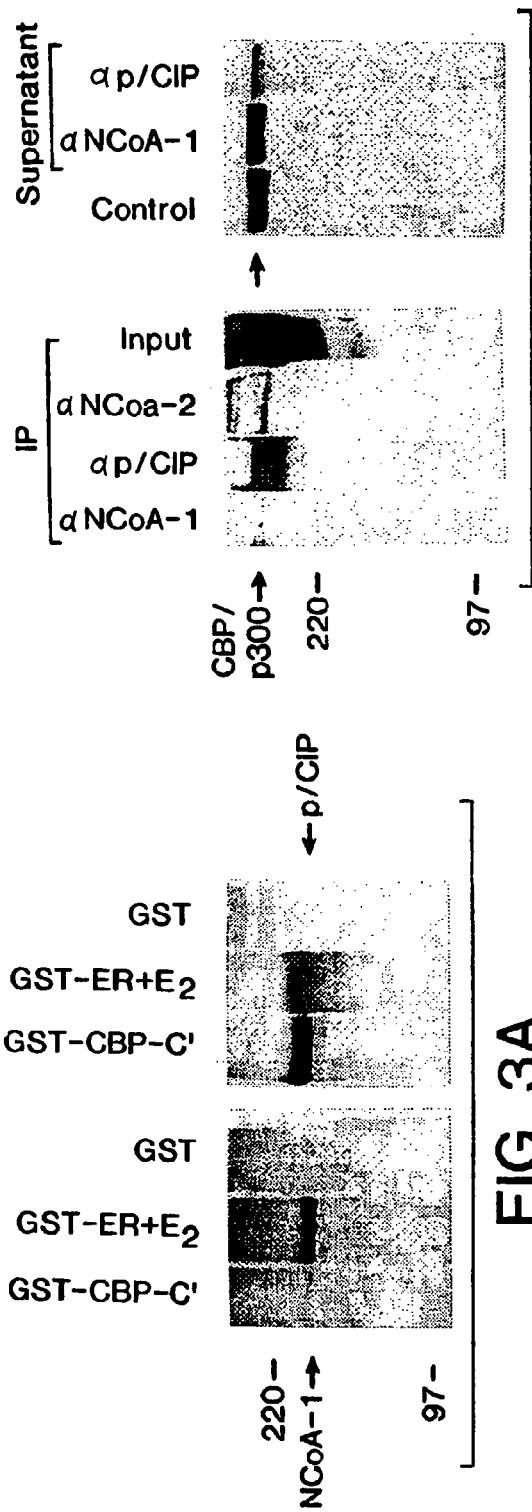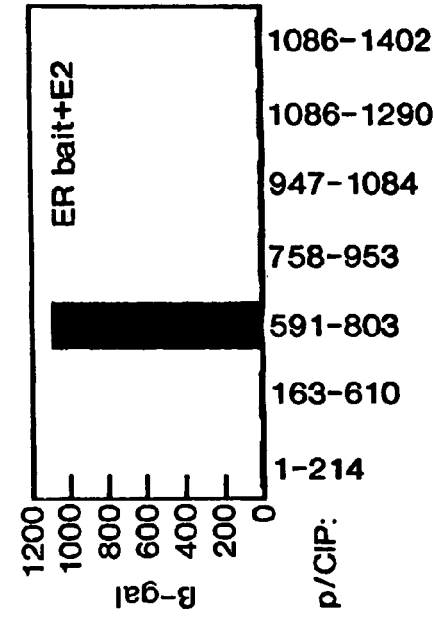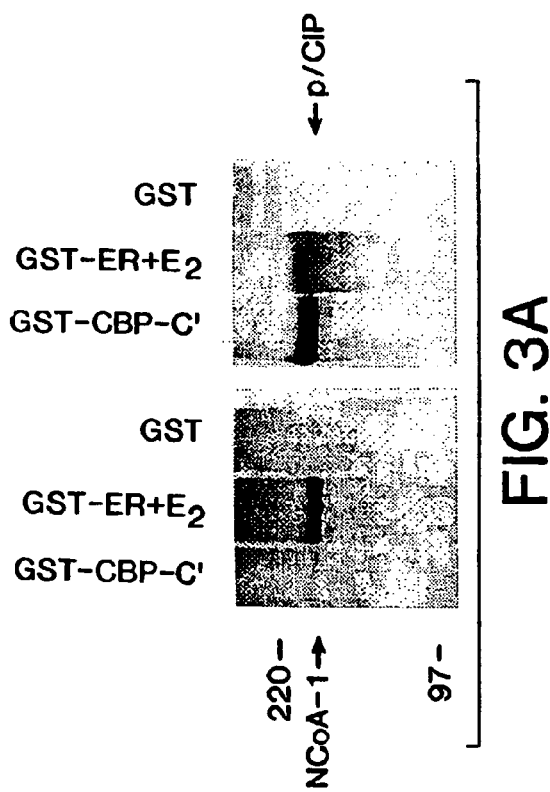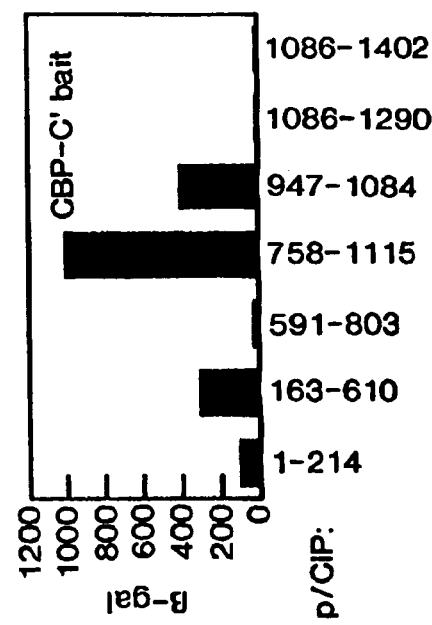
FIG. 3A
FIG. 3B
FIG. 3C-1
FIG. 3C-2

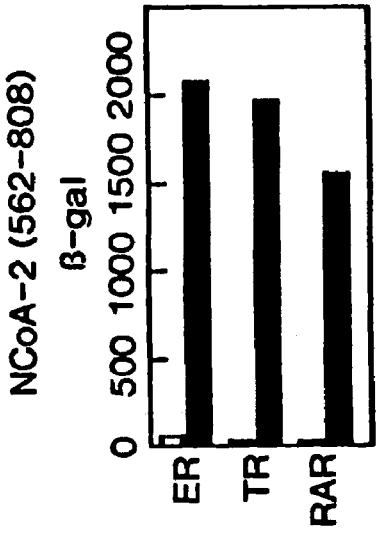
FIG. 3D-1
FIG. 3D-2
FIG. 3D-3
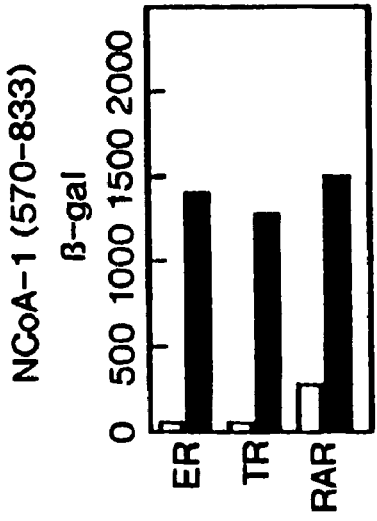
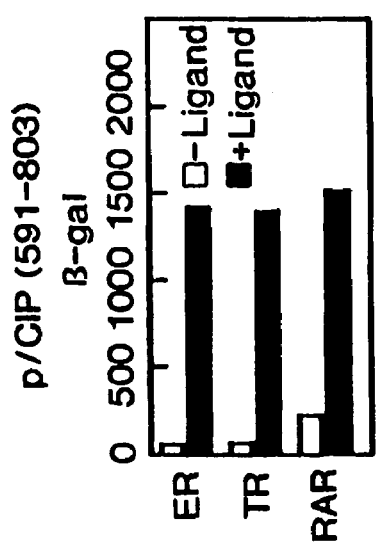
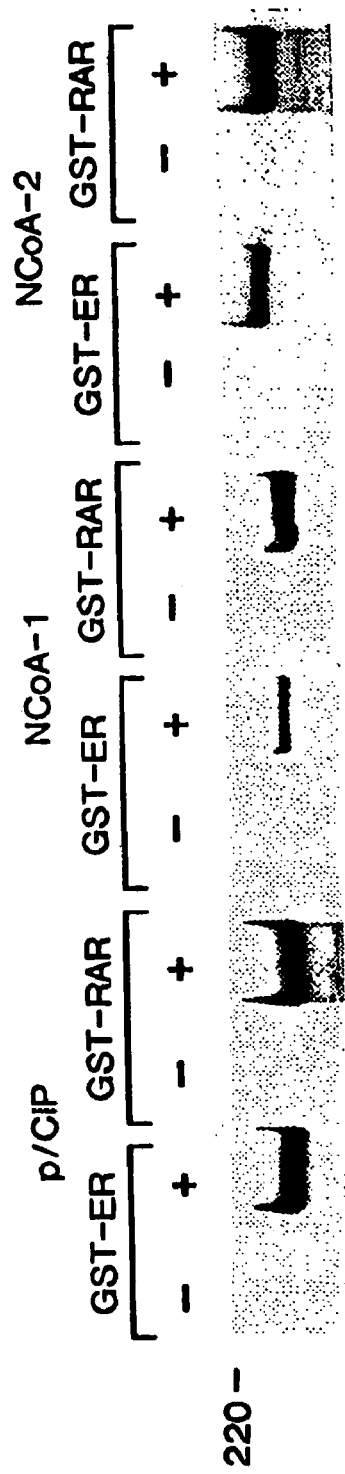
FIG. 3E

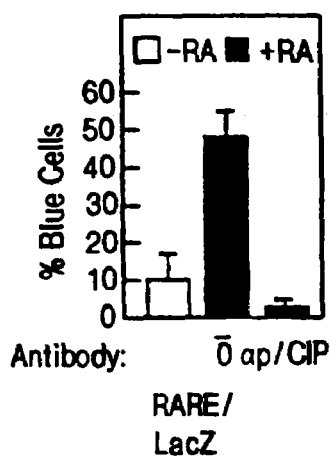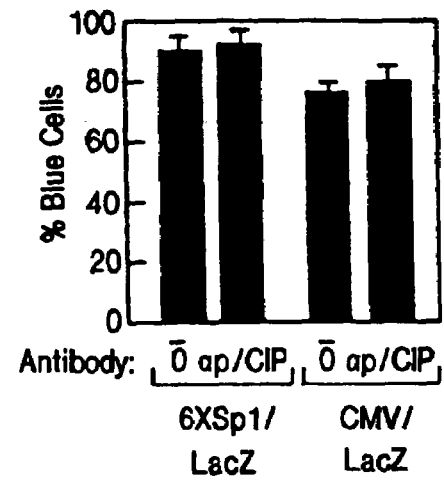
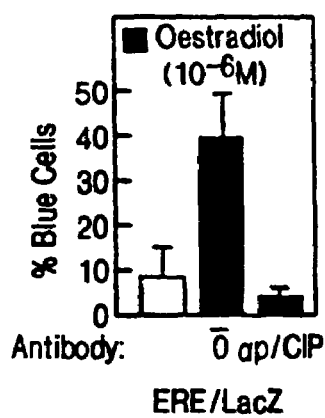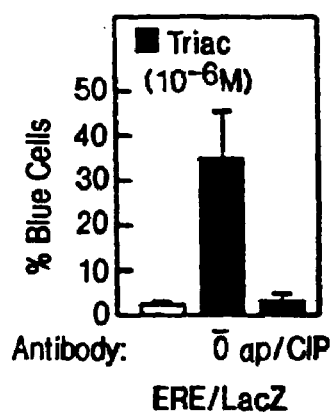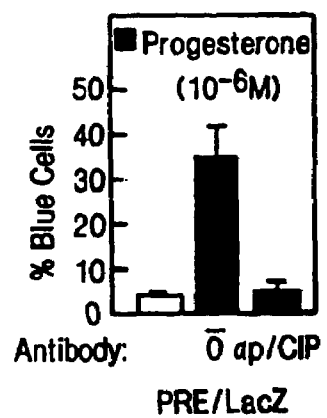
FIG. 4A-1  FIG. 4A-2
FIG. 4B-1  FIG. 4B-2  FIG. 4B-3

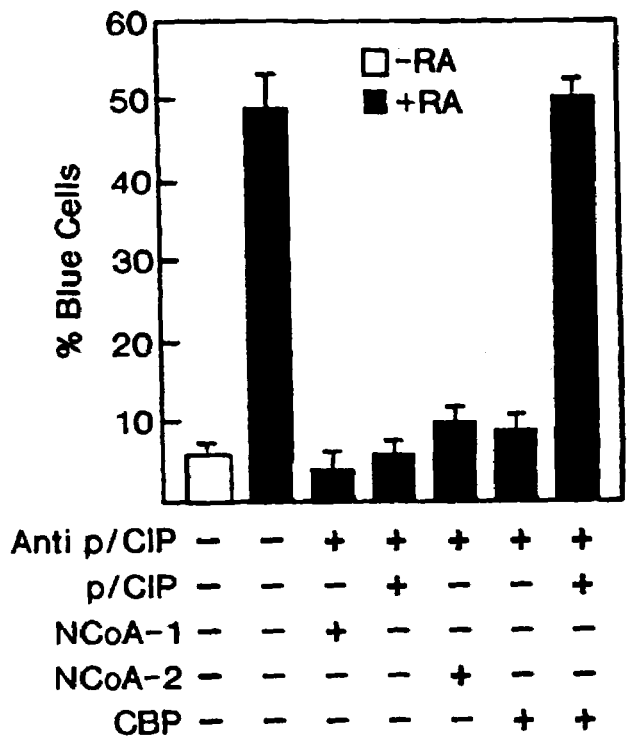
FIG. 4C
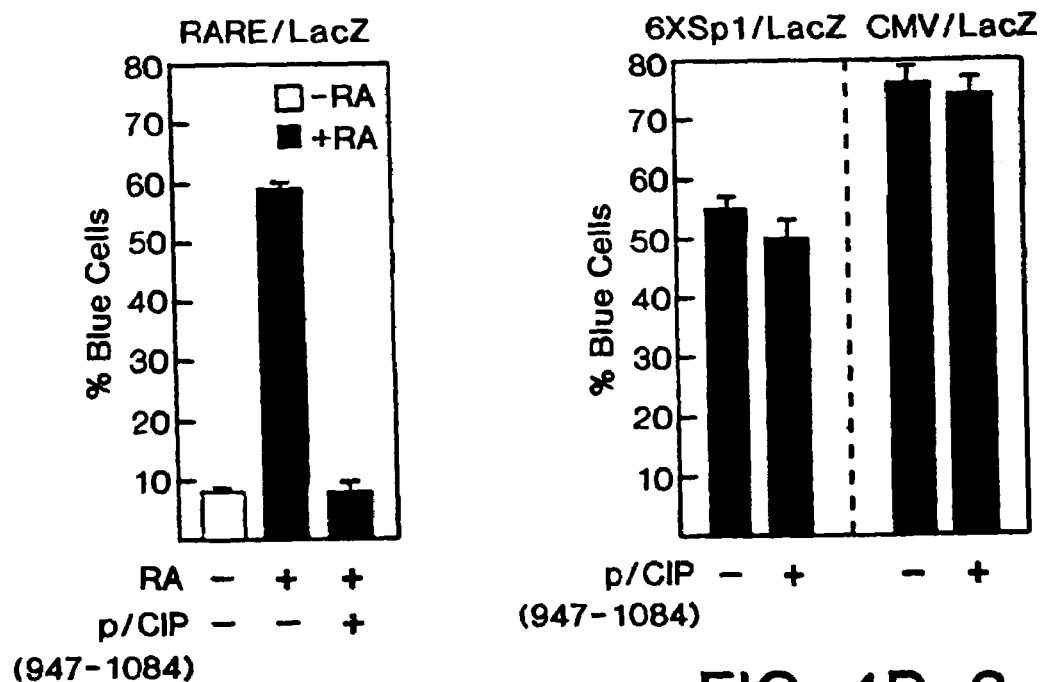
FIG. 4D-1
FIG. 4D-2

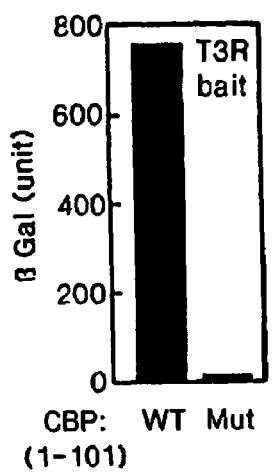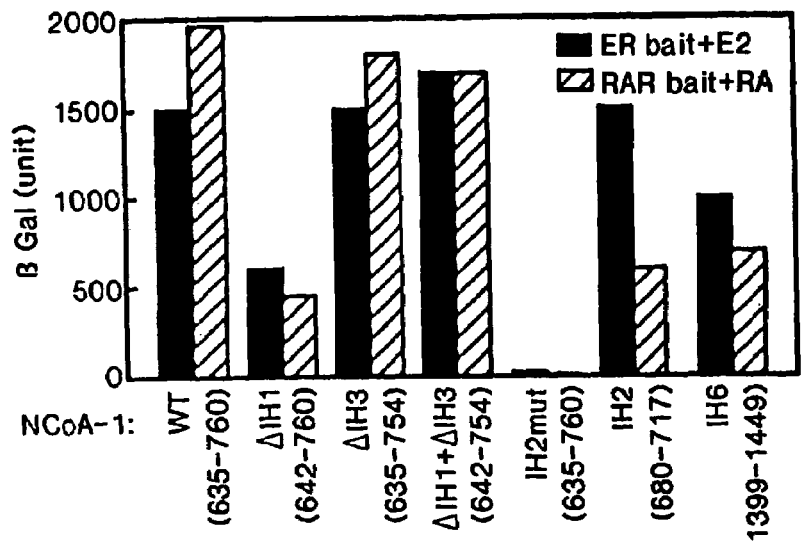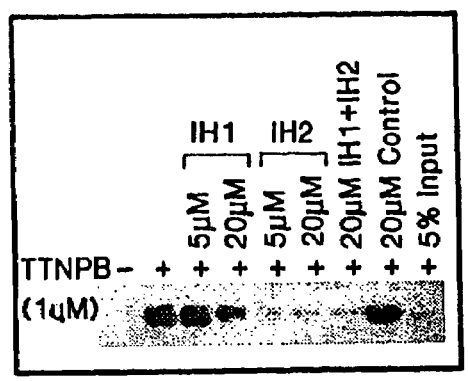
FIG. 6B
FIG. 6C-1
FIG. 6C-2

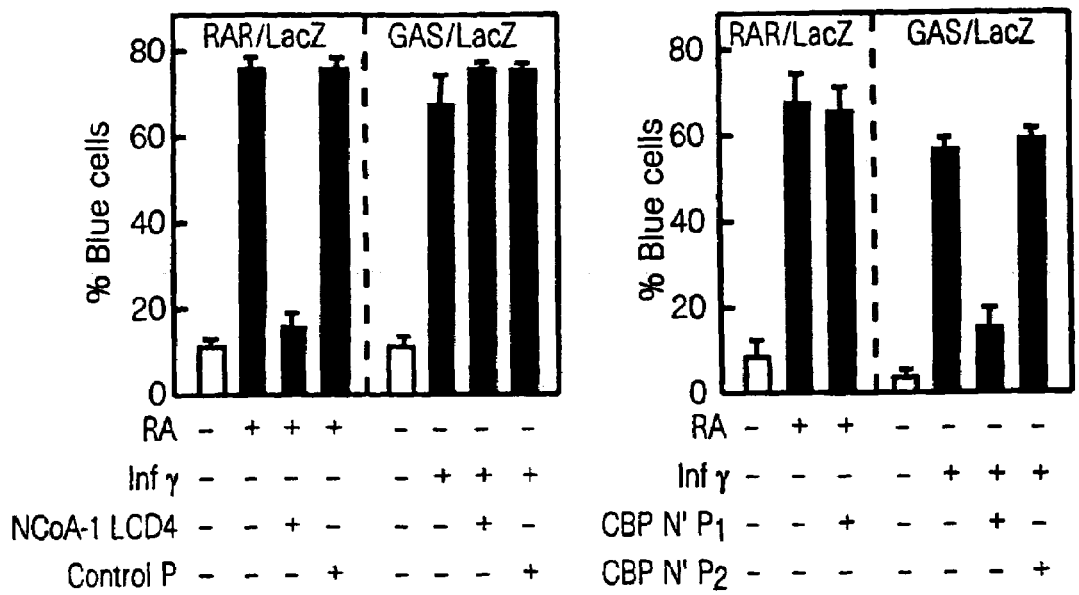
FIG. 7A
FIG. 7B
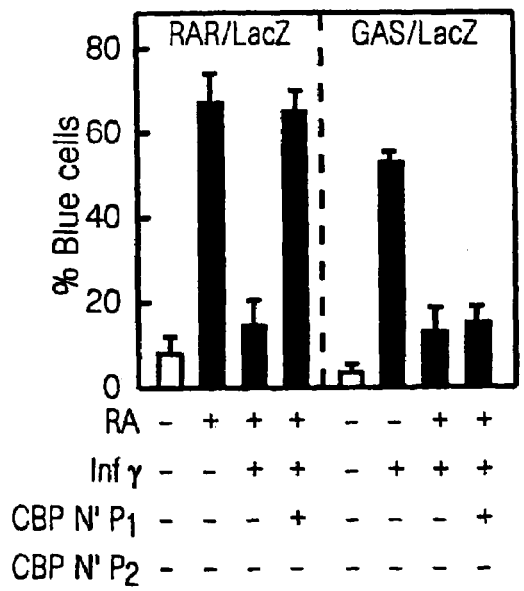
FIG. 7C

TRANSCRIPTION FACTOR COACTIVATOR PROTEIN, P/CIP

This application is a divisional application of U.S. application Ser. No. 09/445,353 filed May 5, 2000, now U.S. Pat. No. 6,812,336, which was the National of International Application No. PCT/US98/12263, filed Jun. 12, 1998, which claims the benefit of U.S. Provisional Application No. 60/049,452, filed Jun. 12, 1997, the entire content of which are herein incorporated by reference.

ACKNOWLEDGMENT

This invention was made with government support under grant number DK39949-14A1 awarded by the National Institutes of Health and grant number CA52599-07 awarded by the National Cancer Institute. The government has certain rights in the invention.

SEQUENCE LISTING

A sequence listing appendix is submitted under 1.821(c) and is incorporated herein by reference.

BACKGROUND OF THE INVENTION

1. Field of the Invention

The present invention relates generally to molecular biology and biochemistry and more specifically to a coactivator protein, p/CIP, which is involved in regulating gene expression by CBP/p300-dependent transcription factors, and to methods of using the coactivator protein to selectively regulate gene expression.

2. Background Information

Regulation of gene expression is mediated by sequence-specific transcription factors that bind to target genes and activate or repress transcription. Many of these factors are controlled by extracellular signals that switch the factors between inactive and active states. Such signals can result in post-translational modification as observed, for example, with the members of the STAT family of transcription factors, or can result in ligand-induced conformational changes as observed, for example, with members of the nuclear receptor family of transcription factors.

Coactivator proteins have been identified that are recruited to the active forms of such transcription factors and are required for their transcriptional effects. The coactivators, CBP and p300, for example, serve essential roles in transcriptional activation by several classes of regulated transcription factors, including nuclear receptors, STAT factors, AP-1 proteins, NF-κB and CREB. In addition, a more recently discovered family of proteins, termed nuclear receptor coactivator (NCoA) proteins, can interact with various nuclear receptors in a ligand-dependent manner and also can interact with CBP and p300.

Two members of the NCoA family of proteins, NCoA-1 and NCoA-2, appear to have relatively selective roles in mediating the transcriptional effects of nuclear receptors. Evidence indicates, however, that additional factors are required for the transcriptional activities of many CBP-dependent transcription factors, including STAT 1, AP-1 and CREB, and that complexes containing such coactivators, for example, CBP/p300 and NCoA, are involved in transmitting an activation signal to the promoter. Since CBP and p300-containing complexes appear to be limiting in cells, antagonistic interactions between signaling pathways can be due, at least in part, to competition for these complexes. Thus, a need exists to identify different classes of transcription factors that are regulated by a CBP-containing complex and to identify the coactivator proteins involved in such complexes. The present invention satisfies this need and provides related advantages as well.

SUMMARY OF THE INVENTION

The present invention provides a substantially purified nucleic acid molecule having a nucleotide sequence encoding a transcriptional coactivator protein, designated p/CIP, which binds to CBP/p300-dependent transcription factors and regulates their activity. For example, the invention provides a substantially purified nucleic acid molecule having the nucleotide sequence shown in FIG. 1, which encodes murine p/CIP, and a nucleotide sequence complementary to that shown in FIG. 1.

The invention also provides a substantially purified nucleic acid molecule encoding an active fragment of a p/CIP polypeptide, which has a nucleotide sequence encoding substantially the same amino acid sequence as a portion of a p/CIP polypeptide. Such a nucleic acid molecule can encode, for example, an active fragment including a CBP interaction domain, such as a fragment having about amino acids 758 to 1115 of p/CIP shown in FIG. 1, or a nuclear receptor interaction domain, such as a fragment having about amino acids 591 to 803 or about amino acids 680 to 740 of p/CIP shown in FIG. 1.

Further provided herein is a substantially purified nucleic acid molecule having a nucleotide sequence encoding a full length mouse NCoA-2 protein, which is related to p/CIP. The invention also provides a substantially purified NCoA-2 active fragment, having a nucleotide sequence encoding substantially the same amino acid sequence as a portion of a NCoA-2 polypeptide. Such a NCoA-2 active fragment can include, for example, a nuclear receptor interaction domain.

The invention also provides vectors comprising a nucleic acid molecule of the invention and host cells containing such vectors. In addition, the invention provides a substantially purified p/CIP nucleotide sequence having at least about 14 consecutive nucleotides of the nucleotide sequence shown in FIG. 1, or a nucleotide sequence complementary thereto.

The present invention also provides a substantially purified p/CIP polypeptide, which can bind to a CBP/p300-dependent transcription factor and regulate its activity. For example, the invention provides a substantially purified p/CIP polypeptide having substantially the same amino acid sequence as p/CIP shown FIG. 1. The invention additionally provides a substantially purified p/CIP active fragment having substantially the same amino acid sequence as a portion of a p/CIP polypeptide. A particularly useful p/CIP active fragment can include, for example, a CBP interaction domain or a nuclear receptor interaction domain, or can be an portion of a p/CIP polypeptide useful for eliciting production of an antibody that specifically binds to p/CIP.

The invention further provides a substantially purified NCoA-2 polypeptide having substantially the same amino acid sequence as amino acid sequence shown in FIG. 2a. Active fragments of a NCoA-2 polypeptide of the invention also are provided herein.

The invention also provides anti-p/CIP antibodies that specifically bind to p/CIP, as well as p/CIP-binding fragments of such antibodies. The invention further provides anti-NCoA-2 antibodies and antigen binding fragments thereof. In addition, the invention provides cell lines producing anti-p/CIP antibodies or anti-NCoA-2 antibodies.

The present invention further provides methods of identifying an effective agent that alters the association of p/CIP or NCoA-2 polypeptide with a second protein, such as a nuclear receptor or a CBP, which associates with the p/CIP or NCoA-2 polypeptide in vitro or in vivo. The method includes the steps of contacting a p/CIP or NCoA-2 polypeptide with an agent under conditions that allow the p/CIP or NCoA-2 polypeptide to associate with the second protein, and detecting an altered association of the p/CIP or NCoA-2 polypeptide with the second protein. An agent that alters the association of p/CIP, for example, with a second protein can be a peptide, a polypeptide, a peptidomimetic or an organic molecule, such an effective agent being useful, for example, for modulating the level of transcription in a cell. For example, a peptide portion of p/CIP comprising a helical leucine-rich, charged domain (LCD), can inhibit the transcriptional activity of one type of nuclear receptor, such as the retinoic acid receptor, but not of a second, related nuclear receptor such as the estrogen receptor, whereas a second LCD of p/CIP can inhibit signal transduction induced by interferon γ, but not signal transduction induced by retinoic acid. Thus, selected peptide portions of p/CIP or of NCoA-2 can be valuable for regulating gene expression in a cell, and these and other effective agents can have therapeutic efficacy.

BRIEF DESCRIPTION OF THE DRAWINGS

FIGS. 2a to 2d provide a characterization of p/CIP and a related member of the NCoA family, NCoA-2 (SEQ ID NO: 3).

FIG. 2a compares the amino acid sequences of the full length murine p/CIP and murine NCoA-2 polypeptides. The conserved bHLH, PAS "A" domain, the nuclear receptor interaction domains and the minimal nuclear receptor and CBP interaction domains are boxed, and repeat motifs involved in critical interactions are bracketed.

FIGS. 2b and 2c provide western blot analyses of total cell extracts for p/CIP, NCoA-1 and NCoA-2 in various tissues and cell lines, showing widespread expression of all three proteins, although relative levels differ.

FIG. 2d provides schematic diagrams showing regions of homology of p/CIP with NCoA-1 and NCoA-2. The asterisks refer to the repeated peptide motifs that appear to be of functional importance (see FIGS. 6 and 7).

FIG. 3a demonstrates interactions between recombinant GST proteins and NCoA proteins from HeLa whole cell extracts detected using an anti-p/CIP antibody (left) or an anti-NCoA-1 antibody (right).

FIG. 3b (left) shows co-immunoprecipitation of CBP/p300 and p/CIP. Anti-p/CIP, anti-NCoA-1 or anti-NCoA-2 IgG was incubated with HeLa whole cell extracts and immunocomplexes were separated by SDS-PAGE and probed using anti-CBP/p300 IgG. FIG. 3b (right) shows the detection of CBP/p300 in supernatant following immunodepletion of whole cell extracts with specific anti-NCoA antibodies.

FIG. 3c shows the results of yeast two-hybrid assays mapping regions of interaction between p/CIP and the CBP C-terminus (aa 2058–2170) or liganded estrogen receptor (LBD).

FIG. 3d demonstrates that a common nuclear receptor interaction domain is found in p/CIP, NCoA-1 and NCoA-2 by yeast two-hybrid assay. Ligands (+) were estradiol ($10^{-6}$ M), Triac ($10^{-6}$ M) or retinoic acid ($10^{-6}$ M)

FIG. 3e shows p/CIP, NCoA-1 or NCoA-2 interactions with nuclear receptors in vitro. Recombinant GST-nuclear receptor proteins were incubated with whole cell extract in the presence (+) or absence (−) of ligand, then western blot analysis was performed using p/CIP-, NCoA-1- or NCoA-2-specific IgG.

FIG. 4 demonstrates a role of P/CIP in the function of CBP-dependent transcription factors.

FIG. 4a shows the effect of microinjection of affinity-purified anti-p/CIP IgG on ligand-dependent gene activation by RAR in Rat-1 cells.

FIG. 4b shows experiments as in FIG. 4a, but performed using minimal promoters with four copies of the estrogen (ERE), thyroid hormone (TRE) or progesterone (PRE) receptor response elements.

FIG. 4c demonstrates that both CBP and p/CIP expression vectors are required to rescue anti-p/CIP IgG inhibition of RAR-dependent gene activation.

FIG. 4d shows the effect of expression of the p/CIP core CBP interaction domain (947–1084) on RAR dependent transcription (left) or on SP-1 or CMV dependent transcription (right).

FIG. 5 demonstrates a role for NCoA-1 and NCoA-2 in nuclear receptor function.

FIG. 6 shows the leucine-rich charged domains (LCD's) in p/CIP/NCoA/CBP.

FIG. 6b shows that mutation of amino acids 70–73 in CBP (QLSELL (SEQ ID NO: 5, aa 8–13) ->QLAAAA (SEQ ID NO: 12)) resulted in a complete loss of ligand-dependent interaction with T3R.

FIG. 6c shows results of the yeast two-hybrid assay of interactions between the NCoA-1 nuclear receptor interaction domains (aa 635–760) with nuclear receptors (left). Mutations of the LCD2 motif (RLHRLL (SEQ ID NO: 5, aa 8–13)->RLAAAA (SEQ ID NO: 12)) abolished ligand-dependent interaction, while peptides encompassing LCD2 (37 amino acids "aa") alone or LCD6 (59 amino acids) were sufficient for ligand-dependent interaction (center). 24-mer peptides encompassing LCD1, LCD2 or a control peptide were tested for ability to inhibit binding of $^{35}$S-labeled NCoA interaction domain fragment (aa 635–760) to liganded RAR with TTNPB (1 μM) (right).

FIG. 7 demonstrates that distinct helical motifs block transcriptional effects of specific signal transduction pathways.

FIG. 7a shows that a 19-mer peptide, corresponding to NCoA-1 LCD4, but not a control peptide (CBP-622, control P), inhibits retinoic acid induced, but not interferon γ induced gene expression.

FIG. 7b shows the effect of microinjection of the N-terminal 22 amino acids of CBP (CBP N'-P1), a synthetic N-terminal CBP peptide, on retinoic acid and interferon gene activation events. A synthetic peptide corresponding to the identical peptide lacking the eight amino terminal amino acids (CBP N'-P2) failed to inhibit interferon-dependent gene activation events.

FIG. 7c shows, similar to FIG. 7b, that interferon γ inhibition of retinoic acid-dependent activation of the RARE/LacZ reporter (right panel) was fully abolished by co-injection of the CBP N'-P1 peptide, which had no effect on retinoic acid dependent inhibition of the GAS/LacZ reporter by activated retinoic acid reporter.

DETAILED DESCRIPTION OF THE INVENTION

Figure 2B:
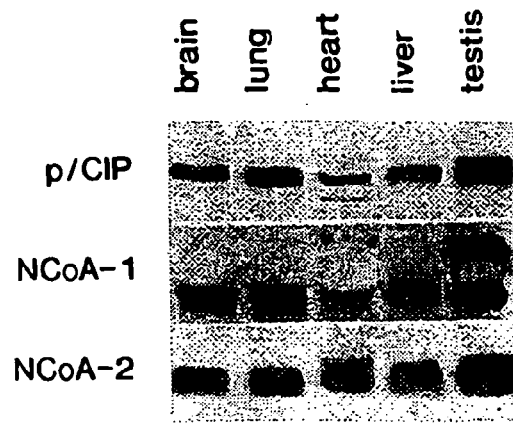

The present invention provides a substantially purified nucleic acid molecule encoding a transcriptional coactivator protein, designated p/CIP (p300/CBP/co-integrator-associated Protein), which binds to CBP/p300-dependent transcription factors and regulates their activity. For example, the invention provides a substantially purified nucleic acid molecule having the nucleotide sequence shown in FIG. 1, which encodes p/CIP, and a nucleotide sequence complementary to that shown in FIG. 1. As disclosed herein, p/CIP is a member of the NCoA (Nuclear receptor Co-Activator) gene family and is involved in regulating the transcriptional activities of various CBP-dependent transcription factors, including STAT 1, AP-1 and CREB. In addition, the invention provides a substantially purified nucleic acid molecule encoding a full length murine NCoA-2 polypeptide having the amino acid sequence shown in FIG. 2a.

As used herein, the term "substantially purified," when used in reference to a nucleic acid molecule of the invention, means that the nucleic acid molecule is relatively free from contaminating lipids, proteins, nucleic acids or other cellular material normally associated with a nucleic acid molecule in a cell. A substantially purified nucleic acid molecule of the invention can be obtained, for example, by chemical synthesis of the nucleotide sequence shown in FIG. 1 or by cloning the molecule using methods such as those disclosed in Example I.

As disclosed herein, CBP is present in a complex with p/CIP, which is required for transcriptional activity of nuclear receptors and other CBP/p300-dependent transcription factors, including STAT and AP-1. The related nuclear receptor coactivator protein, NCoA-1, also is specifically required for ligand-dependent gene activation by nuclear receptors. p/CIP, NCoA-1, and CBP contain related leucine-rich charged helical interaction motifs that are required for receptor-specific mechanisms of gene activation. The disclosure of these leucine-rich motifs permits selective inhibition of distinct signal transduction pathways.

CBP and p300 are functionally conserved proteins that have intrinsic acetylase activity and serve essential roles in activation by a large number of regulated transcription factors, including nuclear receptors, CREB, AP-1, bHLH and STAT proteins (see, for example, Chakravarti et al., *Nature* 383:99–103 (1996); Kwok et al., *Nature* 370:223–226 (1994); Arias et al., *Nature* 370: 226–229 (1994); Eckner et al., *Genes and Devel.* 10(19): 2478–2490 (1996), each of which is incorporated herein by reference).

In addition to CBP and p300, a series of factors that exhibit ligand-dependent and AF2-dependent binding to nuclear receptor C-termini have been identified biochemically (see Halachmi et al., *Science* 264:1455–1458 (1994); Cavailles et al., *EMBO J.* 14:3741–3751 (1995); Kurokawa et al., *Nature* 377:451–454 (1995)) and by expression cloning (see Lee et al., *Nature* 374:91–94 (1995); Le Douarin et al., *EMBO J.* 14:2020–2033 (1995); Voegel et al., *EMBO J.* 15(14):3667–3675 (1996); Hong et al., *Proc. Natl. Acad. Sci., USA* 93:4948–4952 (1996)). Two homologous factors, termed SRC-1/NCoA-1 and TIF-2/GRIP-1, increase ligand-dependent transcription by several nuclear receptors in cotransfection assays and constitute a nuclear receptor coactivator (NCoA) gene family.

p/CIP is a NCoA/SRC family member that forms a complex with CBP in a cell. Surprisingly, both p/CIP and NCoA-1 are required for the function of nuclear receptors, while p/CIP, but not NCoA-1, is required for function of other CBP-dependent transcription factors. A series of helical leucine-rich, charged residue-rich domains (LCD's) within these factors serve as interaction motifs that are involved in assembly of a coactivator complex and that contribute to the specificity of nuclear receptor activation events.

Studies of CBP, NCoA-1 and p/CIP have led to the identification of a series of helical motifs that are required for NCoA/nuclear receptor interaction, NCoA/CBP interaction and CBP/STAT interaction. Based on the identification of these helical motifs, corresponding peptides have been developed that, when injected into cells, selectively block signaling by retinoic acid, estrogen or interferon γ. These results demonstrate that the targeting of specific interaction motifs present in coactivator complexes can result in highly selective effects on patterns of gene expression. These observations further indicate that the utilization of specific interaction motifs by nuclear receptors can be altered by different classes of ligands, resulting in selective activities that can be of therapeutic benefit. Thus, the invention provides methods of identifying agents that modulate the activity of specific classes of transcription factors.

As disclosed herein, the cloned p/CIP cDNA is a novel member of the NCoA gene family. Like NCoA-1 (SRC-1) and NCoA-2 (TIF2, GRIP2), p/CIP interacts with several nuclear receptors in a ligand-dependent manner. Analysis of p/CIP, NCoA-1 and NCoA-2 has led to identification of a series of helical interaction motifs that mediate interactions between NCoA proteins and nuclear receptors, and a separate series of helical motifs that mediate interactions between NCoA proteins and CBP (see, for example, FIG. 2a). Mutations within these motifs reduce the ability of the coactivator to mediate transcriptional activation. Remarkably, microinjection of peptides cornerbanding to specific helical motifs exert selective inhibitory effects on transcription by different classes of transcription factors. Using this strategy, effective agents such as peptides have been identified that selectively block STAT 1 activity but not nuclear receptor-dependent transcription. In addition, effective agents have been identified that selectively block retinoic acid receptor activity but not STAT 1 activity. These agents have been used to demonstrate that inhibitory effects of interferon γ on retinoic acid transcription involve the CBP/p/CIP coactivator complex.

The invention also provides vectors comprising a nucleic acid molecule of the invention and host cells containing such vectors. In addition, the invention provides nucleotide sequences that bind to a nucleic acid molecule of the invention, such nucleotide sequences being useful, for example, as probes, which can identify the presence of a nucleic acid molecule encoding p/CIP in a sample or as antisense molecules, which can inhibit the expression of a nucleic acid molecule encoding a p/CIP.

Figures 1, 3F:
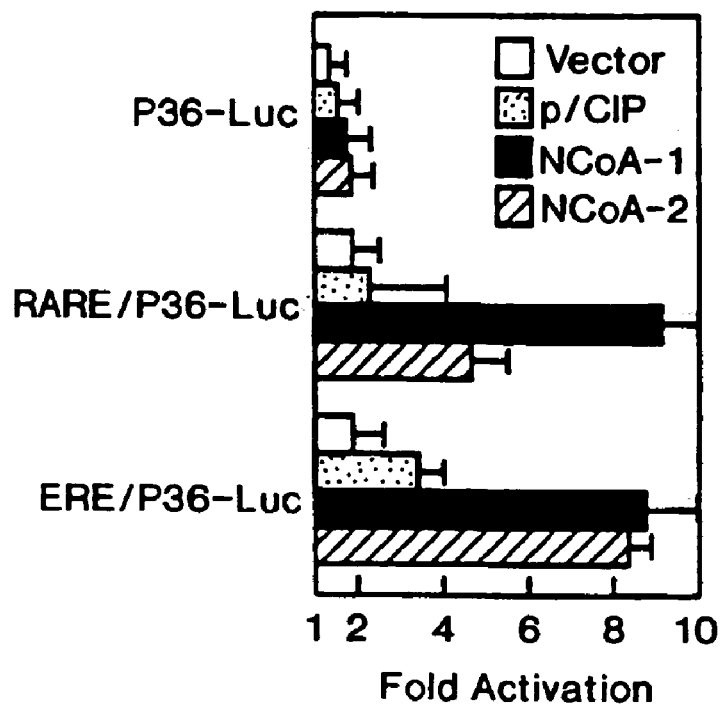
FIG. 1 shows the nucleotide sequence (SEQ ID NO: 1) and deduced amino acid sequence (SEQ ID NO: 2) of p/CIP.
FIG. 3f shows the results of transcription activation studies, in which reporter genes containing the minimal prolactin promoter (P-36 luciferase), alone, or two copies of the indicated response elements, and plasmids expressing p/CIP, NCoA-1 or NCoA-2 were transfected into HeLa cells in the presence of the corresponding ligand. The effect of varying amounts of plasmid expressing GAL4 (1–147), GAL4-NCoA-1 or GAL4-p/CIP fusion proteins on a minimal $(UAS)_6$-dependent reporter are shown in the right panel.
Figures 2, 3F:
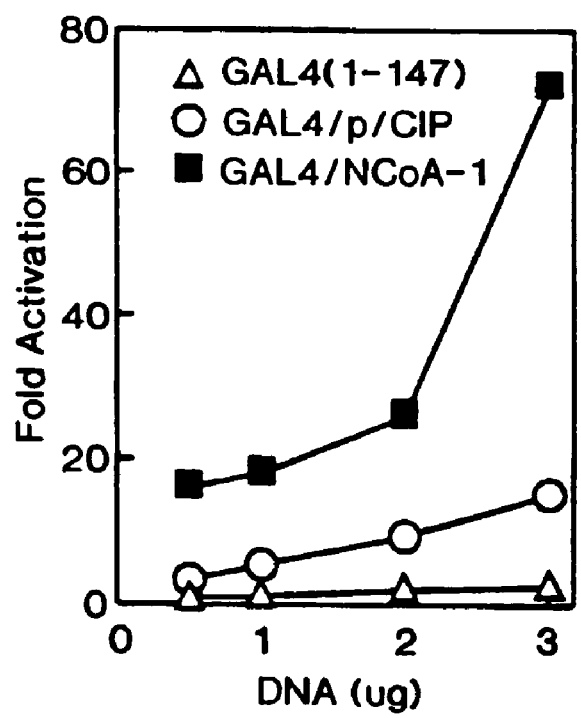

A substantially purified nucleic acid molecule of the invention is exemplified by the nucleotide sequence shown in FIG. 1, which encodes p/CIP protein, also shown in FIG. 1. Due to the degeneracy of the genetic code and in view of the disclosed amino acid sequence of a p/CIP protein, additional nucleic acid molecules of the invention would be well known to those skilled in the art. Such nucleic acid molecules have a nucleotide sequence that is different from that shown in FIG. 1 but, nevertheless, encode the amino acid sequence shown in FIG. 1. Thus, the invention provides a substantially purified nucleic acid molecule comprising a nucleotide sequence encoding the amino acid sequence of murine p/CIP as shown in FIG. 1. Similarly, the invention provides a substantially purified nucleic acid molecule encoding a full length NCoA-2 polypeptide having the amino acid sequence shown in FIG. 2a.

As used herein, reference to "a nucleic acid molecule encoding p/CIP" indicates 1) the polynucleotide sequence of one strand of a double stranded DNA molecule comprising the nucleotide sequence that codes, for example, for p/CIP and can be transcribed into an RNA that encodes the coactivator, or 2) an RNA molecule, which can be translated, for example, into p/CIP. It is recognized that a double stranded DNA molecule also comprises a second polynucleotide strand that is complementary to the coding strand and that the disclosure of a polynucleotide sequence comprising a coding sequence necessarily discloses the complementary polynucleotide sequence. Accordingly, the invention provides polynucleotide sequences, including, for example, polydeoxyribonucleotide or polyribonucleotide sequences that are complementary to the nucleotide sequence shown in FIG. 1 or to a nucleic acid molecule encoding p/CIP having the amino acid sequence shown in FIG. 1.

As used herein, the term "polynucleotide" is used in its broadest sense to mean two or more nucleotides or nucleotide analogs linked by a covalent bond. The term "oligonucleotide" also is used herein to mean two or more nucleotides or nucleotide analogs linked by a covalent bond, although those in the art will recognize that oligonucleotides generally are less than about fifty nucleotides in length and, therefore, are a subset within the broader meaning of the term "polynucleotide."

In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide also can comprise nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22:5220–5234 (1994); Jellinek et al., *Biochemistry* 34:11363–11372 (1995); Pagratis et al., *Nature Biotechnol.* 15:68–73 (1997)). The covalent bond linking the nucleotides of a polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22:977–986 (1994); Ecker and Crooke, *BioTechnology* 13:351360 (1995)).

Where it is desired to synthesize a polynucleotide of the invention, the artisan will know that the selection of particular nucleotides or nucleotide analogs and the covalent bond used to link the nucleotides will depend, in part, on the purpose for which the polynucleotide is prepared. For example, where a polynucleotide will be exposed to an environment containing substantial nuclease activity, the artisan will select nucleotide analogs or covalent bonds that are relatively resistant to the nucleases. A polynucleotide comprising naturally occurring nucleotides and phosphodiester bonds can be chemically synthesized or can be produced with recombinant DNA methods using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs and, therefore, can be used to produce such a polynucleotide recombinantly from an appropriate template (Jellinek et al., supra, 1995).

The invention also provides nucleotide sequences that can bind to a nucleic acid molecule encoding p/CIP. Such nucleotide sequences are useful, for example, as probes, which can hybridize to a nucleic acid molecule encoding a p/CIP and allow the identification of the nucleic acid molecule in a sample. A nucleotide sequence of the invention is characterized, in part, in that it is at least nine nucleotides in length, such sequences being particularly useful as primers for the polymerase chain reaction (PCR), and can be, for example, at least fourteen, fifteen, sixteen, seventeen, eighteen, nineteen, twenty or twenty-one nucleotides in length. If desired, a nucleotide sequence of the invention can have at least twenty-five, thirty, thirty-five, forty or fifty nucleotides of the nucleotide sequence shown in FIG. 1. Such a nucleotide sequence of the invention is useful as a hybridization probe or as a primer for PCR and can be used, for example, to identify homologous nucleic acid molecules encoding p/CIP proteins in other eukaryotes, particularly other mammals, including humans.

As disclosed herein, p/CIP is a member of the NCoA protein family and, therefore, shares conserved structural regions with other members of this family. Thus, a nucleic acid molecule encoding p/CIP shares regions of substantial homology with a nucleic acid molecule encoding an NCoA protein such as NCoA-2. However, a comparison of the nucleic acid molecules encoding p/CIP and NCoA-2, for example, also will reveal nucleotide sequences that are unique to p/CIP, such nucleotide sequences being encompassed within the invention.

A substantially purified nucleotide sequence of the invention can comprise a portion of a coding sequence of a nucleic acid molecule encoding p/CIP or of a sequence complementary thereto, depending on the purpose for which the nucleotide sequence is to be used. In addition, a mixture of a coding sequence and its complementary sequence can be prepared and, if desired, can be allowed to anneal to produce double stranded oligonucleotides. The invention also provides antisense nucleic acid molecules, which are complementary to a nucleic acid molecule encoding p/CIP and can bind to and inhibit the expression of the nucleic acid molecule.

A nucleic acid molecule of the invention, including an antisense molecule, can be introduced into a cell by methods of transfection, or can be contained in a plasmid or viral vector, which can be introduced into the cell, such that the nucleic acid molecule is stably or transiently expressed (see, for example, Sambrook et al., *Molecular Cloning: A laboratory manual* (Cold Spring Harbor Laboratory Press 1989); Ausubel et al., *Current Protocols in Molecular Biology* (Green Publ., NY 1994), each of which is incorporated herein by reference). Accordingly, the invention provides vectors comprising a nucleic acid molecule of the invention and host cells, which are appropriate for maintaining such vectors. Vectors, which can be cloning vectors or expression vectors, are well known in the art and commercially available. An expression vector comprising a nucleic acid molecule of the invention, which can encode a p/CIP or can be an antisense molecule, can be used to express the nucleic acid molecule in a cell.

In general, an expression vector contains the expression elements necessary to achieve, for example, transcription of the nucleic acid molecule, although such elements also can be inherent to the nucleic acid molecule cloned into the vector. In particular, an expression vector contains or encodes a promoter sequence, which can provide constitutive or, if desired, inducible expression of a cloned nucleic acid sequence, a poly-A recognition sequence, and a ribosome recognition site, and can contain other regulatory elements such as an enhancer, which can be tissue specific. The vector also contains elements required for replication in a procaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, *Meth, Enzymol.*, Vol. 185, D. V. Goeddel, ed. (Academic Press, Inc., 1990); Jolly, *Canc. Gene Ther.* 1:51–64 (1994); Flotte, *J. Bioenerg. Biomemb.* 25:37–42 (1993); Kirshenbaum et al., *J. Clin. Invest* 92:381–387 (1993), which is incorporated herein by reference).

A nucleic acid molecule, including a vector, can be introduced into a cell by any of a variety of methods known in the art (Sambrook et al., supra, 1989, and in Ausubel et al., *Current Protocols in Molecular Biology*, John Wiley and Sons, Baltimore, Md. (1994), which is incorporated herein by reference). Such methods include, for example, transfection, lipofection, microinjection, electroporation and infection with recombinant vectors or the use of liposomes.

Introduction of a nucleic acid molecule by infection with a viral vector is particularly advantageous in that it can efficiently introduce the nucleic acid molecule into a cell ex vivo or in vivo. Moreover, viruses are very specialized and typically infect and propagate in specific cell types. Thus, their natural specificity can be used to target the nucleic acid molecule contained in the vector to specific cell types. Viral or non-viral vectors also can be modified with specific receptors or ligands to alter target specificity through receptor mediated events.

A nucleic acid molecule also can be introduced into a cell using methods that do not require the initial introduction of the nucleic acid molecule into a vector. For example, a nucleic acid molecule encoding a p/CIP can be introduced into a cell using a cationic liposome, which also can be modified with specific receptors or ligands as described above (Morishita et al., *J. Clin. Invest.*, 91:2580–2585 (1993), which is incorporated herein by reference; see, also, Nabel et al., supra, 1993)). In addition, a nucleic acid molecule can be introduced into a cell using, for example, adenovirus-polylysine DNA complexes (see, for example, Michael et al., *J. Biol. Chem.*, 268:6866–6869 (1993), which is incorporated herein by reference). Other methods of introducing a nucleic acid molecule into a cell such that the encoded p/CIP or antisense nucleic acid molecule can be expressed are well known (see, for example, Goeddel, supra, 1990).

Selectable marker genes encoding, for example, a polypeptide conferring neomycin resistance ($Neo^R$) also are readily available and, when linked to a nucleic acid molecule of the invention or incorporated into a vector containing the nucleic acid molecule, allow for the selection of cells that have incorporated the nucleic acid molecule. Other selectable markers such as that conferring hygromycin, puromycin or ZEOCIN (Invitrogen, Carlsbad Calif.) resistance are known to those in the art of gene transfer as markers useful for identifying cells containing the nucleic acid molecule, including the selectable marker gene.

A "suicide" gene also can be incorporated into a vector so as to allow for selective inducible killing of a cell containing the gene. A gene such as the herpes simplex virus thymidine kinase gene (TK) can be used as a suicide gene to provide for inducible destruction of such cells. For example, where it is desired to terminate the expression of an introduced nucleic acid molecule encoding p/CIP or an antisense p/CIP nucleic acid molecule in cells containing the nucleic acid molecule, the cells can be exposed to a drug such as acyclovir or gancyclovir, which can be administered to an individual.

Numerous methods are available for transferring nucleic acid molecules into cultured cells, including the methods described above. In addition, a useful method can be similar to that employed in previous human gene transfer studies, where tumor infiltrating lymphocytes (TILs) were modified by retroviral gene transduction and administered to cancer patients (Rosenberg et al., *New Engl. J. Med.* 323:570–578 (1990); see, also, Anderson et al., U.S. Pat. No. 5,399,346, issued Mar. 21, 1995, each of which is incorporated herein by reference).

The present invention also provides a substantially purified p/CIP polypeptide, which forms a complex with CBP/p300 in a cell and regulates CBP/p300-dependent transcriptional activity. A p/CIP polypeptide of the invention is exemplified herein by murine p/CIP, which is a protein of about 152 kDa that has a conserved amino-terminal basic helix-loop-helix domain, PAS "A" domain, a serine/threonine-rich region and a carboxy-terminal glutamine-rich region. Murine p/CIP is related to SRC-1/NCoA-1 and NCoA-2/TIF-2, showing overall amino acid identity of 31% and 36%, respectively. As disclosed herein, p/CIP is required for transcriptional activation by CBP-dependent transcription factors, including nuclear receptors such as the retinoic acid receptor, estrogen receptor, thyroid receptor and progesterone receptor, and other CBP-dependent transcription factors such as STAT 1 (see Example I).

Thus, the present invention provides a substantially purified p/CIP polypeptide. Such a polypeptide can have, for example, substantially the same amino acid sequence as murine p/CIP shown in FIG. 1 (see, also, FIG. 2a). Further provided herein is a substantially purified p/CIP active fragment having substantially the same amino acid sequence as a portion of a p/CIP polypeptide. Such an active fragment can include, for example, a CBP interaction domain or a nuclear receptor interaction domain. LCD peptide portions of p/CIP also are provided (see Example I).

The term "substantially purified," as used herein in reference to a polypeptide or fragment thereof, means that the polypeptide or polypeptide fragment is relatively free from contaminating lipids, proteins, nucleic acids or other cellular material normally associated with a polypeptide in a cell.

As used herein, the term "p/CIP" or "p/CIP polypeptide" means the polypeptide referred to herein as "p300/CBP/CoIntegrator-associated Protein" and includes the murine p/CIP polypeptide shown in FIG. 1. As described above, murine p/CIP displays homology to SRC-1/NCoA-1 and NCoA-2/TIF-2, sharing basic helix-loop-helix domains, a PAS "A" domain, serine/threonine-rich region and glutamine-rich region with NCoA-1 and NCoA-2.

The term p/CIP encompasses murine p/CIP and is intended to include related polypeptides having substantial amino acid sequence similarity to this polypeptide. Such related polypeptides will exhibit greater sequence similarity to p/CIP than to SRC-1/NCoA-1 or to NCoA-2/TIF-2 and include alternatively spliced forms of p/CIP and isotype variants of the amino acid sequence shown in FIG. 1. The term p/CIP also encompasses homologous polypeptides obtained from different mammalian species, such as a human homolog of the murine p/CIP polypeptide disclosed in FIG. 1. A p/CIP polypeptide generally has an amino acid identity of greater than about 40%, preferably greater than about 50%, more preferably greater than about 60%, and can have an amino acid identity of greater than about 70%, 75%, 80%, 85%, 90% or 95% with the murine p/CIP amino acid sequence disclosed in FIG. 1.

As used herein, the term "substantially the same amino acid sequence," when used in reference to a p/CIP amino acid sequence, is intended to mean the amino acid sequence shown in FIG. 1, or a similar, non-identical sequence that is considered by those skilled in the art to be a functionally equivalent nucleotide or amino acid sequence. Thus, a polypeptide that has substantially the same amino acid sequence as a p/CIP polypeptide can have one or more modifications such as amino acid additions, deletions or substitutions relative to the amino acid sequence shown in FIG. 1, provided that the p/CIP polypeptide retains at least one biological activity of a native p/CIP polypeptide.

Therefore, it is understood that modifications can be made without destroying the biological function of a p/CIP polypeptide. Also, for example, genetically engineered variants of p/CIP either alone or fused to heterologous proteins that retain at least one measurable activity in binding to a CBP protein, binding to a nuclear receptor, activity in retinoic acid, estrogen, thyroid or progesterone dependent transcription, activity in other CBP-dependent transcription, or other inherent biological activity fall within the definition of a p/CIP polypeptide.

It is understood that modifications of primary amino acid sequence can result in polypeptides which have substantially equivalent, enhanced or reduced function as compared to the murine p/CIP sequence set forth in FIG. 1. These modifications can be deliberate, as through site-directed mutagenesis, or can be accidental such as through mutation in hosts harboring a p/CIP encoding nucleic acid molecule. All such modified polypeptides are included in the definition of a p/CIP polypeptide as long as at least one biological function of a p/CIP polypeptide is retained. Further, various molecules can be attached to a p/CIP polypeptide including, for example, other polypeptides, carbohydrates, lipids, or chemical moieties using methods well known in the art. Such modifications are included within the term "p/CIP polypeptide," as defined herein.

Further provided herein is an isolated active fragment of a p/CIP polypeptide, which includes substantially the same amino acid sequence as a portion of a p/CIP polypeptide. As used herein, the term "active p/CIP fragment" means a peptide or polypeptide which has substantially the same amino acid sequence as a portion of a p/CIP polypeptide, provided that the fragment retains at least one biological activity of a p/CIP polypeptide. As defined herein, an active fragment generally has an amino acid sequence of about 15 to about 400 contiguous residues and can have, for example, an amino acid sequence of at least about 18, 20, 25, 30, 35, 40, 50, 100, 150, 200, 250, 300, 350 or 400 contiguous residues. A particularly useful active fragment has from about 80 to about 150 amino acids. A biological activity of a p/CIP polypeptide that is retained by an active p/CIP fragment can be, for example, measurable activity in binding to a CBP protein, binding to a nuclear receptor, activity in retinoic acid, estrogen, thyroid or progesterone dependent transcription, activity in other CBP-dependent transcription, or other inherent biological activity.

An isolated p/CIP active fragment of the invention can include, for example, a CBP interaction domain. Such a CBP-binding active fragment can have, for example, an amino acid sequence that is identical or substantially the same as a portion of p/CIP shown in FIG. 1, for example, substantially the same as about amino acids 758 to 1115 of p/CIP, about amino acids 947 to 1084 of p/CIP, or about amino acids 163 to 610 of p/CIP shown in FIG. 1. Additional p/CIP active fragments having a CBP interaction domain can readily be identified, for example, using yeast two-hybrid assays or microinjection assays, as set forth in Example I. As disclosed herein, such an active fragment can block CBP-dependent gene activation, for example, interferon-γ or TPA stimulated gene activation or retinoic acid dependent gene activation.

A substantially purified p/CIP active fragment of p/CIP can include a nuclear receptor interaction domain. Such a nuclear receptor-binding active fragment of p/CIP can have, for example, an amino acid sequence that is identical or substantially the same as a portion of p/CIP shown in FIG. 1, and can bind a nuclear receptor such as the estrogen receptor, for example, in a ligand-dependent manner. An example of a p/CIP active fragment having a nuclear receptor interaction domain is a fragment having substantially the same amino acid sequence as about amino acids 591 to 803 of p/CIP or about amino acids 680 to 740 of p/CIP shown in FIG. 1.

Also provided herein is a novel member of the nuclear receptor co-activator family designated NCoA-2. As disclosed herein, murine NCoA-2 is a polypeptide of about 160 kDa that interacts with a 100 amino acid region in the carboxy termini of CBP (amino acids 2058–2170), as well as with the liganded estrogen receptor. Thus, the invention provides a substantially purified NCoA-2 polypeptide having substantially the same amino acid sequence as the amino acid sequence shown in FIG. 2a. In addition, the invention provides a substantially purified NCoA-2 active fragment having substantially the same amino acid sequence as a portion of a NCoA-2 polypeptide. An active fragment of a NCoA-2 polypeptide can include, for example, a nuclear receptor interaction domain.

As used herein, the term "NCoA-2" or "NCoA-2 polypeptide" is intended to mean a polypeptide having substantial similarity to the murine NCoA-2 polypeptide shown in FIG. 2a. Like a p/CIP polypeptide, a NCoA-2 polypeptide has a basic helix-loop-helix domain, a PAS "A" domain, a serine/threonine-rich region and a glutamine-rich region.

The term NCoA-2 encompasses murine NCoA-2 and is intended to include related polypeptides having substantial amino acid sequence similarity to this polypeptide. Such related polypeptides will exhibit greater sequence similarity to NCoA-2 than to SRC-1/NCoA-1 or to p/CIP and include alternatively spliced forms of NCoA-2 and isotype variants of the amino acid sequences shown in FIG. 2a. The term NCoA-2 also encompasses homologous polypeptides obtained from different mammalian species, although the human TIF-2 and GRIP-1 polypeptides described in Voegel et al., EMBO J. 15:3667–3675 (1996) and Hong et al., Proc. Natl. Acad. Sci. USA 93:4948–4952 (1996), each of which is incorporated by reference herein, are explicitly excluded from the term NCoA-2 polypeptide as defined herein. A NCoA-2 polypeptide generally has an amino acid sequence having an amino acid identity of greater than about 70%, preferably greater than about 75%, more preferably greater than about 80%, and can have an amino acid identity of greater than about 85%, 90% or 95% with the murine NCoA-2 amino acid sequence disclosed in FIG. 2a.

An active fragment of a p/CIP or NCoA-2 polypeptide can be produced by any of several methods well known in the art. For example, an active fragment of the invention can be produced by enzymatic cleavage of a p/CIP polypeptide using a proteolytic enzyme such as trypsin, chymotrypsin or the like, or a combination of such enzymes. The resulting enzymatic digestion subsequently can be purified using well known methods. An active fragment also can be produced using methods of solution or solid phase peptide synthesis or can be expressed from a nucleic acid molecule such as a portion of the coding region of the nucleic acid sequence shown in FIG. 1, or can be purchased from a commercial source.

The invention also provides an LCD peptide portion of p/CIP, which includes a helical leucine-rich, charged domain (LCD) and which can inhibit the transcriptional activity of one type of nuclear receptor, such as the retinoic acid receptor, but not of a second, related nuclear receptor such as the estrogen receptor. An LCD peptide portion of p/CIP also can selectively inhibit signal transduction induced by interferon γ without inhibiting signal transduction induced by retinoic acid. Thus, an LCD peptide portion of p/CIP or of another NCoA can be useful for regulating gene expression in a cell.

An LCD peptide portion of p/CIP or NCoA-2 is characterized, in part, as containing one or more copies of the consensus core sequence, LXXLL, where L is leucine and X is independently selected to be any amino acid. Preferably, an LCD peptide portion contains at least three copies of the consensus core sequence LXXLL. An LCD peptide portion p/CIP can include, for example, one or more of the following amino acid sequences: KGHKKLLQLLTCS (SEQ ID NO: 2, aa 609–621), LLQEKHRJLHKLLQN (SEQ ID NO: 2, aa 670–684), KKENNALLRYLLDRDD (SEQ ID NO: 2, aa 723–738), LRNSLDDLLGPPS (SEQ ID NO: 2, aa 1037–1049), or RALLDQLHTFL (SEQ ID 2, aa 1058–1068). An LCD peptide portion of NCoA-2 can include, for example, one or more of the following amino acid sequences: KGQTKLLQLLTTK (SEQ ID NO: 3, aa 636–648), SLKEKHKILHRLLQD (SEQ ID NO: 3, an 682–696), KKENALLRYLLDKDD (SEQ ID NO: 3, aa 739–753), FGSSPDDLLCPHP (SEQ ID NO: 3, aa 1057–1069) or GALLDQLYLAL (SEQ ID NO: 3, aa 1078–1088). An LCD peptide portion of p/CIP or NCoA-2 can be a helical domain with amphipathic characteristics and can have a length of eight, nine, ten, twelve, fourteen, sixteen, twenty, forty, sixty, eighty or more residues.

As used herein, the term "amino acid" includes both amino acids and amino acid equivalents. An amino acid equivalent is a compound which departs from the structure of a naturally occurring amino acid, but which has substantially the structure of an amino acid, such that it can be substituted within a peptide or protein which retains its biological activity. Thus, for example, amino acid equivalents can include amino acids having side chain modifications or substitutions, and also can include related organic acids, amides or the like. Amino acid equivalents include amino acid mimetics, which are those structures which exhibit substantially the same spatial arrangement of functional groups as amino acids but do not necessarily have both the α-amino and α-carboxyl groups characteristic of amino acids.

The invention also provides anti-p/CIP antibodies and anti-murine NCoA-2 antibodies, as well as antigen binding fragments of such antibodies. In addition, the invention provides cells lines such as isolated cell lines that produce antibodies of the invention, particularly monoclonal antibodies. As used herein, the term "antibody" is used in its broadest sense to include polyclonal and monoclonal antibodies, as well as antigen binding fragments of such antibodies. With regard to an anti-p/CIP antibody, for example, the term "antigen" means a p/CIP protein, polypeptide or peptide portion thereof. An anti-p/CIP antibody, or antigen binding fragment of such an antibody, is characterized by having specific binding activity for p/CIP or a peptide portion thereof of at least about $1 \times 10^5$ $M^{-1}$. An anti-p/CIP antibody can have specific binding activity for p/CIP without binding other NCoA polypeptides such as NCoA-1 or NCoA-2. Fab, F(ab')$_2$, Fd and Fv fragments of an anti-p/CIP antibody, which retain specific binding activity for p/CIP, are included within the definition of an antibody. Similar antibodies can be identified with respect to the full length murine NCoA-2 polypeptide disclosed herein.

In addition, the term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al., *Science* 246:1275–1281 (1989), which is incorporated herein by reference. These and other methods of making, for example, chimeric, humanized, CDR-grafted, single chain, and bifunctional antibodies are well known to those skilled in the art (Winter and Harris, *Immunol. Today* 14:243–246 (1993); Ward et al., *Nature* 341:544–546 (1989); Harlow and Lane, *Antibodies: A laboratory manual* (Cold Spring Harbor Laboratory Press, 1988); Hilyard et al., *Protein Engineering: A practical approach* (IRL Press 1992); Borrabeck, *Antibody Engineering*, 2d ed. (Oxford University Press 1995); each of which is incorporated herein by reference).

Anti-p/CIP antibodies can be raised using as an immunogen a substantially purified full length p/CIP protein, which can be prepared from natural sources or produced recombinantly, or a peptide portion of a p/CIP polypeptide as defined herein, including synthetic peptides as described above. A non-immunogenic peptide portion of p/CIP can be made immunogenic by coupling the hapten to a carrier molecule such bovine serum albumin (BSA) or keyhole limpet hemocyanin (KLH), or by expressing the peptide portion as a fusion protein. Various other carrier molecules and methods for coupling a hapten to a carrier molecule are well known in the art and described, for example, by Harlow and Lane, supra, 1988.

Particularly useful antibodies of the invention are those that bind to uncomplexed p/CIP, but not to a p/CIP in a complex, for example, with CBP, and, conversely, those that bind to the complexed form of p/CIP, but not to the uncomplexed form. An anti-p/CIP antibody is useful, for example, for determining the presence or level of a p/CIP in a tissue sample, which can be a lysate or a histological section. The identification of the presence or level of a p/CIP in the sample can be made using well known immunoassay and immunohistochemical methods (Harlow and Lane, supra, 1988). An anti-p/CIP antibody also can be used to substantially purify p/CIP from a sample and, in addition, can be used to copurify a protein such as a transcription factor that is complexed with the p/CIP polypeptide. An anti-p/CIP antibody can be used to detect a p/CIP polypeptide in a sample of cells or in an organism.

A kit incorporating an anti-p/CIP antibody, which can be specific for the complexed or uncomplexed form of p/CIP, can be particularly useful. Such a kit can contain, in addition to an anti-p/CIP antibody, a reaction cocktail that provides the proper conditions for performing the assay, control samples that contain known amounts of p/CIP and, if desired, a second antibody specific for the anti-p/CIP antibody.

A protein such as an anti-p/CIP antibody, as well as p/CIP or a peptide portion thereof, can be labeled so as to be detectable using methods well known in the art (Hermanson, "Bioconjugate Techniques" (Academic Press 1996), which is incorporated herein by reference; Harlow and Lane, supra, 1988; chap. 9). For example, a protein can be labeled with various detectable moieties including a radiolabel, an enzyme, biotin, or a fluorochrome or fluorescent moiety, such as a green fluorescent protein (see U.S. Pat. No. 5,625,048; WO96/23810; WO97/28261; PCT/US97/12410; and PCT/US97/14593, each of which is incorporated herein by reference). Reagents for labeling a protein such as an anti-p/CIP antibody can be included in a kit containing the protein or can be purchased separately from a commercial source.

Following contact, for example, of a labeled antibody with a sample such as a tissue homogenate or a histological section of a tissue, specifically bound labeled antibody can be identified by detecting the particular moiety. Alternatively, a labeled second antibody can be used to identify specific binding of an unlabeled anti-p/CIP antibody. A second antibody generally will be specific for the particular class of the first antibody. Such second antibodies are readily available from commercial sources. The second antibody can be labeled using a detectable moiety as described above. When a sample is labeled using a second antibody, the sample is first contacted with a first antibody, which is an anti-p/CIP antibody, then the sample is contacted with the labeled second antibody, which specifically binds to the anti-p/CIP antibody and results in a labeled sample.

Methods for raising polyclonal antibodies, for example, in a rabbit, goat, mouse or other mammal, are well known in the art. In addition, monoclonal antibodies can be obtained using methods that are well known and routine to the skilled person (Harlow and Lane, supra, 1988). Essentially, spleen cells from a p/CIP-immunized mouse can be fused to an appropriate myeloma cell line such as SP/02 myeloma cells to produce hybridoma cells. Cloned hybridoma cell lines can be screened using labeled p/CIP protein to identify clones that secrete anti-p/CIP monoclonal antibodies. Hybridomas expressing anti-p/CIP monoclonal antibodies having a desirable specificity and affinity can be isolated and utilized as a continuous source of the antibodies, which are useful, for example, for preparing standardized kits as described above. Similarly, a recombinant phage that expresses, for example, a single chain anti-p/CIP antibody also provides a monoclonal antibody that can used for preparing standardized kits.

A monoclonal anti-p/CIP antibody can be used to prepare anti-idiotypic antibodies, which presents an epitope that mimics the epitope recognized by the monoclonal antibody used to prepare the anti-idiotypic antibodies. Where the epitope recognized by the monoclonal antibody includes, for example, an LCD, the anti-idiotypic antibody can act as an inhibitor of p/CIP binding to CBP or p/CIP binding to a transcription factor, thus providing a means to regulate a signal transduction pathway.

The present invention also provides a method of identifying an effective agent that alters the association of a p/CIP polypeptide with a second protein such as CBP or a transcription factor, or that alters the formation of a complex containing two or three of these proteins. The method includes the steps of contacting a p/CIP polypeptide and a second protein with an agent under conditions that allow the p/CIP polypeptide to associate with the second protein and detecting an altered association of the p/CIP polypeptide and said second protein. The altered association indicates that the agent is an effective agent. In a method of the invention, the p/CIP polypeptide can have, for example, the amino acid sequence shown in FIG. 1, and the second protein can be, for example, a CBP protein, a nuclear receptor or a CBP/p300-dependent transcription factor. An altered association can be detected, for example, by measuring the transcriptional activity of a reporter gene. In a method of the invention, a P/CIP polypeptide can be contacted with an agent in vitro or in a cell, including a prokaryotic cell such as a yeast cell and a eukaryotic cell, such as a mammalian cell, for example, a human cell.

The present invention further provides a method of identifying an effective agent that alters the association of a NCoA-2 polypeptide with a second protein. The method includes the steps of contacting a NCoA-2 polypeptide and a second protein with an agent under conditions that allow the NCoA-2 polypeptide to associate with the second protein and detecting an altered association of the NCoA-2 polypeptide and said second protein.

As used herein, the term "second protein" refers to a protein that specifically associates with a p/CIP or NCoA-2 polypeptide. It is recognized, however, that p/CIP and NCoA-2 can associate with more than one additional protein at the same time to form a complex. Thus, a second protein is exemplified herein by CBP proteins, by nuclear receptors and by other CBP/p300-dependent transcription factors, which form a complex with p/CIP or NCoA-2. Effective agents that alter the association, for example, of p/CIP, CBP and a transcription factor can be extremely valuable in that the agent can modulate transcriptional activity of the transcription factor.

The term "agent," as used herein, means a biological or chemical compound such as a simple or complex organic molecule, a peptide, a peptidomimetic, a polypeptide, a nucleic acid, a chemical or a small molecule. The screening assays described herein are particularly useful in that they can be automated, facilitating high through-put screening of randomly or rationally designed agents or libraries of agents, such as chemicals, small molecules, drugs, peptides, peptidomimetics or polypeptides, in order to identify those agents that alter the association of p/CIP or NCoA-2 with a second protein. If desired, an agent can be screened individually, or can be screened in combination with other agents, for example, in a library.

As used herein, the term "associate" or "association," when used in reference to a p/CIP or NCoA-2 polypeptide and a second (or second and third) protein means that the p/CIP or NCoA-2 polypeptide and the second protein have a binding affinity for each other such that they form a bound complex in vivo or in vitro, including in a cell in culture or in a reaction comprising substantially purified reagents. For convenience, the term "bind" or "interact" is used interchangeably with the term "associate".

The screening assays disclosed herein provide a method of identifying an "effective agent," which is an agent that can increase or decreased the affinity of an association between a p/CIP or NCoA-2 polypeptide and a second protein and that has presumptive therapeutic activity. The term "modulate" or "alter," as used herein in reference to the association of a p/CIP or NCoA-2 polypeptide and one or two other proteins, means that the affinity of the association is increased or decreased. Effective agents that can alter such association and, therefore, complex formation of p/CIP, CBP and a transcription factor, can be useful for modulating a signal transduction pathway and, therefore, expression of genes in the pathway. One skilled in the art understands that an effective agent that alters the association of p/CIP with a second protein such as a CBP protein may, additionally alter the association of other proteins with p/CIP. Alternatively, an effective agent can selectively alter the association of, for example, p/CIP with a CBP protein without altering the association of p/CIP with other proteins.

One skilled in the art understands that an effective agent can function directly or indirectly and by a variety of mechanisms to alter the association of a p/CIP polypeptide, or NCoA-2 polypeptide, with a second protein. An effective agent can function, for example, as a competitor of the binding interaction between a p/CIP polypeptide and a second protein, or between a NCoA-2 polypeptide and a second protein. For example, a peptide or peptidomimetic that mimics the structure of the CBP interaction domain or the nuclear receptor interaction domain of a p/CIP polypeptide can be an effective agent that decreases the affinity of the association of a p/CIP polypeptide with a second protein, as can be a fragment of a CBP protein or nuclear receptor that alters the association of p/CIP with a second protein. A peptide portion of p/CIP comprising an LCD, for example, amino acids 947 to 1084 of p/CIP (see FIG. 2A) is an example of such an agent, since the peptide inhibits, for example, retinoic acid-dependent gene activation (see Example I). Additional peptide effective agents, which can be peptides as small as about five amino acids, can be identified, for example, by screening a peptide library (see, for example, Ladner et al., U.S. Pat. No.: 5,223,409, which is incorporated herein by reference) using one of the assays described herein.

An effective agent also can bind to a p/CIP or NCoA-2 polypeptide at a site distant from the site of interaction, thereby altering the three-dimensional conformation of the polypeptide such that the affinity of the association with a second protein is increased or decreased. An effective agent also can produce an altered association by promoting a modification such as phosphorylation of a p/CIP or NCoA-2 polypeptide. In addition, an effective agent can sequester or alter the subcellular localization of a p/CIP or NCoA-2 polypeptide, thereby modulating the effective concentration of the polypeptide and the extent to which the polypeptide can associate with a second protein.

A variety of in vivo and in vitro screening assays for detecting an altered association are well known in the art including, for example, the two hybrid assay, coimmunoprecipitation assays, reporter assays and other well known methods such as equilibrium dialysis. One skilled in the art understands that methods for distinguishing the specific association of a p/CIP, for example, and a second protein from a non-specific interaction are routine and, generally, include performing the appropriate control experiments to demonstrate the absence of non-specific protein binding.

An effective agent can be identified by an altered level of reporter gene transcription as compared to a control level of transcription in the absence of the agent. A particularly useful reporter gene is cytosolic β-lactamase, which can be detected by the CCF2/AM substrate, as described in Tsien et al. (U.S. Pat. No. 5,741,657, which is incorporated herein by reference). If desired, a reporter gene can encode a protein expressed, for example, on the cell surface, and an altered level of reporter gene transcription detected by FACS analysis.

A two-hybrid system, such as the yeast two hybrid system, can be particularly useful for screening a panel of agents in order to detect an altered association of a p/CIP or NCoA-2 polypeptide with a second protein (see Example I). Using a two hybrid system, an effective agent is identified by an altered level of transcription of a reporter gene (see Fields and Song, Nature 340:245–246 (1989), which is incorporated herein by reference). For example, the level of transcription of a reporter gene due to the bridging of a DNA-binding domain p/CIP or NCoA-2 polypeptide hybrid and a transactivation domain-second protein hybrid can be determined in the absence and presence of an agent.

In some cases, an agent may not be able to cross the yeast cell wall and, therefore, cannot enter a yeast cell to alter the association of a p/CIP or NCoA-2 polypeptide with the second protein. The use of yeast spheroplasts, which are yeast cells that lack a cell wall, can circumvent this problem (Ausubel et al., supra, 1994), which is incorporated herein by reference). In addition, an agent, upon entering a cell, may require "activation" by a cellular mechanism, which may not be present in yeast. Activation of an agent can include, for example, metabolic processing of the agent or a modification such as phosphorylation of the agent, which can be necessary to convert the agent into an effective agent. In this case, a mammalian cell line can be used to screen a panel of agents. A transcription assay such as the yeast two hybrid system described in Example I can be adapted for use in mammalian cells using well known methods (see, for example, Fearon et al., Proc. Natl. Acad. Sci., USA 89:7958–7962 (1992), which is incorporated herein by reference; see, also, Sambrook et al., supra, 1989; Ausubel et al., supra, 1994).

An altered association also can be detected using an in vitro screening assay. In vitro screening assays can utilize, for example, p/CIP or a p/CIP fusion polypeptide such as a histidine-p/CIP fusion protein. For use in an in vitro screening assay, the p/CIP or p/CIP fusion polypeptide should have an affinity for a solid substrate as well as the ability to associate with a second protein. Convenient solid substrates include columns, beads, filters and other materials well known in the art. If desired, the solid substrate can contain a covalently attached anti-p/CIP antibody. Alternatively, when a fusion polypeptide such as a His-p/CIP fusion polypeptide is used in the assay, a nickel chelate substrate, which is bound by the histidine component of the fusion protein, can be used (Invitrogen, Carlsbad, Calif.). Other fusion polypeptide systems are well known in the art and commercially available, including glutathione-S-transferase (GST) fusion polypeptides, which can be immobilized on a glutathione affinity resin (Stratagene, La Jolla, Calif.) or using an anti-GST antibody (DAKO, Carpinteria, Calif.); "FLAG" fusion polypeptides, which can be immobilized on a substrate using anti-FLAG antibody; "AU" fusion polypeptides, which can be immobilized on a substrate using anti-AU antibody, commercially available from Berkeley Antibody Co., Richmond, Calif.; or Myc tag fusion polypeptides, which can be immobilized on a substrate using anti-Myc antibody, commercially available from Invitrogen. As an alternative to immobilization of the p/CIP or NCoA-2 polypeptide, the second protein can be immobilized on a solid substrate using a fusion protein strategy or antibody, as described above.

An in vitro screening assay can be performed by allowing a p/CIP or NCoA-2 polypeptide or p/CIP or NCoA-2 fusion polypeptide, for example, to bind to a solid substrate, then adding the second protein, and an agent to be tested. Control reactions, which do not contain an agent, can be performed in parallel. Incubation is performed under suitable conditions, which include, for example, an appropriate buffer concentration, pH, incubation time and temperature. Subsequently, the association of the p/CIP or NCoA-2 polypeptide and the second protein in the absence and presence of an agent can be detected, for example, by attaching a detectable moiety such as a radionuclide, fluorescent or antigenic label to the p/CIP or NCoA-2 polypeptide, and measuring the amount of label that is associated with the solid support. By comparing the amount of association in the presence of an agent as compared to the control level of association, an effective agent can be identified.

As set forth above, agents to be screened according to a method of the invention can include a variety of biological or chemical compounds such as organic molecules, peptides and peptidomimetics, polypeptides or nucleic acids. In particular, such agents to be screened include fragments of p/CIP or NCoA-2 polypeptides and fragments of CBP proteins or nuclear receptors. Such fragments can be produced by chemical or proteolytic cleavage of the isolated polypeptide. Methods for chemical and proteolytic cleavage and for purification of the resultant polypeptide fragments are well known in the art as described above. (See, for example, Deutscher, *Methods in Enzymology,* Vol. 182, "Guide to Protein Purification," San Diego: Academic Press, Inc. (1990), which is incorporated herein by reference).

A large collection, or library, of chemicals or small molecule drugs also are agents that can be screened according to a method of the invention. Polypeptide libraries, random polypeptides, or polypeptides of interest also are agents that can be screened for activity as disclosed herein. Polypeptide libraries include, for example, tagged chemical libraries comprising peptides and peptidomimetic molecules. Polypeptide libraries also comprise those generated by phage display technology. Phage display technology includes the expression of polypeptide molecules on the surface of phage as well as other methodologies by which a protein ligand is or can be associated with the nucleic acid which encodes it. Methods for production of phage display libraries, including vectors and methods of diversifying the population of peptides which are expressed, are well known in the art (see, for example, Smith and Scott, *Methods Enzymol.* 217:228–257 (1993); Scott and Smith, *Science* 249:386–390 (1990); and Huse, WO 91/07141 and WO 91/07149, each of which is incorporated herein by reference). These or other well known methods can be used to produce a phage display library which can be screened, for example, with one of the disclosed assays to identify an effective agent that alters the association of a p/CIP or NCoA-2 polypeptide with a second protein.

A peptide portion of p/CIP comprising a helical leucine-rich, charged domain (LCD), can inhibit the transcriptional activity of one type of nuclear receptor, such as the retinoic acid receptor, but not of a second, related nuclear receptor such as the estrogen receptor, whereas a second LCD of p/CIP can inhibit signal transduction induced by interferon γ, but not signal transduction induced by retinoic acid. Thus, selected peptide portion of p/CIP or of an NCoA can be useful for selecting regulating gene expression in a cell. Because of the central nature of p/CIP, NCoA proteins, CBP/p300 and the various transcription factors that form the complexes disclosed herein, an agent such as an LCD peptide can be used to treat various pathologic conditions. For example, the transcriptional activity of CBP/p300-dependent proteins belonging to the AP-1 and ets families of transcription factors can be specifically inhibited, thereby providing a means to reduce or prevent the severity of inflammatory diseases or of cancer. In addition, selective activities of nuclear receptors can be potentiated or inhibited, providing beneficial effects in patients suffering from inflammatory disorders, breast cancer or osteoporosis. Also, inhibition of NF-κB dependent transcription can provide a benefit to patients having an inflammatory disorder or atherosclerosis. Thus, an agent that alters the association of a p/CIP or of NCoA-2 polypeptide with CBP/p300 or with a CBP/p300-dependent transcription factor, or alters the ability of such proteins to form a complex, is useful as a medicament for treating a pathologic condition.

The ability of nuclear receptor coactivator (NCoA) polypeptides such as p/CIP to interact with nuclear receptors in a ligand-dependent manner provides the basis of a method for identifying a ligand of a nuclear receptor from a library of one or more test agents. If desired, a nuclear receptor corepressor (NCoR) can be used in place of a NCoA polypeptide. A method of the invention can be useful for identifying a ligand for a nuclear receptor having a previously identified physiologic ligand or for identifying a ligand of an orphan receptor having no previously identified ligand. Thus, the invention provides a method for identifying a ligand for a nuclear receptor, including the steps of contacting a NCoA polypeptide, or nuclear receptor binding fragment thereof, and a nuclear receptor with an agent under conditions that allow the NCoA polypeptide to associate with the nuclear receptor; and detecting an altered association between the NCoA polypeptide, or nuclear receptor binding fragment thereof, and the nuclear receptor, where an increased association indicates that the agent is an agonistic ligand of the nuclear receptor and a decreased association indicates that the agent is an antagonistic ligand of the nuclear receptor. One skilled in the art understands that the altered association in the presence of the agent is compared to the association in the absence of the agent.

The term "NCoA polypeptide," as used herein, means a nuclear receptor coactivator protein that is characterized, in part, as containing one or more "LXXLL" motifs and by its ability to mediate ligand-dependent nuclear receptor activation. A NCoA polypeptide can be, for example, a SRC-1/NCoA-1, p/CIP or NCoA-2 polypeptide, or a polypeptide having substantial similarity to one of these polypeptides. A NCoA polypeptide can have, for example, at least about 30% amino acid identity with a SRC-1/NCoA-1, p/CIP or NCoA-2 polypeptide and, further, can have at least about 40%, 50%, 60%, 70%, 80% or 90% amino acid identity with a SRC-1/NCoA-1, p/CIP or NCoA-2 polypeptide.

The agent to be tested for agonist or antagonist activity can be provided in purified form, or in impure form as a pool of different agents. As described above, an agent can be a biological or chemical compound such as a simple or complex organic molecule, a peptide, a peptidomimetic, a polypeptide or a nucleic acid. The nuclear receptor can be, for example, a steroid hormone receptor, retinoid receptor or fatty acid metabolite receptor. Retinoic acid receptors, estrogen receptors, progesterone receptor and thyroid receptors are examples of nuclear receptors useful in the claimed methods. The NCoA polypeptide can be, for example, a p/CIP, NCoA-1 or NCoA-2 polypeptide, or an active fragment of a NCoA polypeptide with nuclear receptor binding activity. Active p/CIP and NCoA-2 polypeptides including a nuclear receptor interaction domain have been described hereinabove. Such a fragment can be, for example, a LCD peptide that contains one or more LXXLL motifs. In the presence of an agent that is an agonist, the nuclear receptor can undergo a conformational change, whereby there is an increased association of the nuclear receptor with the NCoA polypeptide or nuclear receptor interaction domain thereof, or with another coactivator containing one or more LXXLL motifs.

In one embodiment, the nuclear receptor can be immobilized on a solid substrate, for example, by expressing the nuclear receptor as a GST fusion protein and capturing the fusion protein on a glutathione affinity matrix. The nuclear receptor fusion protein can be incubated, for example, with labeled NCoA polypeptide such as labeled p/CIP polypeptide in the presence of an agent to be tested. Following incubation and subsequent washing of the glutathione affinity matrix, specifically bound NCoA polypeptide can be detected quantitatively, semi-quantitatively, or qualitatively. In the presence of a ligand that is an agonist, the association of the p/CIP or other NCoA polypeptide with the GST matrix is increased. Conversely, in the presence of a ligand that is an antagonist of the nuclear receptor, the association of the NCoA polypeptide with the GST matrix is decreased.

As set forth above, a NCoA polypeptide such as p/CIP can be labeled with a variety of labels including fluorescent labels or radiolabels such as $^{35}$S-labeled amino acids, which can be incorporated by in vitro translation using a rabbit reticulocyte translation system. A LCD peptide containing at least one LXXLL motif also can be used, if desired, in place of or in addition to, the NCoA polypeptide. Such a LCD peptide can be modified to contain N- or C-terminal tyrosine residues that do not substantially influence interaction with the nuclear receptor but which can be conveniently labeled, for example, using radioiodination. A short sequence tag suitable for phosphorylation of an LCD peptide with $^{32}$P-ATP also can be used as a label. Fluorescent detection, for example using green fluorescent protein, can be particularly useful in the methods of the invention. Useful fluorescent detection methods include florescence polarization as well as fluorescence resonance energy transfer (FRET)-based assays. FRET-based assays are particularly advantageous for high throughput screening approaches since such assays are homogeneous and do not require a washing step and, in addition, can be useful for detecting nuclear receptor interactions within a cell.

In the methods of the invention, the ligand to be identified can be an antagonist. The present invention provides, for example, a method of identifying an antagonist of a nuclear receptor. The method includes the steps of contacting a NCoA polypeptide or nuclear receptor interaction domain thereof and a nuclear receptor with an agonist of the nuclear receptor and an agent under conditions that allow the NCoA polypeptide or nuclear receptor interaction domain thereof to associate with said nuclear receptor; and detecting an altered association of the NCoA polypeptide or nuclear receptor interaction domain thereof and the nuclear receptor, where a decreased association indicates that the agent is an antagonist of the nuclear receptor. An agent that is an antagonist can compete with the agonist for binding to the nuclear receptor without inducing the conformation change required for interaction of the NCoA polypeptide, or nuclear receptor interaction domain thereof, and the nuclear receptor. As described above, a LCD peptide containing one or more LXXLL motifs can be substituted for a NCoA polypeptide in the methods of the invention.

In a further embodiment, the invention provides a method of identifying a ligand with mixed agonist and antagonist properties with respect to a particular nuclear receptor. Such a method includes the steps of: contacting a first NCoA polypeptide, or nuclear receptor interaction domain thereof, and a nuclear receptor with an agent to form a first complex; detecting an altered association of the first complex in the presence and absence of the agent; contacting a second NCoA polypeptide, or nuclear receptor interaction domain thereof, and a nuclear receptor with the agent to form a second complex; and detecting an altered association of the second complex in the presence and absence of the agent, wherein an increased association of the first complex combined with a decreased association of the second complex or a decreased association of the first complex combined with an increased association of the second complex indicates that the agent is a ligand of the nuclear receptor having mixed agonist and antagonist activity. A ligand identified by this method can be particularly useful since it can exhibit different effects on nuclear receptor function in different cell types and can be useful for differentially modulating different classes of transcription factors.

The following example is intended to illustrate but not limit the present invention.

EXAMPLE I

Identification and Characterization of p/CIP

This example provides methods for isolating and characterizing the nucleic acid molecule encoding p/CIP, which regulates the activity of CBP/p300-dependent transcription factors. Additional details related to these methods are provided in Torchia et al., June 1997 (Nature), which is incorporated herein by reference.

A. Materials and Methods

1. Isolation of Interacting Proteins

Expression cloning was performed, using a $^{32}$P-labeled GST-CBP (2058–2170) or $^{32}$P-labeled GST-ER ligand binding domain probe in the presence of $10^{-6}$ M estradiol (Kamei et al., Cell 85:1–12 (1996), which is incorporated herein by reference). cDNA's corresponding to p/CIP, NCoA-1 and NCoA-2 were assembled into PCMX and tested by in vitro translation, generating products which all migrated at approximately 160 kDa. Databank accession numbers for p/CIP and NCoA-2 sequences are AF000581 (p/CIP) and AF000582 (NCoA-2), each of which is incorporated herein by reference.

2. Yeast Two-hybrid Interaction Assays

The yeast strain EGY 48, the LexA-β-galactosidase reporter construct (PSH 18–34) and the B42 parental vectors (pEG 202 and pJG 4–5) were all previously described (Gyuris et al., Cell 75:791–803 (1993), which is incorporated herein by reference; Kamei et al., supra, 1996). Nuclear receptor ligand binding domains and various CBP fragments were subcloned into PEG 202 bait vector. DNA fragments encompassing the entire p/CIP-NCoA-1 or NCoA-2 proteins were generated either by using an appropriate restriction digest or by PCR and subcloned into pJG 4–5 prey vectors. EGY 48 cells were transformed with the lac Z reporter plasmid pSH 18–34 with the appropriate bait and prey vectors and plated out on -Ura-His-Trp medium containing 2% galactose. Isolated yeast colonies were allowed to grow in the same liquid medium, followed by assaying for β galactosidase, as previously described (Ausubel et al., supra, 1994).

3. Transient Transfections and Reporter Assays

Transfection experiments were conducted in either HELA or CV-1 cells using the standard calcium phosphate procedure. Typically, 1 ug of a RARE- or ERE-driven luciferase reporter were cotransfected with 1 ug of the indicated vectors. The final DNA concentration was adjusted to 10 ug/60 mm dish, incubated for 24 hr, then the appropriate ligands were administered for 24 hr at a concentration of $10^{-6}$ M. Alternatively, cotransfection experiments were conducted using a PCMX p/CIP, NCoA-1 or PCR-generated NCoA-1 fragments fused to the GAL 4 DNA binding domain (aa 1–147). Cells were transfected with 1 ug of a (UAS)$_6$-luciferase reporter and the indicated concentrations of GAL4 fusion proteins, then harvested 48 hrs later.

4. Affinity Purified NCoA Antibodies and Peptides cDNA fragments corresponding to p/CIP (544–851), NCoA-1 (424–789) or NCoA-2 (787–1129) were subcloned into the pM vector containing an in-frame His tag and recombinant His-tagged proteins were generated and purified by nickel chelate chromatography. The purified recombinant proteins were injected into rabbits and antibodies were generated and affinity purified using standard procedures (Harlow and Lane, supra, 1988. Peptide sequences were generated (Research Genetics) and confirmed by mass spectrosopy analysis, including NCoA-1 LCD1 (aa 631–647); NCoA-1 LCD2 (687–706); NCoA-1 LCD4 (aa 907–926); CBP N'-P1 (aa 1–19); and CBP N'-P2 (aa 8–19).

5. Interaction Assays, Immunoprecipitations and Enzymatic Assays

Whole cell extracts were prepared by lysing the cells in NET-N buffer containing 50 mM Tris (pH 7.6), 5 mM EDTA, 0.3 M NaCl, 1 mM DTT, 0.1% NP-40 and protease inhibitors (0.2 mM PMSF, 10 ug/ml each of leupeptin, pepstatin and aprotinin), centrifuged at 30,000×g for 1 hr at 4° C. and the supernatant was stored at −80° C. until use.

GST-RAR (143–462), GST-ER(251–595) and GST-CBP (2058–2170) were generated as described (Kamei et al., supra, 1996). 25 ul of GST SEPHAROSE beads containing 10 ug of the GST recombinant proteins were incubated in the presence or absence of the appropriate ligand for 30 min at room temperature, followed by the addition of 1 mg of cell extract and incubated for an additional 1 hr at 4° C. The complexes were then centrifuged, washed three times in NET-N buffer, separated by SDS-PAGE and western blotted with the appropriate antibodies (1 ug/ml). For co-immunoprecipitation assays, 1 mg of cell extract was incubated in the presence of 2 ug of p/CIP or NCoA antibody for 2 hr at 4° C. The immune complexes were precipitated with protein A SEPHAROSE (50% w/v). Protein complexes were separated by SDS-PAGE (Laemmle, Nature 227:680–685 (1970), which is incorporated herein by reference) and western blotted using 1 ug/ml of an anti-CBP/P300 monoclonal antibody (UBI). For in vitro competition assays, the indicated peptides were incubated with in vitro translated NCoA-1 prior to GST interaction with RAR.

6. Mutagenesis

Mutations in NCoA-1 and CBP were introduced by site-directed mutagenesis using the quick change mutagenesis kit according to the manufacturers instructions (Stratagene; La Jolla Calif.). Double stranded oligonucleotides were designed such that the wild type sequence corresponding to amino acids 695 to 698 and amino acids 756 to 759 in pCMX NCoA-1 and pJG-4-5-4 NCoA-1 (aa 635-760) were substituted with alanines. A similar protocol was used to replace amino acids 70 to 73 in PJG4–5 CBP(aa 1–101).

7. Single Cell Microinjection Assay

Insulin-responsive Rat-1 fibroblasts were seeded on acid washed glass coverslips at subconfluent density and grown in MNE/F12 medium supplemented with 10% fetal bovine serum, gentamicin and methotrexate. Prior to the injection, the cells were rendered quiescent by incubation in serum-free medium for 24–36 hr. Plasmids were injected into the nuclei of cells at a final concentration of 100 mg/ml. Peptides were injected at a concentration of 200 mM. Either preimmune IgG of the appropriate species or antibodies directed against p/CIP, NCoA-1 or NCoA-2 were co-injected and allowed the unambiguous identification of the injected cells.

Microinjections were carried out using an Eppendorf semiautomated microinjection system mounted on an inverted Zeiss microscope. Approximately 1 hr after injection, the cells were stimulated, where indicated, with the appropriate ligand. In the case of rescue experiments, the cells were stimulated with ligand 6 hr after injection, to allow protein expression. After overnight incubation, the cells were fixed, then stained to detect injected IgG and β-galactosidase expression (Rose et al., J. Cell. Biol. 119: 1405–1411 (1992), which is incorporated herein by reference; Kamei et al., supra, 1996). Injected cells were identified by staining with tetramethylrhodamine-conjugated donkey anti-rabbit IgG.

B. Results

1. Identification of Novel Members of the Nuclear Receptor Co-Activator Family

Figure 2C:
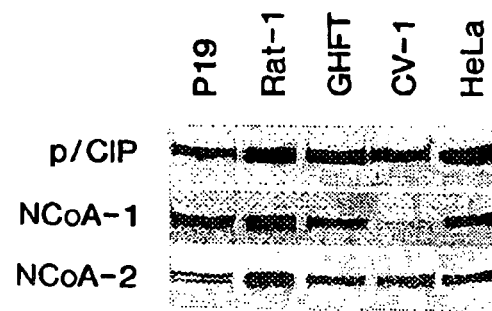
Figure 2D:
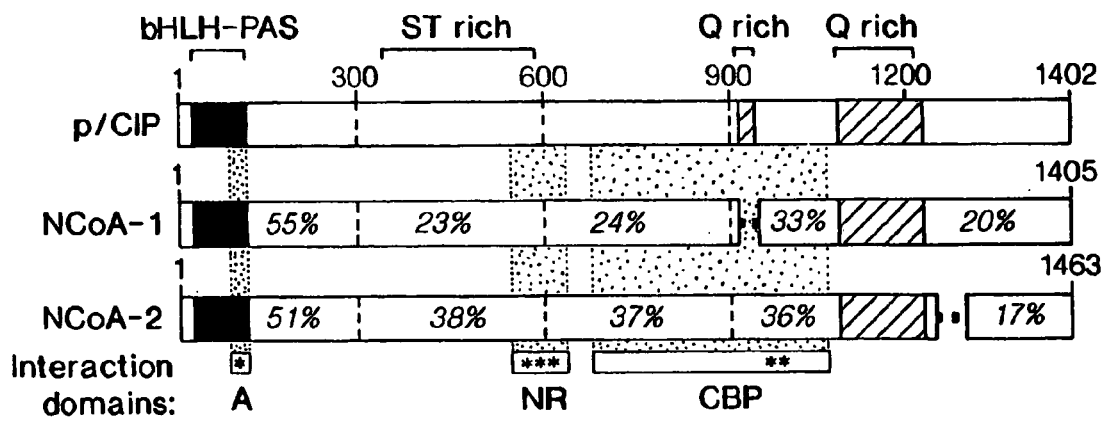

The initial expression screening strategy for identifying members of the p160 gene family was based on the observation that the biochemically-identified p160 proteins interacted with a 100 amino acid region in the C-termini of CBP (aa 2058–2170), as well as the liganded estrogen receptor (ER; Ogryzko et al., Cell 87:953–960 (1996), which is incorporated herein by reference). This strategy allowed isolation of the previously reported NCoA-1/SRC-1 protein and of a second related factor, NCoA-2 (FIG. 2a), which has a molecular mass of 159.6 kDa and appears to be the murine homologue of the human TIF-2, a portion of which has been recently reported as GRIP-1 (Voegel et al., EMBO J. 15(14): 3667–3675 (1996); Hong et al., Proc. Natl. Acad. Sci. USA 93:4948–4952 (1996), each of which is incorporated herein by reference). In addition, a related factor was identified and is designated herein as p300/CBP/Co-Integrator-Associated protein.

p/CIP is a 152 kDa protein that is highly related to SRC-1/NCoA-1 and NCoA-2/TIF-2, showing an overall amino acid identity of 31% and 36%, respectively (FIG. 2a). p/CIP has a conserved N-terminal bHLH, PAS "A" domain (50–60% amino acid identity), a serine/threonine threonine rich region, and a C-terminal glutamine-rich region, each of which also is present in NCoA-1 and NCoA-2. Western blot analysis indicates that p/CIP, NCoA-1 and NCoA-2 are widely expressed in adult tissues and in all cell lines evaluated (FIGS. 2b and 2c).

2. A CBP/pCIP Complex

To evaluate the association of p/CIP, NCoA-1, and NCoA-2 with CBP and nuclear receptors, GST-CBP (2058–2170) was used to affinity purify interacting proteins from HeLa cell extracts. p/CIP was consistently observed by immunoblotting using affinity purified anti-p/CIP IgG, whereas much smaller amounts of NCoA-1 were detected following immunoblotting with anti NCoA-1 IgG (FIG. 3a). Similarly, immunoprecipitations from whole cell extracts using excess antisera selective for each protein, followed by immunoblotting with anti-CBP/p300 antibody, demonstrated that the vast majority of CBP/p300 coprecipitated with p/CIP, although small amounts of NCoA-1- and NCoA-2-associated CBP were detected (FIG. 3b). Conversely, the amount of CBP/p300 remaining in the supernatant fraction following immunodepletion with anti-NCoA-1 IgG remained unchanged, while a significant fraction of CBP was removed following immunodepletion with anti-p/CIP IgG (FIG. 3b). These results indicate that p/CIP forms a complex with CBP in the cell.

To further define the CBP interaction domain in p/CIP, deletion mutants were generated and tested against CBP (2058–2170) using a yeast two-hybrid assay. The major CBP interaction domain was located between amino acids 758 to 1115 of p/CIP, with an internal 200 amino acid domain still capable of interacting. Interestingly, a less pronounced interaction was observed with the N-terminal region containing the PAS "A" domain (FIG. 3c). A single nuclear receptor interaction domain (aa 591–803) was localized N-terminal of the CBP/p300 interaction domain (FIG. 3c). Further mapping delineated a minimal nuclear receptor interaction region encompassing amino acids 680–740 in p/CIP that was sufficient for binding to the liganded nuclear receptors. Comparable regions in NCoA-1 and NCoA-2 were found to mediate interactions with both CBP/p300 and nuclear receptors (FIG. 3d). GST pull-down assays of whole cell extracts revealed that p/CIP, NCoA-1, and NCoA-2 interacted with GST-ER and GST-RAR in a ligand-dependent manner (FIG. 3e).

Cotransfection with NCoA-1/SRC-1 or NCoA-2/TIF-2 expression vectors clearly potentiated ligand-dependent activation events (generally 3-fold to 8-fold), while cotransfection with p/CIP expression plasmids resulted in minimal or no activation effects (FIG. 3f, left). In addition, when full length cDNA's were fused to GAL4(1–147), the activation observed by GAL-NCoA-1 was significantly stronger than GAL-p/CIP (FIG. 3f, right). Cotransfection of CBP and NCoA-1 or NCoA-2 expression vectors resulted in variable synergy (data not shown), consistent with previous findings reported for SRC-1 (Smith et al., Proc. Natl. Acad. Sci., USA 93:8884–8888 (1996)).

To investigate the functional roles of p/CIP, NCoA-1 and NCoA-2, microinjection studies were performed, using the affinity-purified IgG's. Reporter genes were placed under the control of a minimal promoter containing either nuclear receptor or other response elements (Kamei et al., supra, 1996). Microinjection of anti-p/CIP IgG eliminated the ability of retinoic acid to activate an RAR-dependent transcription unit (FIG. 4a), but was without effect on a promoter under the control of SP-1 elements or the CMV promoter. In similar experiments, p/CIP also was required for the actions of estrogen, thyroid hormone and progesterone receptors (FIG. 4b).

To determine whether depletion of CBP, rather than p/CIP itself, was responsible for the observed effects, the relative abilities of p/CIP, CBP, NCoA-1, and/or NCoA-2 to rescue the inhibitory effect of anti-p/CIP IgG was evaluated. No factor alone, including CBP, was able to rescue the inhibitory effect of anti-p/CIP IgG on RAR-dependent transcription, indicating that steric blockage or removal of CBP did not account for the observed effects. However, the simultaneous expression of both p/CIP and CBP fully restored retinoic acid transcriptional response in anti-p/CIP-treated cells (FIG. 4c). These results indicate that both CBP and p/CIP are required together for nuclear receptor activation.

To independently confirm the need for p/CIP, the effect of a 137 amino acid region of p/CIP (aa 947–1084) containing the core CBP interaction domain was tested by microinjection assays. This peptide completely inhibited retinoic acid-dependent gene activation (FIG. 4d; left), but did not block the activity of non-CBP-dependent promoters (FIG. 4d; right).

Figures 1, 4E:
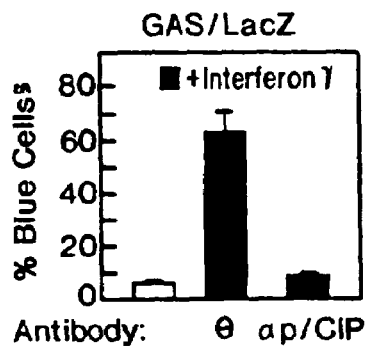
FIG. 4e shows the effect of anti-p/CIP IgG (α p/CIP) on an interferon γ dependent promoter (GAS/LacZ)[12] (left) and the effect of p/CIP (aa 947–1084) on interferon γ stimulated transcriptions and failure of CBP expression vector to rescue this inhibition (right).
Figures 2, 4E:
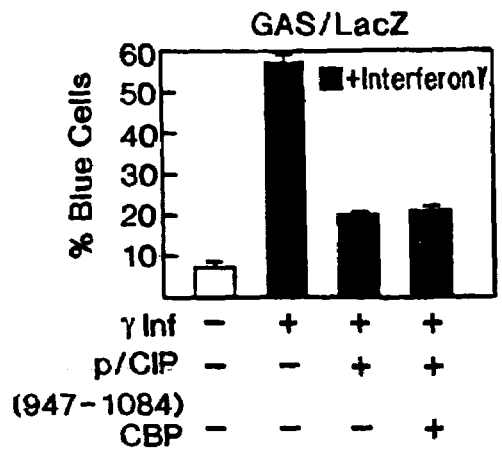

The requirement of p/CIP for transcriptional activation by other CBP-dependent transcription factors, such as STAT also was examined (Bhattacharya et al., Nature 383:344–347 (1996); Zhang et al., Proc. Natl. Acad. Sci., USA 93:15092–15096 (1996); Horvai et al., Proc. Natl. Acad. Sci., USA 94:1074–1079 (1997)). The effect of anti-p/CIP and NCoA-1 IgG was evaluated by immunoinjection assay in cells, initially using interferon γ-dependent or TPA-dependent reporters. Anti-p/CIP IgG entirely inhibited the STAT-dependent and TPA-dependent transcriptional activation events (see FIG. 4e) and the inhibition was not restored by overexpression of CBP, alone. Independent confirmation was provided by over-expression of the CBP interaction domain of p/CIP (aa 947–1084), which blocked the ability of interferon γ or of TPA to stimulate transcriptional activation (FIG. 4e). Further, C-terminally truncated CBP failed to enhance either interferon γ- or TPA-dependent transcription in cotransfection assays and could not rescue the block of retinoic acid- and interferon γ-dependent gene activation by injected anti-CBP IgG (Kamei et al., supra, 1996; Horvai et al., supra, 1997). These results indicate that p/CIP and CBP represent a functional complex, required for function by several CBP-dependent transcription factors in addition to nuclear receptors.

3. Roles of NCoA-1 and NCoA-2 in Nuclear Receptor Activation

Figures 1, 4F:
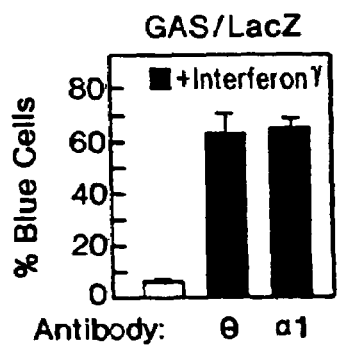
FIG. 4f shows the effect of anti-NCoA-1 IgG (α1) on GAS and cAMP-dependent (2×CRE) promoters. All were performed at least three separate times, with >200 cells injected; error bars are ±2×SEM.
Figures 2, 4F:
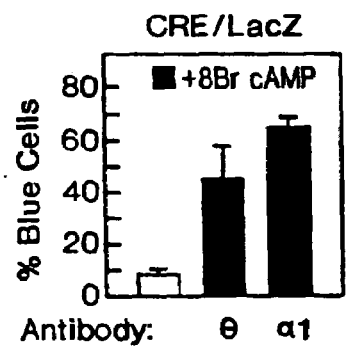
Figures 1, 5A:
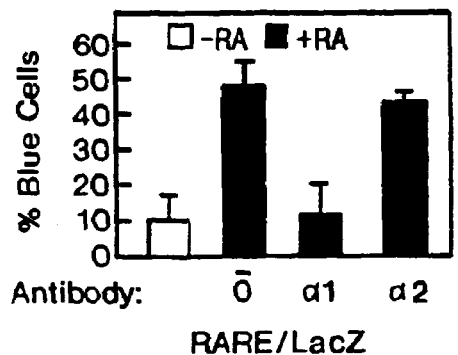
FIG. 5a demonstrates that microinjection of affinity-purified anti-NCoA-1, but not of anti-NCoA-2, IgG blocked ligand-dependent gene activation by RAR (left), but did not inhibit expression of either the 6×SP-1 or CMV-driven promoters (right).
Figures 2, 5A:
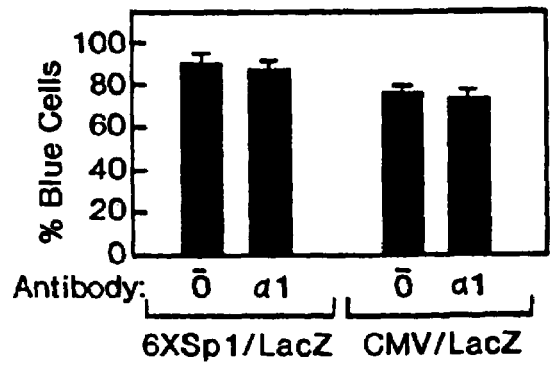
Figures 1, 5B:
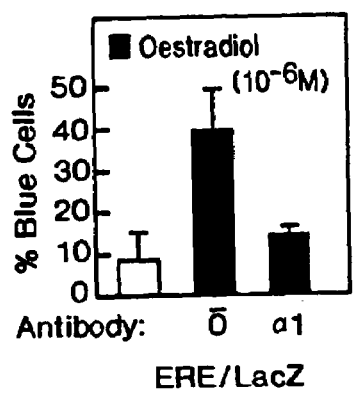
FIG. 5b shows experiments as in FIG. 5a, except using minimal promoters with two copies of the estrogen (ERE) or T3R (TRE) response elements with less profound effects upon progesterone (PRE) mediated transcription.
Figures 2, 5B:
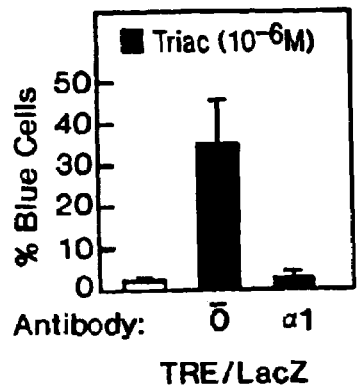
Figures 3, 5B:
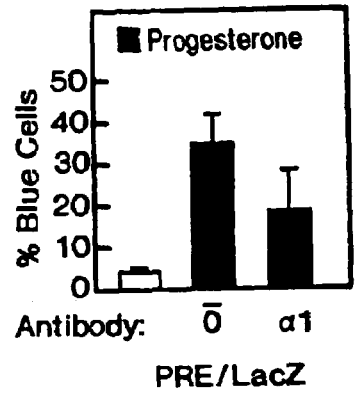
FIG. 3 shows the results of biochemical analysis of p/CIP and NCoA Factors.
Figure 5C:
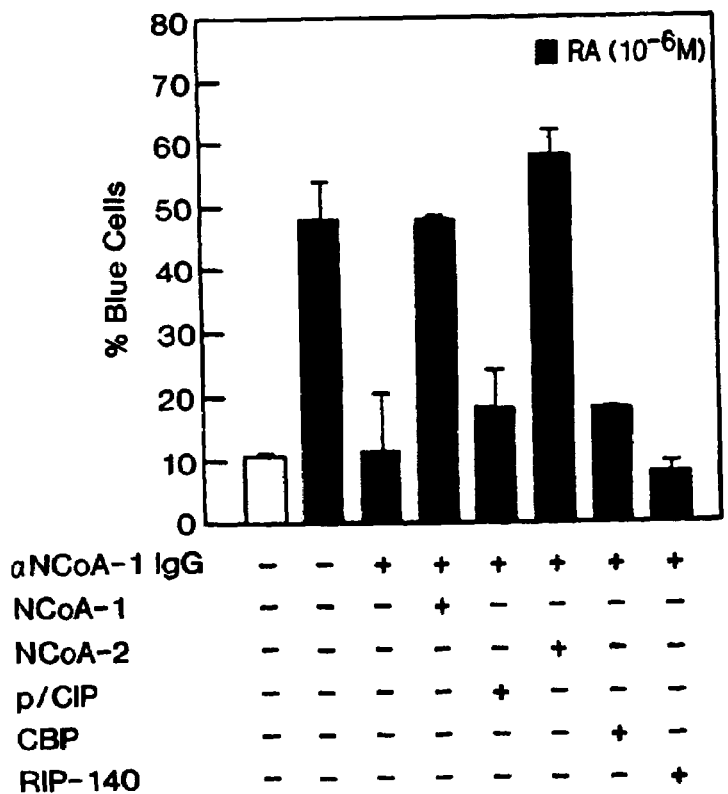
FIG. 5c demonstrates that anti-NCoA-1 IgG blocked retinoic acid-dependent activation of the RARE/LacZ reporter was not rescued by CMV expression vectors expressing p/CIP or CBP; however, expression was fully rescued by CMV-NCoA-1 and b CMV-NCoA-2.
Figure 5D:
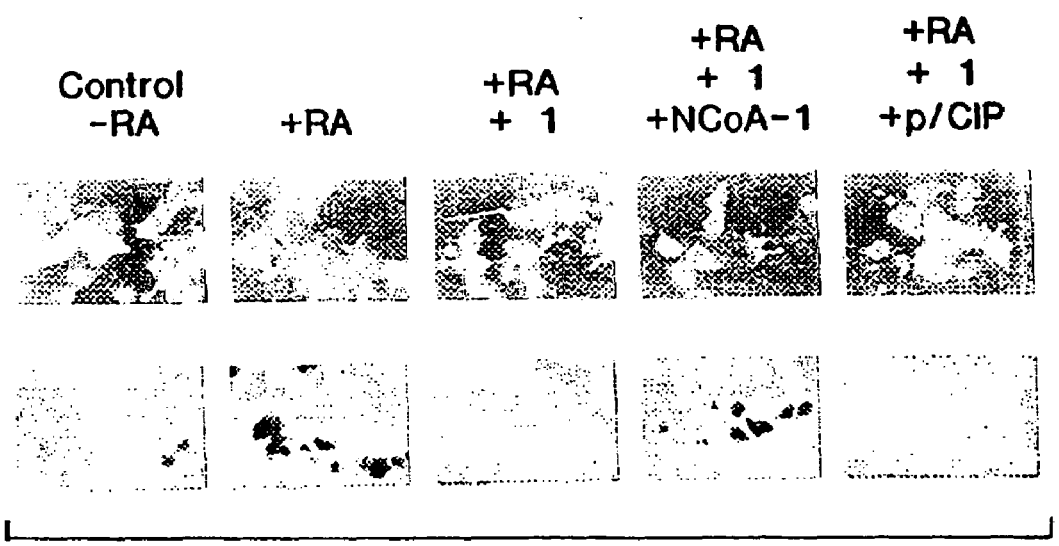
FIG. 5d shows photomicrographs of rhodamine-stained injected cells and the corresponding protein of XGal staining.

Based on the requirement for p/CIP in both nuclear receptor and several CBP/p300-dependent transcription factors, it was important to evaluate the precise roles of NCoA-1/SRC-1 and NCoA-2/TIF-2, which, by cotransfection, enhance transactivation by nuclear receptors. Microinjection of anti-NCoA-1 IgG, but not of anti-NCoA-2 IgG, effectively inhibited retinoic acid-dependent transcription (FIG. 5a), while these antisera failed to inhibit several control promoters that lacked nuclear receptor response elements (FIG. 5a). In addition, anti-NCoA-1 IgG fully inhibited estrogen and thyroid hormone receptor stimulation (FIG. 5b) and partially inhibited progesterone receptor stimulation (FIG. 5b). Co-injection of NCoA-1, NCoA-2 or p/CIP expression vectors revealed that the inhibitory effects of anti-NCoA-1 IgG could be entirely reversed by either NCoA-1 or NCoA-2, but not by p/CIP (FIG. 5c), consistent with a distinct role for this factor, and in contrast to the requirement for both p/CIP and CBP to rescue the inhibitory actions of anti-p/CIP IgG. Co-injection of a CMV-CBP expression vector also failed to restore activity, consistent with the model that both NCoA-1 and the CBP/p300/p/CIP complex are independently required for nuclear receptor gene activation events (FIG. 5c). In contrast, anti-NCoA-1 IgG exerted no effects on either cAMP- or interferon γ-dependent reporters (FIG. 4f). These results indicate that NCoA-1 is selectively required as a coactivator for the ligand-activated nuclear receptor gene expression events; the requirement for the CBP/p300/p/CIP complex reflects a more general obligatory role in gene activation events.

Figure 6A:
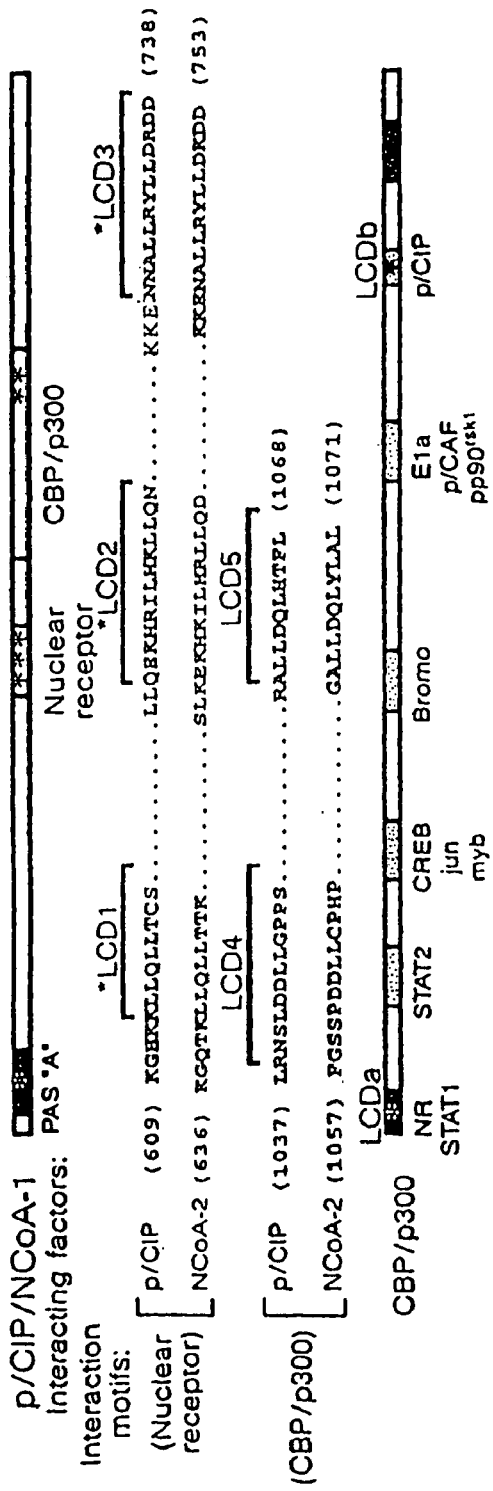
FIG. 6a shows that a repeated leucine-rich domain is required for protein-protein interactions between p/CIP, CBP, NCoA proteins and nuclear receptors. The sequence of some of these domains are noted (SEQ. ID NO: 2aa 609–684, 723–738, 1037–1049, 1058–1068; SEQ. ID NO: 3, aa 638–648, 682–696, 739–753, 1057–1069, 1078–1088; SEQ. ID. NO: 4 to SEQ ID NO: 9) with the core hexapeptide motifs indicated by brackets. Helical wheeels of NCoA-1 LCD2 (SEQ. ID NO: 10) and CBP LCD6 (SEQ. ID NO: 11) are shown.

4. Interaction Motifs of the Co-Integrator Complex Selectively Inhibit Transcriptional Effects of Distinct Signal Transactivation Pathways In view of the relatedness of NCoA-1 and p/CIP, despite the apparent distinctions in their functional roles, and the involvement of CBP/p300 in activation of different classes of transcription factors, the ability of distinct interaction domains to selectively block the actions of specific signal transduction pathways at a nuclear level was examined. Delineation of the nuclear receptor interaction domains of p/CIP, NCoA-1, and NCoA-2 revealed the presence of highly conserved leucine, charged residue-rich domains (LCD's) that share a consensus core sequence, LXXLL (FIG. 6a). This motif is found in both the nuclear receptor and the p/CIP interaction domains of CBP and in the CBP interaction domain of p/CIP.

Analysis of these putative interaction regions by the self-optimized prediction method (SOPM; Geourjon and Deleage, *Protein Engineering* 7:157–164 (1994), which is incorporated herein by reference) strongly suggested that they represent helical domains, generally with amphipathic characteristics (FIG. 6a). To begin to investigate whether these LCD's exert a critical interaction function, four amino acid mutations of this motif were introduced into the N-terminus of CBP (aa 65–76), abolishing interactions with nuclear receptors (FIG. 6b). The minimal nuclear receptor interaction domain of NCoA-1 contains three such helical motifs, and a fourth such motif (LCD6) also is present in a variant of NCoA-1 (Onate et al., *Science* 270:1354–1357 (1995); Kamei et al., supra, 1997).

To assess the importance of these motifs in NCoA-1, a smaller region lacking helical domain 3 resulted in little or no decrease in binding to either estrogen or retinoic acid receptors, while deletion of helical domain 1 exhibited a small but significant decrease (FIG. 6c). In contrast, a four amino acid substitution in the second NCoA-1 helical domain (LCD2; HRLL (SEQ ID NO: 5, aa 10–13)->AAAA (SEQ ID NO: 13, aa 3–6)), which would alter the properties of this helix, abolished interaction with both estrogen and retinoic acid receptors. Conversely, a 37 amino acid region of NCoA-1 containing LCD2, or 59 amino acids containing LCD6, was sufficient for binding to liganded nuclear receptors (FIG. 6c, left). The addition of an excess 24 mer oligopeptide encompassing LCD2 effectively blocked interactions between liganded RAR and NCoA-1 in vitro; whereas a peptide corresponding to LCD 1 was less effective. These results indicate that specific motifs can be both required and, in certain instances, sufficient, for interaction.

Figure 6D:
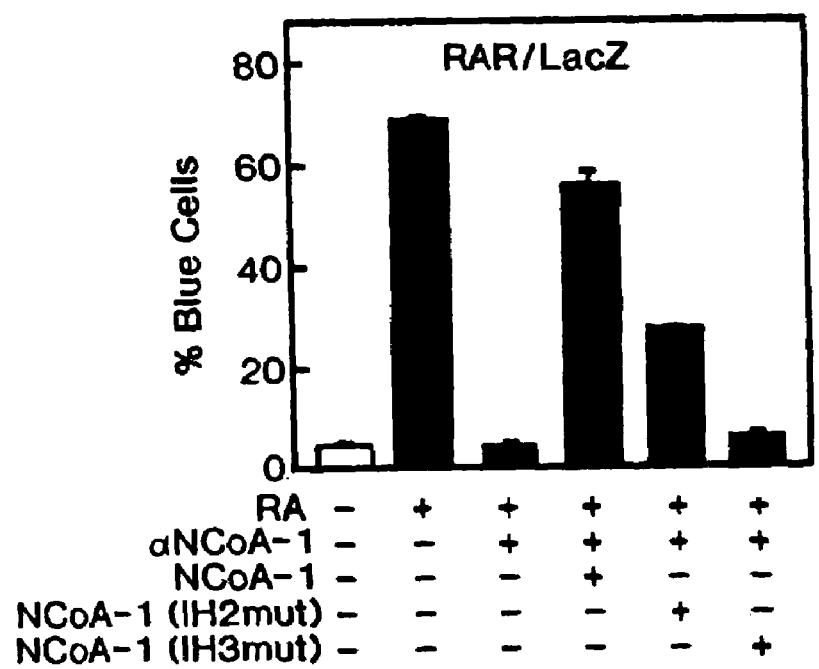
FIGS. 6d and 6e demonstrate the functional effect of plasmids expressing mutations in LCD2 (HRLL (SEQ ID NO: 5, aa 10–13)->AAAA (SEQ ID NO: 12, aa 3–6)) and LCD3 (RYLL (SEQ ID NO: 6., aa 8–11)->AAAA (SEQ ID NO: 13)) of NCoA-1 on rescue of inhibition by microinjected anti-NCoA-1 IgG (.alpha.-1) on retinoic dependent transcription (FIG. 6d) and on estrogen dependent transcription (FIG. 6e).
Figure 6E:
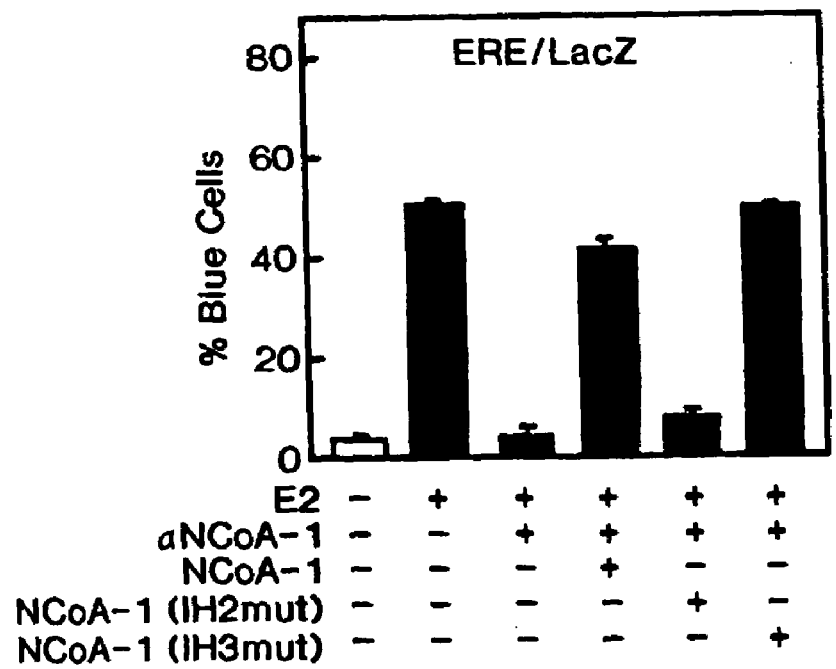

To assess the potential selective functional requirements of these helical motif sequences in the nuclear receptor interaction domain of NCoA-1, mutations in helical domains 2 or 3 were generated in the context of the holoprotein and tested for the ability to rescue anti-NCoA-1 IgG inhibition of retinoic acid receptor function. Whereas wild-type NCoA-1 fully rescued activation, an NCoA-1 holoprotein harboring clustered point mutations in helical domain 3 (LCD3-mut) was completely ineffective at rescuing retinoic acid receptor function. NCoA-1 containing a helical domain 2 (LCD2-mut) mutation retained some residual efficacy (FIG. 6d), consistent with the residual ability of the helical domains to mediate nuclear receptor interactions. Surprisingly, however, NCoA-1 harboring the helical domain 3 mutation (LCD3-mut) retained full functional ability in estrogen receptor-dependent gene activation, whereas LCD2-mut was completely ineffective at rescuing estrogen receptor function (FIG. 6e). These results indicate that the helical interaction motifs of NCoA-1 afford a level of receptor specificity.

Figure 7D:
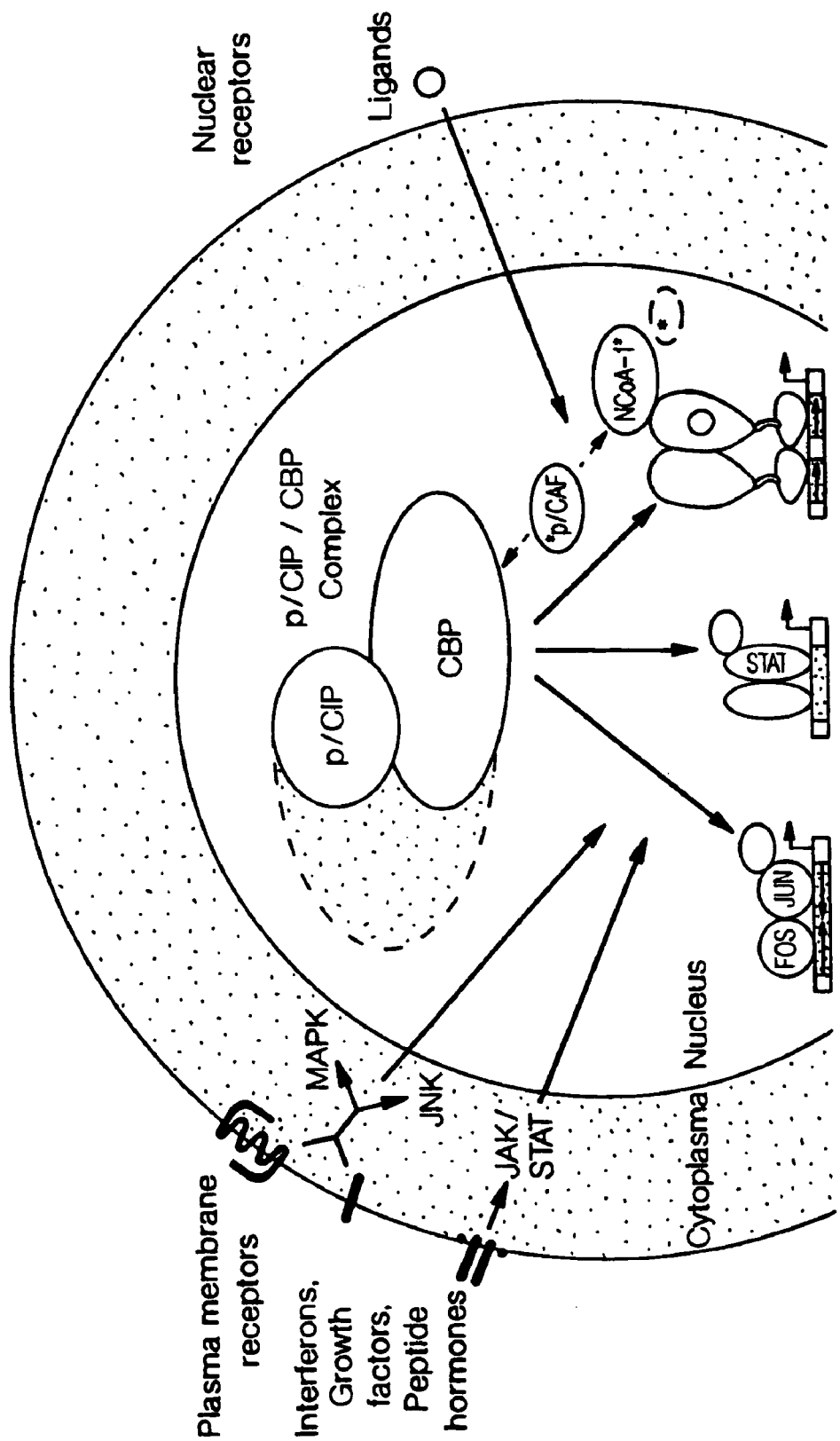
FIG. 7d provides a model of p/CIP/CBP (p300) function, indicating that several signal transduction pathways mediated by specific transcription factors require a functional p/CIP, CBP/p300 complex, and potentially p/CAF, with each partner required, but not sufficient, to mediate transcriptional effects. Nuclear receptor-specific requirements for distinct protein-protein associations via specific LCD's is suggested.

To independently assess the importance of these motifs, corresponding peptides were tested for their ability to inhibit specific activation events. NCoA-1 harbors two additional related helical interaction motifs, and a peptide encompassing one of these motifs (LCD4) can block nuclear receptor transcription factor function and does not impair STAT function (FIG. 7a). Furthermore, a mutation within this motif markedly impairs the function of this region of p/CIP (data not shown). Thus, specific signal transduction pathways can be selectively blocked by distinct helical interaction motifs.

Other motifs, not required for nuclear receptor activation, also were examined to determine if, similarly, they are critical for coactivator function for other classes of CBP-dependent transcription factors, thus providing a means to selective block distinct signal transduction pathways. This study was initiated based on the demonstration that a critical STAT interaction domain is found within the first 100 amino acids of CBP by coimmunoprecipitation (Horvai et al., supra, 1997). To determine whether a sequence of the CBP N-terminal 100 amino acids, distinct from the nuclear receptor motif, can both mediate interactions with STAT-1 and be required for STAT function, the effects of peptides corresponding to N-terminal regions of CBP on STAT-1 or retinoic acid receptor function was evaluated. Remarkably, a synthetic peptide against the N-terminal 22 amino acids of CBP (CBP N'P1; FIG. 7b) markedly inhibited interferon γ-dependent gene activation, but was without effect on retinoic acid receptor function. The identical peptide, from which the N-terminal seven amino acids (MAENLLY) were deleted, abolished this effect (CBP N'-P2; FIG. 7b), indicating that this sequence encompassed a motif required for STAT interaction and function. These results further support the functional significance of the STAT-1 interaction motif previously identified in the CBP N-terminus (Horvai et al., supra, 1997).

In parallel, the ability of the CBP N-terminal peptide to selectively-block the inhibitory effects of STAT-1 or retinoic acid receptor-dependent transcription was examined by evaluating its effects on simultaneous stimulation by interferon γ and retinoic acid. The simultaneous addition of retinoic acid and interferon γ led to reciprocal inhibition of retinoic acid- and interferon-dependent reporter gene expression (FIG. 7c). However, the addition of the CBP N-terminal 22 amino acid peptide (CBP N'-P1) relieved inhibition of RAR-dependent transcription by interferon γ, consistent with the hypothesis that this inhibitory effect represents, at least in part, competition for CBP coactivator complexes, analogous to that proposed for AP-1 and nuclear receptors (Kamei et al., supra, 1997). Together, these results are consistent with the hypothesis that different motifs are used in assembling CBP-dependent complexes by different classes of transcription factors, and that peptides based on these motifs can selectively block specific signal transduction pathways.

The results disclosed herein indicate that p/CIP, which is associated with CBP/p300 in cell, is involved in regulating transcription by nuclear receptors and by other CBP-dependent factors, including STAT and AP-1. Furthermore, both the CBP/p/CIP complex and NCoA-1 are required to permit full ligand-activated gene transcription in the cells examined, while NCoA-1/SRC-1 is not required for other CBP-dependent transcription. Because CBP is capable of associating with a large number of additional factors, including myb, YY1, SREBP, myoD and the HLH1 factors, it is likely that p/CIP and CBP are components of a larger complex inportant for integration of many signal transduction pathways.

Studies have shown that the N-terminus of CBP alone is sufficient to potentiate CREB function using transient cotransfection assays (Bisotto et al., J. Biol. Chem. 271: 17746–17750 (1996); Swope et al., J. Biol. Chem. 271: 28138–28145 (1996)). In contrast, a recent study has shown that the C-terminus also was required in in vitro transcription assays (Nakajima et al., Genes and Devel. 11:738–747 (1997)). While not wishing to be bound by the following, the results disclosed herein indicate that conformational alterations in CBP holoprotein, which may be contributed by p/CIP, can modulate interactions with transcription factors and associated regulatory proteins, including protein kinases and those that have been shown to possess histone acetylase functions. Furthermore, p/CAF is capable of interacting with NCoA-1 as well as CBP41, although its role in mediating the transcriptional activation by nuclear receptors is unclear.

The nuclear receptor and CBP interaction domains within NCoA-1, NCoA-2, and p/CIP contain putative helical domains, referred to as LCD's, that are required and, in at least in some cases, sufficient, for receptor-specific interactions. Thus, the third helical domain in the nuclear receptor interaction domain of NCoA-1 is differentially utilized, being important for retinoic acid function, but not for estrogen receptor-dependent gene activation events. Similar LCD's are present in CBP and in other factors, including TIF-1 and RIP 140, as well as in the N-terminal interaction domain of p/CAF. Thus, many factors can have the ability to associate with the complexes formed on receptor homodimers or heterodimers bound to their cognate DNA site and contribute to the specificity of nuclear receptor pathways. Such an assembly of specific complexes of proteins based on these interaction motifs can provide a basis for receptor-specific and regulated aspects of nuclear receptor function.

As disclosed herein, helical interaction domains in CBP/p/CIP/NCoA proteins and other nuclear receptor interacting factors permitted the use of such domains to selectively block gene activation events in response to specific signal transduction pathways. Thus, peptides corresponding to CBP interaction domains selectively block nuclear receptor or STAT-1 function. The actions of specific inhibitory peptides indicates that partitioning of CBP accounts, at least in part, for trans-repression of nuclear receptor, STAT and AP-1 pathways.

SEQUENCE LISTING

```
<160> NUMBER OF SEQ ID NOS: 14

<210> SEQ ID NO 1
<211> LENGTH: 4860
<212> TYPE: DNA
<213> ORGANISM: Mus musculus
<220> FEATURE:
<221> NAME/KEY: misc_feature
<222> LOCATION: (3121)..(3121)
<223> OTHER INFORMATION: "n" is any nucleotide
<220> FEATURE:
<221> NAME/KEY: CDS
<222> LOCATION: (110)..(4318)
<223> OTHER INFORMATION:
<300> PUBLICATION INFORMATION:
<301> AUTHORS: Joseph Torchia, David W. Rose, Juan Inostroza, Yasutomi
```

```
            Kamei, Stefan Westin
<302> TITLE: The transcriptional co-activator p/CIP binds CBP and
      mediates nuclear receptor function
<303> JOURNAL: Nature
<304> VOLUME: 387
<305> ISSUE: 6634
<306> PAGES: 677-684
<307> DATE: 1997-06-12
<308> DATABASE ACCESSION NUMBER: AF000581
<309> DATABASE ENTRY DATE: 1997-06-12

<400> SEQUENCE: 1
ggcggcgaac ggatcaaaag aatttgctga acagtggact ccgagatcgg taaaacgaac         60
tcttccctgc ccttcctgaa cagctgtcag ttgctgatct gtgatcagg atg agt gga        118
                                                       Met Ser Gly
                                                         1 cta ggc gaa agc tct ttg gat ccg ctg gcc gct gag tct cgg aaa cgc         166
Leu Gly Glu Ser Ser Leu Asp Pro Leu Ala Ala Glu Ser Arg Lys Arg
      5              10                  15 aaa ctg ccc tgt gat gcc cca gga cag ggg ctt gtc tac agt ggt gag         214
Lys Leu Pro Cys Asp Ala Pro Gly Gln Gly Leu Val Tyr Ser Gly Glu
 20              25                  30                  35 aag tgg cga cgg gag cag gag agc aag tac ata gag gag ctg gca gag         262
Lys Trp Arg Arg Glu Gln Glu Ser Lys Tyr Ile Glu Glu Leu Ala Glu
                 40                  45                  50 ctc atc tct gca aat ctc agc gac atc gac aac ttc aat gtc aag cca         310
Leu Ile Ser Ala Asn Leu Ser Asp Ile Asp Asn Phe Asn Val Lys Pro
             55                  60                  65 gat aaa tgt gcc atc cta aag gag aca gtg aga cag ata cgg caa ata         358
Asp Lys Cys Ala Ile Leu Lys Glu Thr Val Arg Gln Ile Arg Gln Ile
         70                  75                  80 aaa gaa caa gga aaa act att tcc agt gat gat gat gtt caa aaa gct         406
Lys Glu Gln Gly Lys Thr Ile Ser Ser Asp Asp Asp Val Gln Lys Ala
 85                  90                  95 gat gtg tct tct aca ggg cag gga gtc att gat aaa gac tct tta gga         454
Asp Val Ser Ser Thr Gly Gln Gly Val Ile Asp Lys Asp Ser Leu Gly
100                 105                 110                 115 ccg ctt tta cta cag gca ctg gat ggt ttc ctg ttt gtg gtg aat cga         502
Pro Leu Leu Leu Gln Ala Leu Asp Gly Phe Leu Phe Val Val Asn Arg
                 120                 125                 130 gat gga aac att gta ttc gtg tca gaa aat gtc aca cag tat ctg cag         550
Asp Gly Asn Ile Val Phe Val Ser Glu Asn Val Thr Gln Tyr Leu Gln
             135                 140                 145 tac aag cag gag gac ctg gtt aac aca agt gtc tac agc atc tta cat         598
Tyr Lys Gln Glu Asp Leu Val Asn Thr Ser Val Tyr Ser Ile Leu His
         150                 155                 160 gag cca aga cgg aag gat ttc tta aac act tac caa aat cca cag tta         646
Glu Pro Arg Arg Lys Asp Phe Leu Asn Thr Tyr Gln Asn Pro Gln Leu
    165                 170                 175 atg gag ttt ctt gga cta atg aga acc aga gac aaa aaa gcc cca tac         694
Met Glu Phe Leu Gly Leu Met Arg Thr Arg Asp Lys Lys Ala Pro Tyr
180                 185                 190                 195 att tta att gtc cgt atg ttg atg aaa aca cac gac att ttg gaa gac         742
Ile Leu Ile Val Arg Met Leu Met Lys Thr His Asp Ile Leu Glu Asp
                 200                 205                 210 gtg aat gcc agt ccc gaa acg cgc cag aga tat gaa aca atg cag tgc         790
Val Asn Ala Ser Pro Glu Thr Arg Gln Arg Tyr Glu Thr Met Gln Cys
             215                 220                 225 ttt gcc ctg tct cag cct cgc gct atg ctg gaa gaa gga gaa gac ttg         838
Phe Ala Leu Ser Gln Pro Arg Ala Met Leu Glu Glu Gly Glu Asp Leu
         230                 235                 240
```

| | |
|---|---|
| cag tgc tgt atg atc tgc gtg gct cgc cgc gtg act gcg cca ttc cca<br>Gln Cys Cys Met Ile Cys Val Ala Arg Arg Val Thr Ala Pro Phe Pro<br>245                          250                         255 | 886 |
| tcc agt ccc gag agc ttt att acc aga cat gac ctt tcc gga aag gtt<br>Ser Ser Pro Glu Ser Phe Ile Thr Arg His Asp Leu Ser Gly Lys Val<br>260                         265                        270                        275 | 934 |
| gtc aat ata gat aca aac tca ctt aga tct tcc atg agg cct ggc ttt<br>Val Asn Ile Asp Thr Asn Ser Leu Arg Ser Ser Met Arg Pro Gly Phe<br>                         280                        285                        290 | 982 |
| gaa gac ata atc cga aga tgt atc cag agg ttc ttc agt ctg aat gat<br>Glu Asp Ile Ile Arg Arg Cys Ile Gln Arg Phe Phe Ser Leu Asn Asp<br>                295                        300                        305 | 1030 |
| ggg cag tca tgg tcc cag aag cgt cac tat caa gaa gct tat gtt cat<br>Gly Gln Ser Trp Ser Gln Lys Arg His Tyr Gln Glu Ala Tyr Val His<br>          310                        315                        320 | 1078 |
| ggc cac gca gag acc ccc gtg tat cgt ttc tcc ttg gct gat gga act<br>Gly His Ala Glu Thr Pro Val Tyr Arg Phe Ser Leu Ala Asp Gly Thr<br>325                         330                        335 | 1126 |
| att gtg agt gcg cag aca aaa agc aaa ctc ttc cgc aat cct gta acg<br>Ile Val Ser Ala Gln Thr Lys Ser Lys Leu Phe Arg Asn Pro Val Thr<br>340                         345                        350                        355 | 1174 |
| aat gat cgt cac ggc ttc atc tcg acc cac ttt ctt cag aga gaa cag<br>Asn Asp Arg His Gly Phe Ile Ser Thr His Phe Leu Gln Arg Glu Gln<br>                         360                        365                        370 | 1222 |
| aat gga tac aga cca aac cca atc ccg cag gac aaa ggc atc cga cct<br>Asn Gly Tyr Arg Pro Asn Pro Ile Pro Gln Asp Lys Gly Ile Arg Pro<br>                375                        380                        385 | 1270 |
| cct gca gca ggg tgt ggc gtg agc atg tct cca aat cag aat gta cag<br>Pro Ala Ala Gly Cys Gly Val Ser Met Ser Pro Asn Gln Asn Val Gln<br>          390                        395                        400 | 1318 |
| atg atg ggc agc cgg acc tat ggc gtg cca gac ccc agc aac aca ggg<br>Met Met Gly Ser Arg Thr Tyr Gly Val Pro Asp Pro Ser Asn Thr Gly<br>405                         410                        415 | 1366 |
| cag atg ggt gga gct agg tac ggg gct tct agt agc gta gcc tca ctg<br>Gln Met Gly Gly Ala Arg Tyr Gly Ala Ser Ser Ser Val Ala Ser Leu<br>420                         425                        430                        435 | 1414 |
| acg cca gga caa agc cta cag tcg cca tct tcc tat cag aac agc agc<br>Thr Pro Gly Gln Ser Leu Gln Ser Pro Ser Ser Tyr Gln Asn Ser Ser<br>                         440                        445                        450 | 1462 |
| tat ggg ctc agc atg agc agt ccc ccc cac ggc agt cct ggt ctt ggc<br>Tyr Gly Leu Ser Met Ser Ser Pro His Gly Ser Pro Gly Leu Gly<br>                455                        460                        465 | 1510 |
| ccc aac cag cag aac atc atg att tcc cct cgg aat cgt ggc agc cca<br>Pro Asn Gln Gln Asn Ile Met Ile Ser Pro Arg Asn Arg Gly Ser Pro<br>          470                        475                        480 | 1558 |
| aag atg gcc tcc cac cag ttc tct cct gct gca ggt gca cac tca ccc<br>Lys Met Ala Ser His Gln Phe Ser Pro Ala Ala Gly Ala His Ser Pro<br>485                         490                        495 | 1606 |
| atg gga cct tct ggc aac aca ggg agc cac agc ttt tct agc agc tcc<br>Met Gly Pro Ser Gly Asn Thr Gly Ser His Ser Phe Ser Ser Ser Ser<br>500                         505                        510                        515 | 1654 |
| ctc agt gcc ttg caa gcc atc agt gaa ggc gtg ggg acc tct ctt tta<br>Leu Ser Ala Leu Gln Ala Ile Ser Glu Gly Val Gly Thr Ser Leu Leu<br>                         520                        525                        530 | 1702 |
| tct act ctg tcc tca cca ggc ccc aaa ctg gat aat tct ccc aat atg<br>Ser Thr Leu Ser Ser Pro Gly Pro Lys Leu Asp Asn Ser Pro Asn Met<br>                         535                        540                        545 | 1750 |
| aat ata agc cag cca agt aaa gtg agt ggt cag gac tct aag agc ccc<br>Asn Ile Ser Gln Pro Ser Lys Val Ser Gly Gln Asp Ser Lys Ser Pro<br>550                         555                        560 | 1798 |

```
cta ggc tta tac tgt gaa cag aat cca gtg gag agt tca gtg tgt cag    1846
Leu Gly Leu Tyr Cys Glu Gln Asn Pro Val Glu Ser Ser Val Cys Gln
565                 570                 575 tca aac agc aga gat ccc caa gtg aaa aaa gaa agc aag gag agc agt    1894
Ser Asn Ser Arg Asp Pro Gln Val Lys Lys Glu Ser Lys Glu Ser Ser
580                 585                 590                 595 ggg gag gtg tca gag acg ccc agg gga cct ctg gaa agc aaa ggc cac    1942
Gly Glu Val Ser Glu Thr Pro Arg Gly Pro Leu Glu Ser Lys Gly His
            600                 605                 610 aag aaa ctg ctg cag tta ctc acg tgc tcc tcc gac gac cga ggc cat    1990
Lys Lys Leu Leu Gln Leu Leu Thr Cys Ser Ser Asp Asp Arg Gly His
        615                 620                 625 tcc tcc ttg acc aac tct ccc ctg gat cca aac tgc aaa gac tct tcc    2038
Ser Ser Leu Thr Asn Ser Pro Leu Asp Pro Asn Cys Lys Asp Ser Ser
    630                 635                 640 gtt agt gtc acc agc ccc tct gga gtg tcc tcc tca aca tca ggg aca    2086
Val Ser Val Thr Ser Pro Ser Gly Val Ser Ser Ser Thr Ser Gly Thr
645                 650                 655 gtg tct tcc acc tcc aat gtg cat ggg tct ctg ttg caa gag aaa cac    2134
Val Ser Ser Thr Ser Asn Val His Gly Ser Leu Leu Gln Glu Lys His
660                 665                 670                 675 cgg att ttg cac aag ttg ctg cag aat ggc aac tcc cca gcg gag gtc    2182
Arg Ile Leu His Lys Leu Leu Gln Asn Gly Asn Ser Pro Ala Glu Val
            680                 685                 690 gcc aag atc act gca gag gcc act ggg aag gac acg agc agc act gct    2230
Ala Lys Ile Thr Ala Glu Ala Thr Gly Lys Asp Thr Ser Ser Thr Ala
        695                 700                 705 tcc tgt gga gag ggg aca acc agg cag gag cag ctg agt cct aag aag    2278
Ser Cys Gly Glu Gly Thr Thr Arg Gln Glu Gln Leu Ser Pro Lys Lys
    710                 715                 720 aag gag aat aat gct ctg ctt aga tac ctg ctg gac agg gat gac ccc    2326
Lys Glu Asn Asn Ala Leu Leu Arg Tyr Leu Leu Asp Arg Asp Asp Pro
725                 730                 735 agt gat gtg ctt gcc aaa gag ctg cag ccc cag gcc gac agt ggg gac    2374
Ser Asp Val Leu Ala Lys Glu Leu Gln Pro Gln Ala Asp Ser Gly Asp
740                 745                 750                 755 agt aaa ctg agt cag tgc agc tgc tcc acc aat ccc agc tct ggc caa    2422
Ser Lys Leu Ser Gln Cys Ser Cys Ser Thr Asn Pro Ser Ser Gly Gln
            760                 765                 770 gag aaa gac ccc aaa att aag acc gag acg aac gac gag gta tcg gga    2470
Glu Lys Asp Pro Lys Ile Lys Thr Glu Thr Asn Asp Glu Val Ser Gly
        775                 780                 785 gac ctg gat aat cta gat gcc att ctt gga gat ttg acc agt tct gac    2518
Asp Leu Asp Asn Leu Asp Ala Ile Leu Gly Asp Leu Thr Ser Ser Asp
    790                 795                 800 ttc tac aac aat cct aca aat ggc ggt cac cca ggg gcc aaa cag cag    2566
Phe Tyr Asn Asn Pro Thr Asn Gly Gly His Pro Gly Ala Lys Gln Gln
805                 810                 815 atg ttt gca gga ccg agt tct ctg ggt ttg cga agt cca cag cct gtg    2614
Met Phe Ala Gly Pro Ser Ser Leu Gly Leu Arg Ser Pro Gln Pro Val
820                 825                 830                 835 cag tct gtt cgt cct cca tat aac cga gcg gtg tct ctg gat agc cct    2662
Gln Ser Val Arg Pro Pro Tyr Asn Arg Ala Val Ser Leu Asp Ser Pro
            840                 845                 850 gtg tct gtt ggc tca ggt ccg cca gtg aag aat gtc agt gct ttc cct    2710
Val Ser Val Gly Ser Gly Pro Pro Val Lys Asn Val Ser Ala Phe Pro
        855                 860                 865 ggg tta cca aaa cag ccc ata ctg gct ggg aat cca aga atg atg gat    2758
Gly Leu Pro Lys Gln Pro Ile Leu Ala Gly Asn Pro Arg Met Met Asp
```

-continued

| | |
|---|---|
| agt cag gag aat tac ggt gcc aac atg ggc cca aac aga aat gtt cct<br>Ser Gln Glu Asn Tyr Gly Ala Asn Met Gly Pro Asn Arg Asn Val Pro<br>885                    890                   895 | 2806 |
| gtg aat ccg act tcc tcc ccc gga gac tgg ggc tta gct aac tca agg<br>Val Asn Pro Thr Ser Ser Pro Gly Asp Trp Gly Leu Ala Asn Ser Arg<br>900                    905                  910                915 | 2854 |
| gcc agc aga atg gag cct ctg gca tca agt ccc ctg gga aga act gga<br>Ala Ser Arg Met Glu Pro Leu Ala Ser Ser Pro Leu Gly Arg Thr Gly<br>920                    925                  930 | 2902 |
| gcc gat tac agt gcc act tta ccc aga cct gcc atg ggg ggc tct gtg<br>Ala Asp Tyr Ser Ala Thr Leu Pro Arg Pro Ala Met Gly Gly Ser Val<br>935                    940                  945 | 2950 |
| cct acc ttg cca ctt cgt tct aat cga ctg cca ggt gca aga cca tcg<br>Pro Thr Leu Pro Leu Arg Ser Asn Arg Leu Pro Gly Ala Arg Pro Ser<br>950                    955                  960 | 2998 |
| ttg cag caa cag cag cag caa cag cag caa cag caa caa caa cag cag<br>Leu Gln Gln Gln Gln Gln Gln Gln Gln Gln Gln Gln Gln Gln Gln Gln<br>965                    970                  975 | 3046 |
| caa cag cag cag caa cag cag cag atg ctt caa atg aga act ggt gag<br>Gln Gln Gln Gln Gln Gln Gln Gln Met Leu Gln Met Arg Thr Gly Glu<br>980                    985                  990                995 | 3094 |
| att ccc atg gga atg  gga gtc aat ccn tat  agc cca gca gtg cag<br>Ile Pro Met Gly Met  Gly Val Asn Pro Tyr  Ser Pro Ala Val Gln<br>               1000                       1005                 1010 | 3139 |
| tct aac caa cca ggt  tcc tgg cca gag ggc  atg ctc tct atg gaa<br>Ser Asn Gln Pro Gly  Ser Trp Pro Glu Gly  Met Leu Ser Met Glu<br>               1015                       1020                 1025 | 3184 |
| caa ggt cct cac ggg  tct caa aat agg cct  ctt ctt aga aac tct<br>Gln Gly Pro His Gly  Ser Gln Asn Arg Pro  Leu Leu Arg Asn Ser<br>               1030                       1035                 1040 | 3229 |
| ctg gat gat ctg ctt  ggg cca cct tct aac  gca gag ggc cag agt<br>Leu Asp Asp Leu Leu  Gly Pro Pro Ser Asn  Ala Glu Gly Gln Ser<br>               1045                       1050                 1055 | 3274 |
| gac gag aga gct ctg  ctg gac cag ctg cac  aca ttc ctg agc aac<br>Asp Glu Arg Ala Leu  Leu Asp Gln Leu His  Thr Phe Leu Ser Asn<br>               1060                       1065                 1070 | 3319 |
| aca gat gcc aca ggt  ctg gag gag atc gac  agg gcc ttg gga att<br>Thr Asp Ala Thr Gly  Leu Glu Glu Ile Asp  Arg Ala Leu Gly Ile<br>               1075                       1080                 1085 | 3364 |
| cct gag ctc gtg aat  cag gga caa gct ttg  gag tcc aaa cag gat<br>Pro Glu Leu Val Asn  Gln Gly Gln Ala Leu  Glu Ser Lys Gln Asp<br>               1090                       1095                 1100 | 3409 |
| gtt ttc caa ggc caa  gaa gca gca gta atg  atg gat cag aag gct<br>Val Phe Gln Gly Gln  Glu Ala Ala Val Met  Met Asp Gln Lys Ala<br>               1105                       1110                 1115 | 3454 |
| gca cta tat gga cag  aca tac cca gct cag  ggt cct ccc ctt caa<br>Ala Leu Tyr Gly Gln  Thr Tyr Pro Ala Gln  Gly Pro Pro Leu Gln<br>               1120                       1125                 1130 | 3499 |
| gga ggc ttt aac ctt  cag gga cag tca cca  tcg ttt aac tct atg<br>Gly Gly Phe Asn Leu  Gln Gly Gln Ser Pro  Ser Phe Asn Ser Met<br>               1135                       1140                 1145 | 3544 |
| atg ggt cag att agc  cag caa ggc agc ttt  cct ctg caa ggc atg<br>Met Gly Gln Ile Ser  Gln Gln Gly Ser Phe  Pro Leu Gln Gly Met<br>               1150                       1155                 1160 | 3589 |
| cat cct aga gcc ggc  ctc gtg aga cca agg  acc aac acc ccg aag<br>His Pro Arg Ala Gly  Leu Val Arg Pro Arg  Thr Asn Thr Pro Lys<br>               1165                       1170                 1175 | 3634 |
| cag ctg aga atg cag   ctt cag cag agg cta   cag ggc cag cag ttt | 3679 |

-continued

| | | | | | | | | | | | | |
|---|---|---|---|---|---|---|---|---|---|---|---|---|
|Gln|Leu|Arg|Met|Gln|Leu|Gln|Gln|Arg|Leu|Gln|Gly|Gln|Gln|Phe|
| | | |1180| | | |1185| | | |1190| | | |

```
tta aat cag agc cgg  cag gca ctt gaa atg  aaa atg gag aac cct       3724
Leu Asn Gln Ser Arg  Gln Ala Leu Glu Met  Lys Met Glu Asn Pro
            1195                 1200                 1205 gct ggc act gct gtg  atg agg ccc atg atg  ccc cag gct ttc ttt       3769
Ala Gly Thr Ala Val  Met Arg Pro Met Met  Pro Gln Ala Phe Phe
            1210                 1215                 1220 aat gcc caa atg gct  gcc cag cag aaa cga  gag ctg atg agc cat       3814
Asn Ala Gln Met Ala  Ala Gln Gln Lys Arg  Glu Leu Met Ser His
            1225                 1230                 1235 cac ctg cag cag cag  agg atg gcg atg atg  atg tca caa cca cag       3859
His Leu Gln Gln Gln  Arg Met Ala Met Met  Met Ser Gln Pro Gln
            1240                 1245                 1250 cct cag gcc ttc agc  cca cct ccc aac gtc  acc gcc tcc ccc agc       3904
Pro Gln Ala Phe Ser  Pro Pro Pro Asn Val  Thr Ala Ser Pro Ser
            1255                 1260                 1265 atg gac ggg gtt ttg  gca ggt tca gca atg  ccg caa gcc cct cca       3949
Met Asp Gly Val Leu  Ala Gly Ser Ala Met  Pro Gln Ala Pro Pro
            1270                 1275                 1280 caa cag ttt cca tat  cca gca aat tac gga  acg gga caa cca cca       3994
Gln Gln Phe Pro Tyr  Pro Ala Asn Tyr Gly  Thr Gly Gln Pro Pro
            1285                 1290                 1295 gta gcc agc ctt tgg  tcg agg ctc gag tcc  tcc cag tgc aat gat       4039
Val Ala Ser Leu Trp  Ser Arg Leu Glu Ser  Ser Gln Cys Asn Asp
            1300                 1305                 1310 gtc atc aag aat ggg  gcc ttc cca gaa tgc  cat ggt gca gca tcc       4084
Val Ile Lys Asn Gly  Ala Phe Pro Glu Cys  His Gly Ala Ala Ser
            1315                 1320                 1325 tca gcc cac acc cat  gta tca gcc ttc aga  tat gaa ggg gtg gcc       4129
Ser Ala His Thr His  Val Ser Ala Phe Arg  Tyr Glu Gly Val Ala
            1330                 1335                 1340 gtc agg gaa cct ggc  cag gaa tgg ctc ctt  ccc cca gca gca gtt       4174
Val Arg Glu Pro Gly  Gln Glu Trp Leu Leu  Pro Pro Ala Ala Val
            1345                 1350                 1355 tgc tcc cca ggg gaa  ccc tgc agc cta caa  cat ggt gca tat gaa       4219
Cys Ser Pro Gly Glu  Pro Cys Ser Leu Gln  His Gly Ala Tyr Glu
            1360                 1365                 1370 cag cag cgg tgg gca  ctt ggg aca gat ggc  cat gac ccc cat gcc       4264
Gln Gln Arg Trp Ala  Leu Gly Thr Asp Gly  His Asp Pro His Ala
            1375                 1380                 1385 cat gtc tgg cat gcc  cat ggg ccc cga tca  gaa ata ctg ctg aca       4309
His Val Trp His Ala  His Gly Pro Arg Ser  Glu Ile Leu Leu Thr
            1390                 1395                 1400 tct ccc tag tgggactgac tgtacagatg acactgcaca ggatcatcag             4358
Ser Pro gacgtggcgg cgagtcattg tctaagcatc agcttggaa gcaaggccag cgtgaccagc    4418 agcgggtct gtgctgtcat ttgagcagag ctgggtctcg ctgaagcgca ctgtctacct    4478
gatgccctgc ctctgtgtgg caaggtgttc tgcctcatga ggatgtgatt ctggagatgg   4538
ggtgttcgta agcaccgctc tcttacgtca ctcccttctg cctcgccagc caaagtcttc   4598
acgtagatct agatggctag ggtttctgtc ttgcagcact ggacgagggg gcacactctg   4658
ccttctcgcg tgtcgtcagc aagttagttc gtgtcgctct cctgtccagt gcaatcagtg   4718
tttctgcgct cttgtccttt acaggtgtaa tccccaagtc tgtcgtccta gtctctcctg   4778
gtgaagtccc cgtacctgta atctcaacaa ttctcattga gtttaaatg gcttttgaaa    4838 aaagggaaaa atgaaaatgg ca                                             4860
```

<210> SEQ ID NO 2
<211> LENGTH: 1402
<212> TYPE: PRT
<213> ORGANISM: Mus musculus
<220> FEATURE:
<221> NAME/KEY: misc_feature
<222> LOCATION: (3121)..(3121)
<223> OTHER INFORMATION: "n" is any nucleotide

<400> SEQUENCE: 2

```
Met Ser Gly Leu Gly Glu Ser Ser Leu Asp Pro Leu Ala Ala Glu Ser
 1               5                  10                  15

Arg Lys Arg Lys Leu Pro Cys Asp Ala Pro Gly Gln Gly Leu Val Tyr
            20                  25                  30

Ser Gly Glu Lys Trp Arg Arg Gln Glu Ser Lys Tyr Ile Glu Glu
        35                  40                  45

Leu Ala Glu Leu Ile Ser Ala Asn Leu Ser Asp Ile Asp Asn Phe Asn
    50                  55                  60

Val Lys Pro Asp Lys Cys Ala Ile Leu Lys Glu Thr Val Arg Gln Ile
65                  70                  75                  80

Arg Gln Ile Lys Glu Gln Gly Lys Thr Ile Ser Ser Asp Asp Val
                85                  90                  95

Gln Lys Ala Asp Val Ser Ser Thr Gly Gln Gly Val Ile Asp Lys Asp
            100                 105                 110

Ser Leu Gly Pro Leu Leu Leu Gln Ala Leu Asp Gly Phe Leu Phe Val
        115                 120                 125

Val Asn Arg Asp Gly Asn Ile Val Phe Val Ser Glu Asn Val Thr Gln
    130                 135                 140

Tyr Leu Gln Tyr Lys Gln Glu Asp Leu Val Asn Thr Ser Val Tyr Ser
145                 150                 155                 160

Ile Leu His Glu Pro Arg Arg Lys Asp Phe Leu Asn Thr Tyr Gln Asn
                165                 170                 175

Pro Gln Leu Met Glu Phe Leu Gly Leu Met Arg Thr Arg Asp Lys Lys
            180                 185                 190

Ala Pro Tyr Ile Leu Ile Val Arg Met Leu Met Lys Thr His Asp Ile
        195                 200                 205

Leu Glu Asp Val Asn Ala Ser Pro Glu Thr Arg Gln Arg Tyr Glu Thr
    210                 215                 220

Met Gln Cys Phe Ala Leu Ser Gln Pro Arg Ala Met Leu Glu Glu Gly
225                 230                 235                 240

Glu Asp Leu Gln Cys Cys Met Ile Cys Val Ala Arg Arg Val Thr Ala
                245                 250                 255

Pro Phe Pro Ser Ser Pro Glu Ser Phe Ile Thr Arg His Asp Leu Ser
            260                 265                 270

Gly Lys Val Val Asn Ile Asp Thr Asn Ser Leu Arg Ser Ser Met Arg
        275                 280                 285

Pro Gly Phe Glu Asp Ile Ile Arg Arg Cys Ile Gln Arg Phe Phe Ser
    290                 295                 300

Leu Asn Asp Gly Gln Ser Trp Ser Gln Lys Arg His Tyr Gln Glu Ala
305                 310                 315                 320

Tyr Val His Gly His Ala Glu Thr Pro Val Tyr Arg Phe Ser Leu Ala
                325                 330                 335

Asp Gly Thr Ile Val Ser Ala Gln Thr Lys Ser Lys Leu Phe Arg Asn
            340                 345                 350
```

-continued

```
Pro Val Thr Asn Asp Arg His Gly Phe Ile Ser Thr His Phe Leu Gln
        355                 360                 365
Arg Glu Gln Asn Gly Tyr Arg Pro Asn Pro Ile Pro Gln Asp Lys Gly
        370                 375                 380
Ile Arg Pro Pro Ala Ala Gly Cys Gly Val Ser Met Ser Pro Asn Gln
385                 390                 395                 400
Asn Val Gln Met Met Gly Ser Arg Thr Tyr Gly Val Pro Asp Pro Ser
            405                 410                 415
Asn Thr Gly Gln Met Gly Gly Ala Arg Tyr Gly Ala Ser Ser Ser Val
            420                 425                 430
Ala Ser Leu Thr Pro Gly Gln Ser Leu Gln Ser Pro Ser Ser Tyr Gln
        435                 440                 445
Asn Ser Ser Tyr Gly Leu Ser Met Ser Ser Pro His Gly Ser Pro
        450                 455                 460
Gly Leu Gly Pro Asn Gln Gln Asn Ile Met Ile Ser Pro Arg Asn Arg
465                 470                 475                 480
Gly Ser Pro Lys Met Ala Ser His Gln Phe Ser Pro Ala Ala Gly Ala
            485                 490                 495
His Ser Pro Met Gly Pro Ser Gly Asn Thr Gly Ser His Ser Phe Ser
            500                 505                 510
Ser Ser Ser Leu Ser Ala Leu Gln Ala Ile Ser Glu Gly Val Gly Thr
        515                 520                 525
Ser Leu Leu Ser Thr Leu Ser Ser Pro Gly Pro Lys Leu Asp Asn Ser
        530                 535                 540
Pro Asn Met Asn Ile Ser Gln Pro Ser Lys Val Ser Gly Gln Asp Ser
545                 550                 555                 560
Lys Ser Pro Leu Gly Leu Tyr Cys Glu Gln Asn Pro Val Glu Ser Ser
            565                 570                 575
Val Cys Gln Ser Asn Ser Arg Asp Pro Gln Val Lys Lys Glu Ser Lys
            580                 585                 590
Glu Ser Ser Gly Glu Val Ser Glu Thr Pro Arg Gly Pro Leu Glu Ser
        595                 600                 605
Lys Gly His Lys Lys Leu Leu Gln Leu Leu Thr Cys Ser Ser Asp Asp
        610                 615                 620
Arg Gly His Ser Ser Leu Thr Asn Ser Pro Leu Asp Pro Asn Cys Lys
625                 630                 635                 640
Asp Ser Ser Val Ser Val Thr Ser Pro Ser Gly Val Ser Ser Ser Thr
            645                 650                 655
Ser Gly Thr Val Ser Ser Thr Ser Asn Val His Gly Ser Leu Leu Gln
            660                 665                 670
Glu Lys His Arg Ile Leu His Lys Leu Leu Gln Asn Gly Asn Ser Pro
        675                 680                 685
Ala Glu Val Ala Lys Ile Thr Ala Glu Ala Thr Gly Lys Asp Thr Ser
        690                 695                 700
Ser Thr Ala Ser Cys Gly Glu Gly Thr Thr Arg Gln Glu Gln Leu Ser
705                 710                 715                 720
Pro Lys Lys Lys Glu Asn Asn Ala Leu Leu Arg Tyr Leu Leu Asp Arg
            725                 730                 735
Asp Asp Pro Ser Asp Val Leu Ala Lys Glu Leu Gln Pro Gln Ala Asp
            740                 745                 750
Ser Gly Asp Ser Lys Leu Ser Gln Cys Ser Cys Ser Thr Asn Pro Ser
        755                 760                 765
Ser Gly Gln Glu Lys Asp Pro Lys Ile Lys Thr Glu Thr Asn Asp Glu
```

-continued

```
            770                 775                 780
Val Ser Gly Asp Leu Asp Asn Leu Asp Ala Ile Leu Gly Asp Leu Thr
785                 790                 795                 800

Ser Ser Asp Phe Tyr Asn Asn Pro Thr Asn Gly Gly His Pro Gly Ala
                805                 810                 815

Lys Gln Gln Met Phe Ala Gly Pro Ser Ser Leu Gly Leu Arg Ser Pro
                820                 825                 830

Gln Pro Val Gln Ser Val Arg Pro Tyr Asn Arg Ala Val Ser Leu
                835                 840                 845

Asp Ser Pro Val Ser Val Gly Ser Gly Pro Val Lys Asn Val Ser
850                 855                 860

Ala Phe Pro Gly Leu Pro Lys Gln Pro Ile Leu Ala Gly Asn Pro Arg
865                 870                 875                 880

Met Met Asp Ser Gln Glu Asn Tyr Gly Ala Asn Met Gly Pro Asn Arg
                885                 890                 895

Asn Val Pro Val Asn Pro Thr Ser Ser Pro Gly Asp Trp Gly Leu Ala
                900                 905                 910

Asn Ser Arg Ala Ser Arg Met Glu Pro Leu Ala Ser Ser Pro Leu Gly
                915                 920                 925

Arg Thr Gly Ala Asp Tyr Ser Ala Thr Leu Pro Arg Pro Ala Met Gly
                930                 935                 940

Gly Ser Val Pro Thr Leu Pro Leu Arg Ser Asn Arg Leu Pro Gly Ala
945                 950                 955                 960

Arg Pro Ser Leu Gln Gln Gln Gln Gln Gln Gln Gln Gln Gln Gln
                965                 970                 975

Gln Gln Gln Gln Gln Gln Gln Gln Gln Gln Met Leu Gln Met Arg
                980                 985                 990

Thr Gly Glu Ile Pro Met Gly Met  Gly Val Asn Pro Tyr  Ser Pro Ala
                995                 1000                1005

Val Gln  Ser Asn Gln Pro Gly  Ser Trp Pro Glu Gly  Met Leu Ser
    1010                1015                1020

Met Glu Gln Gly Pro His Gly  Ser Gln Asn Arg Pro  Leu Leu Arg
    1025                1030                1035

Asn Ser  Leu Asp Asp Leu Leu  Gly Pro Pro Ser Asn  Ala Glu Gly
    1040                1045                1050

Gln Ser  Asp Glu Arg Ala Leu  Leu Asp Gln Leu His  Thr Phe Leu
    1055                1060                1065

Ser Asn  Thr Asp Ala Thr Gly  Leu Glu Glu Ile Asp  Arg Ala Leu
    1070                1075                1080

Gly Ile  Pro Glu Leu Val Asn  Gln Gly Gln Ala Leu  Glu Ser Lys
    1085                1090                1095

Gln Asp  Val Phe Gln Gly Gln  Glu Ala Ala Val Met  Met Asp Gln
    1100                1105                1110

Lys Ala  Ala Leu Tyr Gly Gln  Thr Tyr Pro Ala Gln  Gly Pro Pro
    1115                1120                1125

Leu Gln  Gly Gly Phe Asn Leu  Gln Gly Gln Ser Pro  Ser Phe Asn
    1130                1135                1140

Ser Met  Met Gly Gln Ile Ser  Gln Gln Gly Ser Phe  Pro Leu Gln
    1145                1150                1155

Gly Met  His Pro Arg Ala Gly  Leu Val Arg Pro Arg  Thr Asn Thr
    1160                1165                1170

Pro Lys  Gln Leu Arg Met Gln  Leu Gln Gln Arg Leu  Gln Gly Gln
    1175                1180                1185
```

```
Gln Phe Leu Asn Gln Ser Arg Gln Ala Leu Glu Met Lys Met Glu
    1190                1195                1200

Asn Pro Ala Gly Thr Ala Val Met Arg Pro Met Met Pro Gln Ala
    1205                1210                1215

Phe Phe Asn Ala Gln Met Ala Ala Gln Gln Lys Arg Glu Leu Met
    1220                1225                1230

Ser His His Leu Gln Gln Gln Arg Met Ala Met Met Ser Gln
    1235                1240                1245

Pro Gln Pro Gln Ala Phe Ser Pro Pro Asn Val Thr Ala Ser
    1250                1255                1260

Pro Ser Met Asp Gly Val Leu Ala Gly Ser Ala Met Pro Gln Ala
    1265                1270                1275

Pro Pro Gln Gln Phe Pro Tyr Pro Ala Asn Tyr Gly Thr Gly Gln
    1280                1285                1290

Pro Pro Val Ala Ser Leu Trp Ser Arg Leu Glu Ser Ser Gln Cys
    1295                1300                1305

Asn Asp Val Ile Lys Asn Gly Ala Phe Pro Glu Cys His Gly Ala
    1310                1315                1320

Ala Ser Ser Ala His Thr His Val Ser Ala Phe Arg Tyr Glu Gly
    1325                1330                1335

Val Ala Val Arg Glu Pro Gly Gln Glu Trp Leu Leu Pro Pro Ala
    1340                1345                1350

Ala Val Cys Ser Pro Gly Glu Pro Cys Ser Leu Gln His Gly Ala
    1355                1360                1365

Tyr Glu Gln Gln Arg Trp Ala Leu Gly Thr Asp Gly His Asp Pro
    1370                1375                1380

His Ala His Val Trp His Ala His Gly Pro Arg Ser Glu Ile Leu
    1385                1390                1395

Leu Thr Ser Pro
    1400

<210> SEQ ID NO 3
<211> LENGTH: 1463
<212> TYPE: PRT
<213> ORGANISM: Mus musculus

<400> SEQUENCE: 3

Met Ser Gly Met Gly Glu Asn Thr Ser Asp Pro Ser Arg Ala Glu Thr
1               5                   10                  15

Arg Lys Arg Lys Glu Cys Pro Asp Gln Leu Gly Pro Ser Pro Lys Arg
                20                  25                  30

Ser Thr Glu Lys Arg Asn Arg Glu Gln Glu Asn Lys Tyr Ile Glu Glu
            35                  40                  45

Leu Ala Glu Leu Ile Phe Ala Asn Phe Asn Asp Ile Asp Asn Phe Asn
50                  55                  60

Phe Lys Pro Asp Lys Cys Ala Ile Leu Lys Glu Thr Val Lys Gln Ile
65                  70                  75                  80

Arg Gln Ile Lys Glu Gln Glu Lys Ala Ala Ala Ala Asn Ile Asp Glu
                85                  90                  95

Val Gln Lys Ser Asp Val Ser Ser Thr Gly Gln Gly Val Ile Asp Lys
            100                 105                 110

Asp Ala Leu Gly Pro Met Met Leu Glu Ala Leu Asp Gly Phe Phe Phe
        115                 120                 125

Val Val Asn Leu Glu Gly Ser Val Val Phe Val Phe Arg Asn Val Thr
```

-continued

```
            130                 135                 140
Gln Tyr Leu Arg Tyr Asn Gln Glu Glu Leu Met Asn Lys Ser Val Tyr
145                 150                 155                 160

Ser Ile Leu His Val Gly Asp His Thr Glu Phe Val Lys Asn Leu Leu
                165                 170                 175

Pro Lys Ser Met Val Asn Gly Gly Ser Trp Ser Gly Glu Pro Pro Arg
                180                 185                 190

Arg Ser Ser His Thr Phe Asn Cys Arg Met Leu Val Lys Pro Leu Pro
                195                 200                 205

Asp Ser Glu Glu Glu Gly His Asp Ser Gln Ala His Gln Lys Tyr
210                 215                 220

Glu Ala Met Gln Cys Phe Ala Val Ser Gln Pro Lys Ser Ile Lys Glu
225                 230                 235                 240

Glu Gly Glu Asp Leu Gln Ser Cys Leu Ile Val Trp His Glu Asp Pro
                245                 250                 255

His Glu Gly Lys Thr Asn Ser Ser Leu Ile Arg Lys Leu Tyr His Pro
                260                 265                 270

Pro Gly Pro Pro Arg Gln Asp His Phe Thr Gly His Tyr His His Glu
                275                 280                 285

Ser Arg His Glu Ala Gly Leu Gly Arg Ser Gly Lys Lys Asp Ala Phe
290                 295                 300

Arg Ser Ser Thr His Ser Met Lys Gly Ser Leu Tyr His Met Pro Arg
305                 310                 315                 320

Arg His His His Glu Val Leu Arg Gln Gly Leu Ala Phe Ser Gln Ile
                325                 330                 335

Tyr Arg Phe Ser Leu Ser Asp Gly Thr Leu Val Ala Ala Gln Thr Lys
                340                 345                 350

Ser Lys Leu Ile Arg Ser Gln Thr Thr Asn Glu Pro Gln Leu Val Ile
                355                 360                 365

Ser Leu His Met Leu His Arg Glu Gln Asn Val Cys Val Met Asn Pro
                370                 375                 380

Asp Leu Thr Gly Gln Ala Met Gly Lys Pro Leu Asn Pro Ile Ser Ser
385                 390                 395                 400

Ser Ser Pro Ala His Gln Ala Leu Cys Ser Gly Asn Pro Gly Gln Asp
                405                 410                 415

Met Thr Leu Ser Ser Asn Ile Asn Phe Pro Met Asn Gly Pro Lys Glu
                420                 425                 430

Gln Met Gly Met Pro Met Gly Arg Phe Gly Ser Gly Gly Met Asn
                435                 440                 445

His Val Ser Gly Met Gln Ala Thr Thr Pro Gln Gly Ser Asn Tyr Ala
                450                 455                 460

Leu Lys Met Asn Ser Pro Ser Gln Ser Ser Pro Gly Met Asn Pro Gly
465                 470                 475                 480

Gln Ala Ser Ser Val Leu Ser Pro Arg Gln Arg Met Ser Pro Gly Val
                485                 490                 495

Ala Gly Ser Pro Arg Ile Pro Pro Ser Gln Phe Ser Pro Ala Gly Asn
                500                 505                 510

Leu His Ser Pro Val Gly Val Cys Ser Ser Thr Gly Asn Ser His Ser
                515                 520                 525

Tyr Thr Asn Ser Ser Leu Asn Ala Leu Gln Ala Leu Ser Glu Gly His
                530                 535                 540

Gly Val Ser Leu Gly Ser Ser Leu Ala Ser Pro Asp Leu Lys Met Gly
545                 550                 555                 560
```

```
Asn Leu Gln Asn Ser Pro Val Asn Met Asn Pro Pro Leu Ser Lys
            565                 570                 575
Met Gly Ser Leu Asp Ser Lys Asp Cys Phe Gly Leu Tyr Gly Glu Pro
        580                 585                 590
Ser Lys Gly Thr Thr Gly Gln Ala Glu Ala Ser Cys His Pro Lys Lys
    595                 600                 605
Gln Lys Gly Pro Asn Asp Ser Ser Met Pro Gln Ala Ala Ser Gly Asp
610                 615                 620
Arg Ala Glu Gly His Ser Arg Leu His Asp Ser Lys Gly Gln Thr Lys
625                 630                 635                 640
Leu Leu Gln Leu Leu Thr Thr Lys Ser Asp Gln Met Glu Pro Ser Pro
                645                 650                 655
Leu Pro Ser Ser Leu Ser Asp Thr Asn Lys Asp Ser Thr Gly Ser Leu
            660                 665                 670
Pro Gly Pro Gly Ser Thr His Gly Thr Ser Leu Lys Glu Lys His Lys
        675                 680                 685
Ile Leu His Arg Leu Leu Gln Asp Ser Ser Ser Pro Val Asp Leu Ala
    690                 695                 700
Lys Leu Thr Ala Glu Ala Thr Gly Lys Glu Leu Ser Gln Glu Ser Ser
705                 710                 715                 720
Ser Thr Ala Pro Gly Ser Glu Val Thr Val Lys Gln Glu Pro Ala Ser
                725                 730                 735
Pro Lys Lys Lys Glu Asn Ala Leu Leu Arg Tyr Leu Leu Asp Lys Asp
            740                 745                 750
Asp Thr Lys Asp Ile Gly Leu Pro Glu Ile Thr Pro Lys Leu Glu Arg
        755                 760                 765
Leu Asp Ser Lys Thr Asp Pro Ala Ser Asn Thr Lys Leu Ile Ala Met
    770                 775                 780
Lys Thr Val Lys Glu Glu Val Ser Phe Glu Pro Ser Asp Gln Pro Gly
785                 790                 795                 800
Ser Glu Leu Asp Asn Leu Glu Glu Ile Leu Asp Asp Leu Gln Asn Ser
                805                 810                 815
Gln Leu Pro Gln Leu Phe Pro Asp Thr Arg Pro Gly Ala Pro Thr Gly
            820                 825                 830
Ser Val Asp Lys Gln Ala Ile Ile Asn Asp Leu Met Gln Leu Thr Ala
        835                 840                 845
Asp Ser Ser Pro Val Pro Pro Ala Gly Ala Gln Lys Ala Ala Leu Cys
    850                 855                 860
Met Ser Gln Ser Ser Phe Asn Asn Pro Arg Pro Gly Gln Leu Gly Arg
865                 870                 875                 880
Leu Leu Pro Tyr Gln Asn Leu Pro Leu Asp Ile Thr Leu Gln Ser Pro
                885                 890                 895
Thr Gly Ala Gly Pro Phe Pro Pro Ile Arg Asn Ser Ser Pro Tyr Ser
            900                 905                 910
Val Ile Pro Gln Pro Gly Met Met Gly Asn Gln Gly Met Leu Gly Ser
        915                 920                 925
Gln Gly Asn Leu Gly Asn Asn Ser Thr Gly Met Ile Gly Ser Ser Thr
    930                 935                 940
Ser Arg Pro Ser Met Pro Ser Gly Glu Trp Ala Pro Gln Ser Thr Ser
945                 950                 955                 960
Cys Glu Ser Thr Leu Val Leu Pro Leu Val Pro Arg Thr Asp Gln
                965                 970                 975
```

-continued

```
Ser Lys Glu Ala Arg Phe Gly Asn Pro Thr Ala Ser Ile Pro Met Gly
            980                 985                 990

Ala Asn Ser Gln Leu Gly Gln Arg  Gln Met Leu Gln Ser  Gln Val Met
            995                 1000                1005

Asn Ile  Gly Pro Ser Glu Leu  Glu Met Asn Met Gly  Gly Pro Gln
        1010                 1015                1020

Tyr Asn  Gln Gln Gln Ala Pro  Pro Asn Gln Thr Ala  Pro Trp Pro
        1025                 1030                1035

Glu Ser  Ile Leu Pro Ile Asp  Gln Ala Ser Phe Ala  Ser Gln Asn
        1040                 1045                1050

Arg Gln  Pro Phe Gly Ser Ser  Pro Asp Asp Leu Leu  Cys Pro His
        1055                 1060                1065

Pro Ala  Ala Glu Ser Pro Ser  Asp Glu Gly Ala Leu  Leu Asp Gln
        1070                 1075                1080

Leu Tyr  Leu Ala Leu Arg Asn  Phe Asp Gly Leu Glu  Glu Ile Asp
        1085                 1090                1095

Arg Ala  Leu Gly Ile Pro Glu  Leu Val Ser Gln Ser  Gln Ala Val
        1100                 1105                1110

Asp Ala  Glu Gln Phe Ser Ser  Gln Glu Ser Ser Ile  Met Leu Glu
        1115                 1120                1125

Gln Lys  Pro Pro Val Phe Pro  Gln Gln Tyr Ala Ser  Gln Ala Gln
        1130                 1135                1140

Met Ala  Gln Gly Gly Tyr Asn  Pro Met Gln Asp Pro  Asn Phe His
        1145                 1150                1155

Thr Met  Gly Gln Arg Pro Asn  Tyr Thr Thr Leu Arg  Met Gln Pro
        1160                 1165                1170

Arg Pro  Gly Leu Arg Pro Thr  Gly Ile Val Gln Asn  Gln Pro Asn
        1175                 1180                1185

Gln Leu  Arg Leu Gln Leu Gln  His Arg Leu Gln Ala  Gln Gln Asn
        1190                 1195                1200

Arg Gln  Pro Leu Met Asn Gln  Ile Ser Ser Val Ser  Asn Val Asn
        1205                 1210                1215

Leu Thr  Leu Arg Pro Gly Val  Pro Thr Gln Ala Pro  Ile Asn Ala
        1220                 1225                1230

Gln Met  Leu Ala Gln Arg Gln  Arg Glu Ile Leu Asn  Gln His Leu
        1235                 1240                1245

Arg Gln  Arg Gln Met Gln Gln  Val Gln Gln Arg Thr  Leu Met
        1250                 1255                1260

Met Arg  Gly Gln Gly Leu Asn  Val Thr Pro Ser Met  Val Ala Pro
        1265                 1270                1275

Ala Gly  Leu Pro Ala Ala Met  Ser Asn Pro Arg Ile  Pro Gln Ala
        1280                 1285                1290

Asn Ala  Gln Gln Phe Pro Phe  Pro Pro Asn Tyr Gly  Ile Ser Gln
        1295                 1300                1305

Gln Pro  Asp Pro Gly Phe Thr  Gly Ala Thr Thr Pro  Gln Ser Pro
        1310                 1315                1320

Leu Met  Ser Pro Arg Met Ala  His Thr Gln Ser Pro  Met Met Gln
        1325                 1330                1335

Gln Ser  Gln Ala Asn Pro Ala  Tyr Gln Pro Thr Ser  Asp Met Asn
        1340                 1345                1350

Gly Trp  Ala Gln Gly Ser Met  Gly Gly Asn Ser Met  Phe Ser Gln
        1355                 1360                1365

Gln Ser  Pro Pro His Phe Gly  Gln Gln Ala Asn Thr  Ser Met Tyr
```

-continued

```
            1370                1375                1380
Ser Asn Asn Met Asn Ile Ser Val Ser Met Ala Thr Asn Thr Gly
        1385                1390                1395

Gly Leu Ser Ser Met Asn Gln Met Thr Gly Gln Met Ser Met Thr
    1400                1405                1410

Ser Val Thr Ser Val Pro Thr Ser Gly Leu Pro Ser Met Gly Pro
    1415                1420                1425

Glu Gln Val Asn Asp Pro Ala Leu Arg Gly Gly Asn Leu Phe Pro
    1430                1435                1440

Asn Gln Leu Leu Gly Met Asp Met Ile Lys Gln Glu Gly Asp Ala
    1445                1450                1455

Ser Arg Lys Tyr Cys
    1460

<210> SEQ ID NO 4
<211> LENGTH: 13
<212> TYPE: PRT
<213> ORGANISM: Mus musculus

<400> SEQUENCE: 4

Gln Thr Ser His Lys Leu Val Gln Leu Leu Thr Thr Ala
1               5                   10

<210> SEQ ID NO 5
<211> LENGTH: 15
<212> TYPE: PRT
<213> ORGANISM: Mus musculus

<400> SEQUENCE: 5

Ser Leu Thr Glu Arg His Lys Arg Leu His Arg Leu Leu Gln Glu
1               5                   10                  15

<210> SEQ ID NO 6
<211> LENGTH: 15
<212> TYPE: PRT
<213> ORGANISM: Mus musculus

<400> SEQUENCE: 6

Ser Lys Asp His Gln Leu Leu Arg Tyr Leu Leu Asp Lys Asp Glu
1               5                   10                  15

<210> SEQ ID NO 7
<211> LENGTH: 13
<212> TYPE: PRT
<213> ORGANISM: Mus musculus

<400> SEQUENCE: 7

Ser Ser Ser Gln Leu Asp Glu Leu Leu Cys Pro Pro Thr
1               5                   10

<210> SEQ ID NO 8
<211> LENGTH: 11
<212> TYPE: PRT
<213> ORGANISM: Mus musculus

<400> SEQUENCE: 8

Lys Ala Leu Leu Glu Gln Leu Val Ser Phe Leu
1               5                   10

<210> SEQ ID NO 9
<211> LENGTH: 12
<212> TYPE: PRT
```

-continued

```
<213> ORGANISM: Mus musculus

<400> SEQUENCE: 9

Gln Gln Lys Ser Leu Leu Gln Gln Leu Leu Thr Glu
1               5                   10

<210> SEQ ID NO 10
<211> LENGTH: 12
<212> TYPE: PRT
<213> ORGANISM: Mus musculus

<400> SEQUENCE: 10

Lys His Lys Gln Leu Ser Glu Leu Leu Arg Gly Gly
1               5                   10

<210> SEQ ID NO 11
<211> LENGTH: 13
<212> TYPE: PRT
<213> ORGANISM: Mus musculus

<400> SEQUENCE: 11

Ser Pro Ser Ala Leu Gln Asp Leu Leu Arg Thr Leu Lys
1               5                   10

<210> SEQ ID NO 12
<211> LENGTH: 6
<212> TYPE: PRT
<213> ORGANISM: Mus musculus

<400> SEQUENCE: 12

Gln Leu Ala Ala Ala Ala
1               5

<210> SEQ ID NO 13
<211> LENGTH: 6
<212> TYPE: PRT
<213> ORGANISM: Mus musculus

<400> SEQUENCE: 13

Arg Leu Ala Ala Ala Ala
1               5

<210> SEQ ID NO 14
<211> LENGTH: 4
<212> TYPE: PRT
<213> ORGANISM: Mus musculus

<400> SEQUENCE: 14

Ala Ala Ala Ala
1
```

What is claimed is:

1. A substantially purified p/CIP polypeptide comprising the amino acid sequence shown in (SEQ ID NO.: 2).

2. A substantially purified active fragment of a murine p/CIP polypeptide, which fragment comprises a CBP interaction domain of a murine p/CIP polypeptide comprised of SEQ ID NO.: 2.

3. The substantially purified fragment of claim 2 comprising an amino acid sequence selected from the group consisting of about amino acids 758 to about 1115, about amino acids 947 to 1084, and about amino acids 163 to 610 of p/CIP SEQ ID NO.: 2.

4. A substantially purified fragment of a murine p/CIP polypeptide, which fragment comprises an amino acid sequence selected from the group consisting of about amino acids 591 to 803, and about amino acids 680 to 740 of p/CIP SEQ ID NO.: 2.

5. A substantially purified fragment of a murine p/CIP polypeptide, which fragment comprises a sequence selected from the group consisting of amino acid sequences 609–621, 670–684, 723–738, 1037–1049, and 1058–1068 of p/CIP SEQ ID NO.: 2.

6. A method of identifying an effective agent that alters the association of a p/CIP polypeptide of claim 1 with a second protein, comprising the steps of:

(a) contacting the p/CIP polypeptide and the second protein with an agent under conditions that allow the p/CIP polypeptide to associate with the second protein; and
(b) detecting an altered association of the p/CIP polypeptide and the second protein.

7. The method of claim 6, wherein the second protein is selected from the group consisting of a CBP protein, a nuclear receptor and a CBP/p300-dependent transcription factor.

8. The method of claim 6, wherein the altered association is detected by measuring the transcriptional activity of a reporter gene.

9. The method of claim 6, wherein the contacting is in vitro.

10. The method of claim 6, wherein the contacting is in a mammalian cell or a yeast cell.

* * * * *